US012680110B2

(12) United States Patent

He

(10) Patent No.: US 12,680,110 B2

(45) Date of Patent: Jul. 14, 2026

(54) ONE-STEP METHOD FOR PRODUCING ADENOVIRAL VECTORS

(71) Applicant: The University of Chicago, Chicago, IL (US)

(72) Inventor: Tong-Chuan He, Chicago, IL (US)

(73) Assignee: The University of Chicago, Chicago, IL (US)

( * ) Notice: Subject to any disclaimer, the term of this patent is extended or adjusted under 35 U.S.C. 154(b) by 483 days.

(21) Appl. No.: 17/819,539

(22) Filed: Aug. 12, 2022

(65) Prior Publication Data

US 2023/0071166 A1 Mar. 9, 2023

Related U.S. Application Data

(60) Provisional application No. 63/232,326, filed on Aug. 12, 2021.

(51) Int. Cl.
*C12N 15/85* (2006.01)
*C07K 14/245* (2006.01)
*C12N 15/86* (2006.01)

(52) U.S. Cl.
CPC ............ *C12N 15/86* (2013.01); *C07K 14/245* (2013.01); *C12N 2710/10043* (2013.01)

(58) Field of Classification Search
CPC ................ C12N 15/1093; C12N 15/86; C12N 2710/10043; C07K 14/245
See application file for complete search history.

(56) References Cited

U.S. PATENT DOCUMENTS

| | | | |
|---|---|---|---|
| 5,994,128 A | 11/1999 | Fallaux et al. | |
| 5,998,205 A | 12/1999 | Hallenbeck et al. | |
| 6,033,908 A | 3/2000 | Bout et al. | |
| 6,194,191 B1 | 2/2001 | Zhang et al. | |
| 6,225,289 B1 | 5/2001 | Kovesdi et al. | |
| 6,514,943 B2 | 2/2003 | Kovesdi et al. | |
| 6,824,771 B1 | 11/2004 | Curiel et al. | |
| 7,456,009 B2 | 11/2008 | Evans et al. | |
| 7,888,096 B2 | 2/2011 | Wu et al. | |
| 10,272,032 B2 | 4/2019 | Adriaansen | |
| 2015/0374766 A1* | 12/2015 | O'Shea et al. ......... | C12N 15/86 |

FOREIGN PATENT DOCUMENTS

| | | | |
|---|---|---|---|
| WO | WO 96/27677 | 9/1996 | |
| WO | WO 97/00326 | 1/1997 | |
| WO | WO 98/00524 | 1/1998 | |
| WO | WO 98/22588 | 5/1998 | |
| WO | WO 99/54441 | 10/1999 | |
| WO | WO 00/34444 | 6/2000 | |
| WO | WO 03/078592 | 9/2003 | |
| WO | WO 2009/117656 A2 * | 9/2009 | ............ A61K 48/00 |

OTHER PUBLICATIONS

Guo et al NPL literature on application of Gibson DNA Assembly Kit to modify adenoviral vector (Year: 2019).*
Invitrogen manual for Gateway cloning vector technology (Year: 2012).*
NEBuilder_HiFI_DNA-Assembly_Master Mix Manual_2014 (Year: 2014).*
Bahassi et al., F plasmid CcdB killer protein: ccdB gene mutants coding for non-cytotoxic proteins which retain their regulatory functions. Mol Microbiol. Mar. 1995;15(6):1031-7.
Bernard et al., Positive-selection vectors using the F plasmid ccdB killer gene. Gene. Oct. 11, 1994;148(1):71-4.
Bernard. Positive selection of recombinant DNA by CcdB. Biotechniques. Aug. 1996;21(2):320-3.
Breyer et al., Adenoviral vector-mediated gene transfer for human gene therapy. Curr Gene Ther. Jul. 2001;1(2):149-62.
Cao et al., Blockade of IGF/IGF-1R signaling axis with soluble IGF-1R mutants suppresses the cell proliferation and tumor growth of human osteosarcoma. Am J Cancer Res. Oct. 1, 2020;10(10):3248-3266.
Chartier et al., Efficient generation of recombinant adenovirus vectors by homologous recombination in *Escherichia coli*. J Virol. Jul. 1996;70(7):4805-10.
Chen et al., Insulin-like growth factor 2 (IGF-2) potentiates BMP-9-induced osteogenic differentiation and bone formation. J Bone Miner Res. Nov. 2010;25(11):2447-59.
Cheng et al., Osteogenic activity of the fourteen types of human bone morphogenetic proteins (BMPs). J Bone Joint Surg Am. Aug. 2003;85(8):1544-52.
Crystal et al., Adenovirus: the first effective in vivo gene delivery vector. Hum Gene Ther. Jan. 2014;25(1):3-11.
Curiel et al., High-efficiency gene transfer mediated by adenovirus coupled to DNA-polylysine complexes. Hum Gene Ther. Apr. 1992;3(2):147-54.
Deng et al., A simplified and versatile system for the simultaneous expression of multiple siRNAs in mammalian cells using Gibson DNA Assembly. PLoS One. Nov. 14, 2014;9(11):e113064. 12 pages.
Ehrke-Schulz et al., Recent Advances in Preclinical Developments Using Adenovirus Hybrid Vectors. Hum Gene Ther. Oct. 2017;28(10):833-841.
Fan et al., A simplified system for the effective expression and delivery of functional mature microRNAs in mammalian cells. Cancer Gene Ther. Jun. 2020;27(6):424-437.
Fan et al., Noncanonical Wnt signaling plays an important role in modulating canonical Wnt-regulated stemness, proliferation and terminal differentiation of hepatic progenitors. Oncotarget. Apr. 18, 2017;8(16):27105-27119.
Knipe et al., Fields Virology, 5th ed., Lippincott Williams & Wilkins, Philadelphia, Pa. 2006. TOC only 6 pages.

(Continued)

*Primary Examiner* — Marcia S Noble

(74) *Attorney, Agent, or Firm* — David W. Staple; Casimir Jones, S.C.

(57) ABSTRACT

The disclosure is directed to a gene transfer vector which comprises (i) all or part of a viral genome and (ii) a suicide gene flanked by unique cloning sequences. The disclosure also is directed to a system for producing an adenoviral vector comprising a destination vector comprising (i) all or part of an adenoviral genome and (ii) a suicide gene flanked by unique cloning sequences; a transgene flanked by unique cloning sequences; and (c) reagents for Gibson DNA Assembly (GDA). A method of producing an adenoviral vector using the aforementioned system also is provided.

11 Claims, 13 Drawing Sheets

Specification includes a Sequence Listing.

(56)　　　　　References Cited

OTHER PUBLICATIONS

Gibson et al., Enzymatic assembly of overlapping DNA fragments. Methods Enzymol. 2011;498:349-61.

Gibson et al., Enzymatic assembly of DNA molecules up to several hundred kilobases. Nat Methods. May 2009;6(5):343-5.

Ginsberg et al., A proposed terminology for the adenovirus antigens and virion morphological subunits. Virology. Apr. 1966;28(4):782-3.

Graham et al., Characteristics of a human cell line transformed by DNA from human adenovirus type 5. J Gen Virol. Jul. 1977;36(1):59-74.

Graham et al., Methods for construction of adenovirus vectors. Mol Biotechnol. Jun. 1995;3(3):207-20.

Hamdan et al., GAMER-Ad: a novel and rapid method for generating recombinant adenoviruses. Mol Ther Methods Clin Dev. Feb. 4, 2021;20:625-634.

Hardy et al., Construction of adenovirus vectors through Cre-lox recombination. J Virol. Mar. 1997;71(3):1842-9.

He et al., FAMSi: A Synthetic Biology Approach to the Fast Assembly of Multiplex siRNAs for Silencing Gene Expression in Mammalian Cells. Mol Ther Nucleic Acids. Oct. 14, 2020;22:885-899.

He et al., Adenoviral Vectors in Current Protocols in Human Genetics. John Wiley & Sons, Inc., New York, 2001, vol. Unit 12.4, pp. 12.14.11-12.14.25.

He et al., A simplified system for generating recombinant adenoviruses. Proc Natl Acad Sci U S A. Mar. 3, 1998;95(5):2509-14.

Helin. Regulation of cell proliferation by the E2F transcription factors. Curr Opin Genet Dev. Feb. 1998;8(1):28-35.

Howe et al., Retinoblastoma growth suppressor and a 300-kDa protein appear to regulate cellular DNA synthesis. Proc Natl Acad Sci USA. Aug. 1990;87(15):5883-7.

Howe et al., Effects of Ad5 E1A mutant viruses on the cell cycle in relation to the binding of cellular proteins including the retinoblastoma protein and cyclin A. Virology. Jan. 1992;186(1):15-24.

Hu et al., CRISPR/Cas9-mediated reversibly immortalized mouse bone marrow stromal stem cells (BMSCs) retain multipotent features of mesenchymal stem cells (MSCs). Oncotarget. Dec. 5, 2017;8(67):111847-111865.

Huang et al., SATB2: A versatile transcriptional regulator of craniofacial and skeleton development, neurogenesis and tumorigenesis, and its applications in regenerative medicine. Genes Dis. Oct. 17, 2020;9(1):95-107.

Kang et al., Characterization of the distinct orthotopic bone-forming activity of 14 BMPs using recombinant adenovirus-mediated gene delivery. Gene Ther. Sep. 2004;11(17):1312-20.

Ketner et al., Efficient manipulation of the human adenovirus genome as an infectious yeast artificial chromosome clone. Proc Natl Acad Sci U S A. Jun. 21, 1994;91(13):6186-90.

Lee et al., Adenovirus-Mediated Gene Delivery: Potential Applications for Gene and Cell-Based Therapies in the New Era of Personalized Medicine. Genes Dis. Jun. 2017;4(2):43-63.

Li et al., Targeting BMP9-promoted human osteosarcoma growth by inactivation of notch signaling. Curr Cancer Drug Targets. 2014;14(3):274-85.

Li et al., Long non-coding RNA (LncRNA) HOTAIR regulates BMP9-induced osteogenic differentiation by targeting the proliferation of mesenchymal stem cells (MSCs) Aging (Albany NY). Jan. 10, 2021;13(3):4199-4214.

Lienert et al., Synthetic biology in mammalian cells: next generation research tools and therapeutics. Nat Rev Mol Cell Biol. Feb. 2014;15(2):95-107.

Liu et al., Highly expressed BMP9/GDF2 in postnatal mouse liver and lungs may account for its pleiotropic effects on stem cell differentiation, angiogenesis, tumor growth and metabolism. Genes Dis. Sep. 14, 2019;7(2):235-244.

Liu et al., Structure of the retinoblastoma protein bound to adenovirus E1A reveals the molecular basis for viral oncoprotein inactivation of a tumor suppressor. Genes Dev. Nov. 1, 2007;21(21):2711-6.

Luo et al., A protocol for rapid generation of recombinant adenoviruses using the AdEasy system. Nat Protoc. 2007;2(5):1236-47.

Luo et al., BMP9-initiated osteogenic/odontogenic differentiation of mouse tooth germ mesenchymal cells (TGMCS) requires Wnt/β-catenin signalling activity. J Cell Mol Med. Mar. 2021;25(5):2666-2678.

Maggio et al., Selection-free gene repair after adenoviral vector transduction of designer nucleases: rescue of dystrophin synthesis in DMD muscle cell populations. Nucleic Acids Res. Feb. 18, 2016;44(3):1449-70.

Mao et al., Argonaute (AGO) proteins play an essential role in mediating BMP9-induced osteogenic signaling in mesenchymal stem cells (MSCs). Genes Dis. May 13, 2021;8(6):918-930.

Miciak et al., Seamless assembly of recombinant adenoviral genomes from high-copy plasmids. PLoS One. Jun. 27, 2018;13(6):e0199563. 1-15.

Mizuguchi et al., Efficient construction of a recombinant adenovirus vector by an improved in vitro ligation method. Hum Gene Ther. Nov. 20, 1998;9(17):2577-83.

Mostafa et al., The wonders of BMP9: From mesenchymal stem cell differentiation, angiogenesis, neurogenesis, tumorigenesis, and metabolism to regenerative medicine. Genes Dis. Jul. 24, 2019;6(3):201-223.

Ng et al., A high-efficiency Cre/loxP-based system for construction of adenoviral vectors. Hum Gene Ther. Nov. 1, 1999;10(16):2667-72.

Pan et al., Rapid Construction of a Replication-Competent Infectious Clone of Human Adenovirus Type 14 by Gibson Assembly. Viruses. Oct. 18, 2018;10(10):568. 16 pages.

Roberts et al., Three-dimensional structure of the adenovirus major coat protein hexon. Science. May 30, 1986;232(4754):1148-51.

Song et al., BMP9 induces osteogenesis and adipogenesis in the immortalized human cranial suture progenitors from the patent sutures of craniosynostosis patients. J Cell Mol Med. Nov. 2017;21(11):2782-2795.

Stewart et al., Image reconstruction reveals the complex molecular organization of adenovirus. Cell. Oct. 4, 1991;67(1):145-54.

Stewart et al., Difference imaging of adenovirus: bridging the resolution gap between X-ray crystallography and electron microscopy. EMBO J. Jul. 1993;12(7):2589-99.

Sundararajan et al., E1B 19K blocks Bax oligomerization and tumor necrosis factor alpha-mediated apoptosis. J Virol. Aug. 2001;75(16):7506-16.

Wang et al., E1A induces phosphorylation of the retinoblastoma protein independently of direct physical association between the E1A and retinoblastoma products. Mol Cell Biol. Aug. 1991;11(8):4253-65.

Wang et al., Development of a simplified and inexpensive RNA depletion method for plasmid DNA purification using size selection magnetic beads (SSMBs). Genes Dis. May 20, 2020;8(3):298-306.

Wei et al., Engineering the Rapid Adenovirus Production and Amplification (RAPA) Cell Line to Expedite the Generation of Recombinant Adenoviruses. Cell Physiol Biochem. 2017;41(6):2383-2398.

Wu et al., Overexpression of Ad5 precursor terminal protein accelerates recombinant adenovirus packaging and amplification in HEK-293 packaging cells. Gene Ther. Jul. 2014;21(7):629-37.

Wu et al., Modeling colorectal tumorigenesis using the organoids derived from conditionally immortalized mouse intestinal crypt cells (ciMICs). Genes Dis. Jan. 28, 2021;8(6):814-826.

Yan et al., Characterization of the essential role of bone morphogenetic protein 9 (BMP9) in osteogenic differentiation of mesenchymal stem cells (MSCs) through RNA interference. Genes Dis. Apr. 27, 2018;5(2):172-184.

Ye et al., A thermoresponsive polydiolcitrate-gelatin scaffold and delivery system mediates effective bone formation from BMP9-transduced mesenchymal stem cells. Biomed Mater. Apr. 21, 2016;11(2):025021. 14 pages.

Zhang et al., Leptin Potentiates BMP9-Induced Osteogenic Differentiation of Mesenchymal Stem Cells Through the Activation of JAK/STAT Signaling. Stem Cells Dev. Apr. 15, 2020;29(8):498-510.

(56) References Cited

OTHER PUBLICATIONS

Zhang et al., Canonical Wnt signaling acts synergistically on BMP9-induced osteo/odontoblastic differentiation of stem cells of dental apical papilla (SCAPs). Biomaterials. Jan. 2015;39:145-54.

Zhang et al., Transcriptomic landscape regulated by the 14 types of bone morphogenetic proteins (BMPs) in lineage commitment and differentiation of mesenchymal stem cells (MSCs). Genes Dis. May 8, 2019;6(3):258-275.

Zhang et al., lncRNA Rmst acts as an important mediator of BMP9-induced osteogenic differentiation of mesenchymal stem cells (MSCs) by antagonizing Notch-targeting microRNAs. Aging (Albany NY). Dec. 11, 2019;11(24):12476-12496.

Zhao et al., Adenovirus-mediated gene transfer in mesenchymal stem cells can be significantly enhanced by the cationic polymer polybrene. PLoS One. Mar. 21, 2014;9(3):e92908. 8 pages.

Zou et al., DNA assembly technique simplifies the construction of infectious clone of fowl adenovirus. J Virol Methods. Jul. 2018;257:85-92.

* cited by examiner

FIG. 2A

FIG. 2D
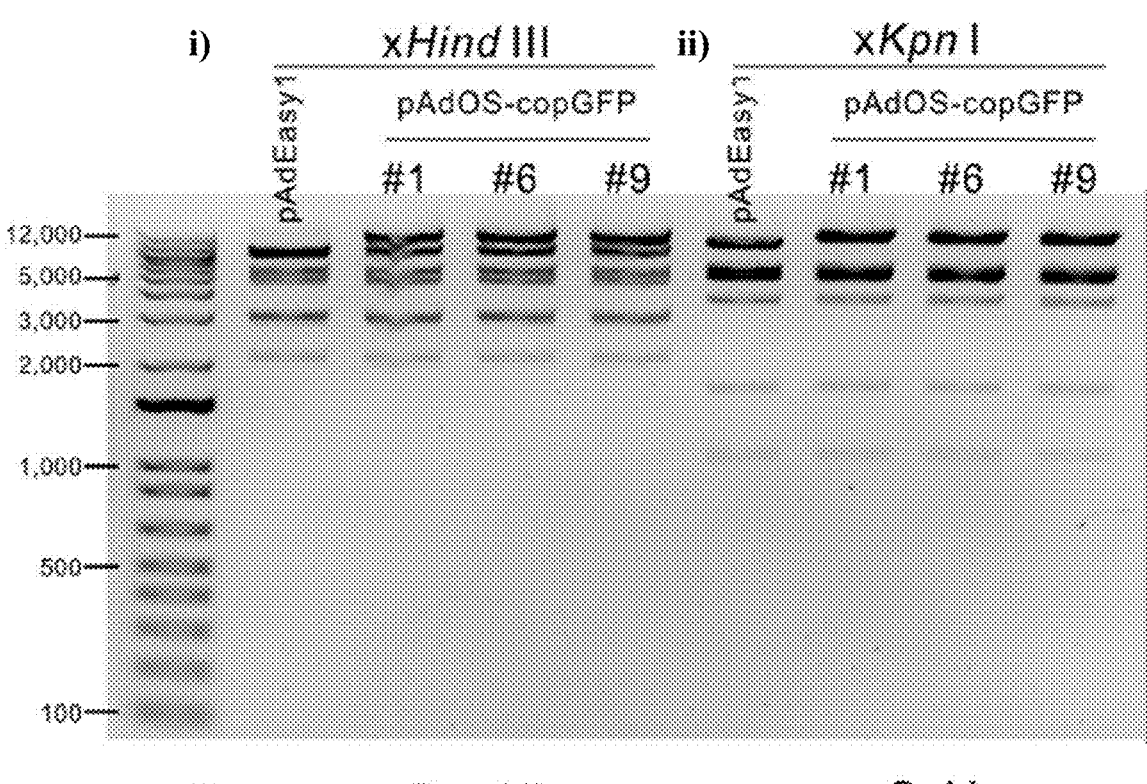
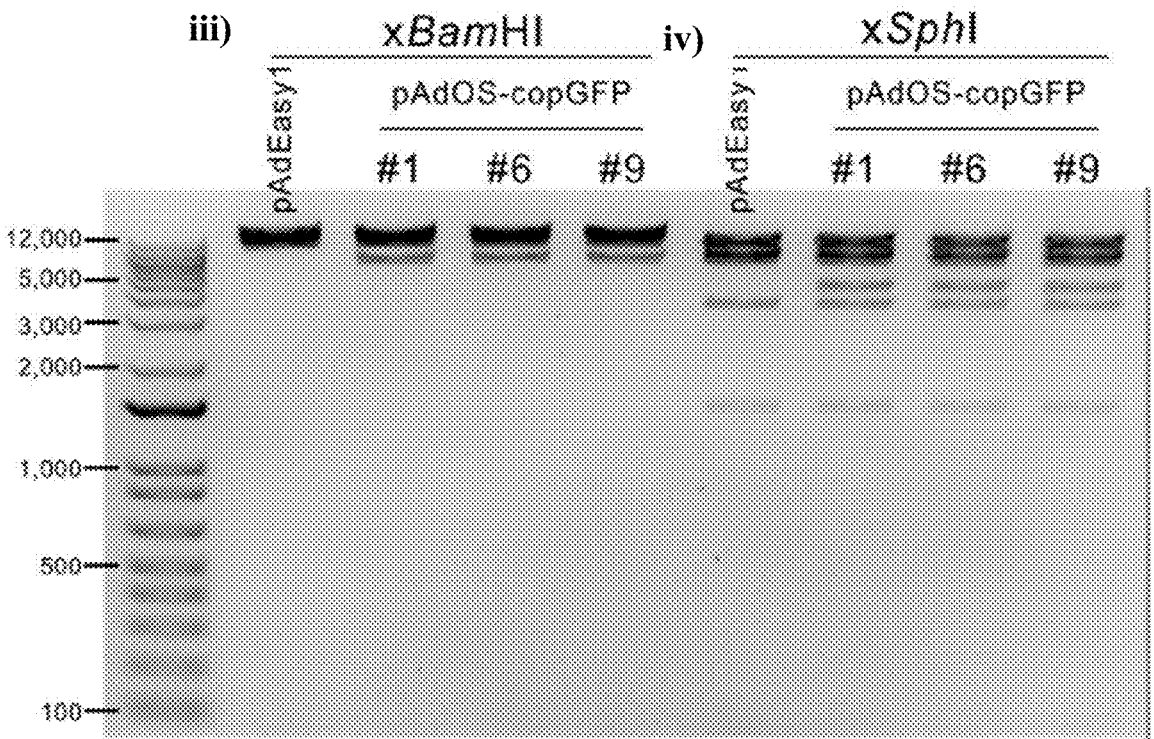

Figure 6:
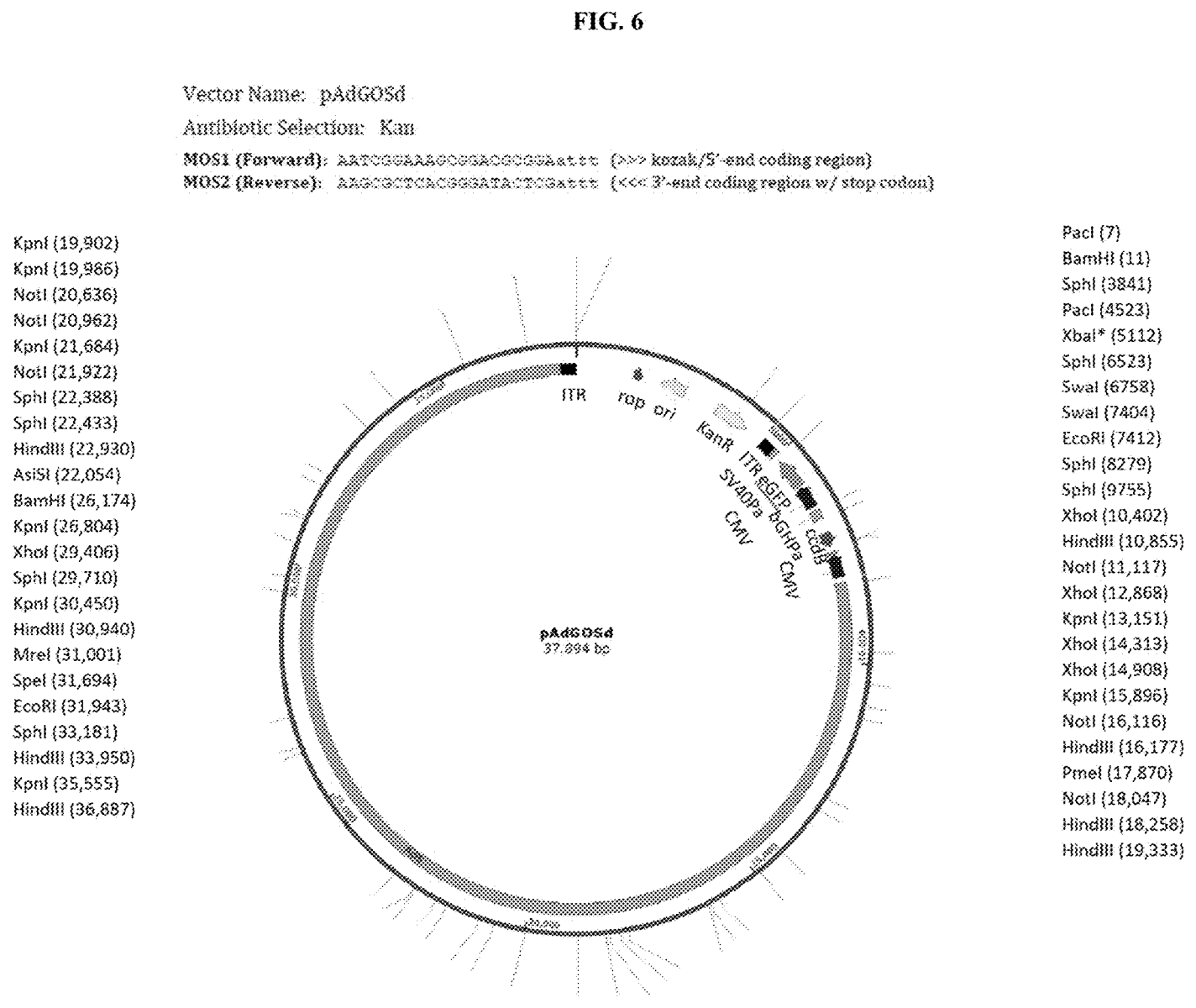

Vector Name: pAdGOSd

Antibiotic Selection: Kan

MOS1 (Forward): aatcccaaaccggcagccccaatte (>>> kozak/5'-end coding region)

MOS2 (Reverse): aagcccacccggaata cccaaccc (<<< 3'-end coding region w/ stop codon)

PacI (7)
BamHI (11)
SphI (3841)
PacI (4523)
XbaI* (5112)
SphI (6523)
SwaI (6758)
SwaI (7404)
EcoRI (7412)
SphI (8279)
SphI (9755)
XhoI (10,402)
HindIII (10,855)
NotI (11,117)
XhoI (12,868)
KpnI (13,151)
XhoI (14,313)
XhoI (14,908)
KpnI (15,896)
NotI (16,116)
HindIII (16,177)
PmeI (17,870)
NotI (18,047)
HindIII (18,258)
HindIII (19,333)

pAdGOSd
37,694 bp

Kpnl (19,902)
Kpnl (19,986)
Notl (20,636)
Notl (20,962)
Kpnl (21,684)
Notl (21,922)
Sphl (22,388)
Sphl (22,433)
HindIII (22,930)
AsiSI (22,054)
BamHI (26,174)
Kpnl (26,804)
Xhol (29,406)
Sphl (29,710)
Kpnl (30,450)
HindIII (30,940)
Mrel (31,001)
Spel (31,694)
EcoRI (31,943)
Sphl (33,181)
HindIII (33,950)
Kpnl (35,555)
HindIII (36,887)

FIG. 7

Vector Name: pAdHOS4

Antibiotic Selection: Kan

MOS1 (Forward): AATCGGAAAACGGAACGGAATT (>>> kozak/5'-end coding region)
MOS2 (Reverse): AAGCCTTCACCGAATCCGAATT (<<< 3'-end coding region with stop codon)

Pacl (7)
BamHI (11)
Sphl (3841)
Pacl (4627)
Xbal* (6162)
EcoRI (7134)
BamHI (7143)
Swal (7172)
Swal (7919)
Xbal (7843)
Sphl (8083)
Sphl (8277)
Sphl (9753)
HindIII (10,853)
NotI (11,115)
Kpnl (13,149)
Kpnl (15,896)
NotI (16,114)
HindIII (16,175)
Pmel (17,968)
NotI (18,045)
HindIII (18,256)
HindIII (19,331)

Kpnl (19,980)
Kpnl (19,986)
NotI (20,634)
NotI (20,960)
Kpnl (21,682)
Kpnl (21,920)
NotI (21,920)
Sphl (22,386)
Sphl (22,431)
HindIII (22,928)
AsiSI (22,052)
BamHI (26,172)
Kpnl (26,802)
Sphl (29,708)
Kpnl (30,448)
HindIII (30,939)
Mrel (30,999)
Spel (31,692)
EcoRI (31,941)
Sphl (33,179)
HindIII (33,948)
Kpnl (35,553)
HindIII (36,885)

pAdHOS4
37,0032 bp

ITR
rop ori
KanR ITR
CMV CMV ccdB
RFP CMV S
bGHPa
Factor Xa site

ONE-STEP METHOD FOR PRODUCING ADENOVIRAL VECTORS

SEQUENCE LISTING

The text of the computer readable sequence listing filed herewith, titled "39710-202_SEQUENCE_LISTING", created Aug. 12, 2022, having a file size of 7,473 bytes, is hereby incorporated by reference in its entirety.

BACKGROUND

Adenovirus (Ad) has received significant attention as an in vitro and in vivo gene delivery vehicle for several decades due to its well-defined virology and biology, its non-integrating property and viral genetic stability, its high gene transduction efficiency, and its ease of large-scale production (1-4). In fact, adenoviral vectors are not only used to deliver and express transgenes, but also are employed to express siRNAs for gene silencing and/or CRISPR/Cas and designer nucleases systems for genome editing (1, 4, 5). Adenovirus is a nonenveloped, linear double-stranded DNA virus. In humans, there are more than 50 identified serotypes, which are divided into 6 subgroups (A through G) based on their tropisms (1-4). Adenoviral capsids, which are comprised of capsid proteins, core proteins, and cement proteins, delineate tropisms among serotypes, and thus give rise to a vast range of therapeutic candidate viruses (1-4).

Compared with other viral vectors used for gene delivery, adenoviral vectors offer several distinct advantages (1-3). First, adenovirus is one of the most effective and non-integrating gene delivery systems in vitro and in vivo since most mammalian cells express the primary adenovirus receptor and secondary integrin receptors. Second, Ad vectors provide a versatile platform to modify viral capsids in order to enhance therapeutic properties and improve targeting specificity of the virus. Third, well-understood Ad virology and extensive experience with Ad vectors in preclinical and clinical applications make Ad vectors one of the most commonly used viral vectors in clinical trials worldwide. Fourth, the development of the third-generation gutless Ad vectors circumvents host anti-Ad immunity. Finally, even inherent shortcomings of adenovirus (e.g., evoked host immunity) have proven beneficial for anticancer immunotherapies, vaccination, and/or oncolytic therapies.

Despite the widespread use of adenoviral vectors, the construction and propagation of adenoviral vectors remains a technically challenging and time-consuming process. Thus, there is a need for improved systems and methods for producing adenoviral vectors.

BRIEF SUMMARY OF THE DISCLOSURE

The disclosure provides a gene transfer vector comprising (i) all or part of a viral genome and (ii) a suicide gene flanked by a first cloning nucleic acid sequence and a second cloning nucleic acid sequence, wherein the first and second cloning nucleic acid sequences are different.

The disclosure also provides system for producing an adenoviral vector, which comprises: (a) a destination vector comprising (i) all or part of an adenoviral genome and (ii) a suicide gene flanked by a first cloning nucleic acid sequence and a second cloning nucleic acid sequence, wherein the first and second cloning nucleic acid sequences are different; (b) a transgene flanked the first cloning nucleic acid sequence and the second cloning nucleic acid sequence; and (c)

reagents for Gibson DNA Assembly (GDA). A method of producing an adenoviral vector using the aforementioned system also is provided.

BRIEF DESCRIPTION OF THE DRAWING(S)

FIGS. 1A and B show a schematic depiction of the one-step construction of adenovirus (OSCA) system using the Gibson DNA Assembly technology. (A) Construction of the destination/recipient vectors for the OSCA system. Two unique sequences MOS1 and MOS2, flanking the unique SwaI site, were first engineered in a first-generation adenoviral shuttle vector, resulting in pShuttle-MOS (i). Linearized pShuttle-MOS was transformed into the pAdEasy-1-containing BJ5183 bacterial cells and selected for Kan-resistant pAdOS plasmid (ii), which was subsequently confirmed by PCR and sequencing. The ccdB gene fragment flanked with SwaI sites was assembled to the SwaI-linearized pAdOS through Gibson Assembly and grown in DB3.1 bacterial cells, resulting in the OSCA destination/recipient pAdOSd vector (iii). Two alternative destination vectors pAdGOSd and pAdROSd, which co-express GFP and RFP, respectively, were constructed in a similar fashion (FIGS. S1 and S2). (B) Gibson Assembly-mediated one-step construction of recombinant adenoviruses. The coding region of the gene of interest (GOI) is first PCR amplified with MOS1 and MOS2-anchored primers (i), and the purified PCR fragment is assembled with the SwaI-digested destination vector, e.g., pAdOSd, pAdGOSd, or pAdROSd, through Gibson Assembly reactions (ii). The resultant plasmids are verified, linearized by PacI digestion, and transfected into packaging cells such as 293pTP, leading to robust adenovirus generation in 5-7 days (iii). The adenoviral lysate can be further amplified in HEK-293 cells to accomplish high titers.

FIGS. 2A-D illustrate the construction and characterization of copGFP expressing adenoviral vector using the OSCA system. (A) Construction of AdOS-copGFP using the OSCA system. The copGFP coding sequence was PCR amplified with MOS1 and MOS2 anchored primers (i), followed by Gibson Assembly (ii). (B) Bacterial colonies post the Gibson Assembly reaction. (C) Identification of pAdOS-copGFP using PCR screening of bacterial colonies. Randomly picked up 16 colonies were PCR amplified with copGFP specific primers, and all but one (#11) were positive for copGFP. (D) Validation of adenoviral recombinant pAdOScopGFP clones. The representative three clones, along with the control adenoviral backbone vector pAdEasy1, were digested with Hind III (i), Kpn I (ii), Bam HI (iii), and Sph I (iv). The digested plasmid DNA was resolved in 1% agarose gels.

FIGS. 3A and B illustrate packaging and production of recombinant adenoviruses generated from the Gibson Assembly technology. (A) The initial production of AdOS-copGFP virus in 293pTP cells. At the indicated time points, GFP signal was also recorded. Comet-like adenovirus-producing foci were apparent at 5 days after transfection. Representative images are shown. Both GFP and bright field images were also recorded at a lower magnification (4x) (FIG. S3A). (B) Transduction efficiency of adenoviral lysate. The collected adenoviral lysate was used to infect subconfluent HEK-293 cells at the indicated viral titers (% of viral lysate volume).

FIGS. 4A-D illustrate the construction and production of mouse BMP9-expressing adenovirus vector using the OSCA system. (A) Packaging and production of recombinant adenoviruses generated from the Gibson Assembly technology. The coding region of mouse BMP9 was PCR amplified with gene-specific primers containing MOS1 and MOS2 sequences (i), and Gibson assembled with SwaI-digested pAdROSd vector to generate pAdROS-mBMP9 (ii). (B) Bacterial colony verification. The Gibson Assembly product was transformed into DH10B (i) and subjected to colony PCR with BMP9-specific primers (ii). (C) Packaging of AdROS-mBMP9 in 293pTP cells. At the indicated time points, RFP signal was also recorded. Comet-like adenovirus-producing foci were apparent at 5 days after transfection. Representative images are shown. Both RFP and bright field images were also recorded at a lower magnification (4x) (FIG. 8B). (D) Transduction efficiency of AdROS-mBMP9 in mesenchymal stem cells. Subconfluent imBMSC cells were infected with the indicated titers of AdROS-mBMP9, and RFP signal was recorded at 36 h post infection. Representative images are shown. MOI, multiplicity of infection, indicating # of infectious adenoviruses per cell.

FIGS. 5A-C demonstrate that adenovirus-mediated BMP9 transgene expression induces osteogenic differentiation of mesenchymal stem cells (MSCs). (A) Adenovirus-mediated expression of BMP9 effectively induces osteogenic marker alkaline phosphatase (ALP) in MSCs. Mouse imBMSCs were infected with AdROS-mBMP9 or Ad-RFP. At the indicated time points, the ALP activities of the infected cells were assessed histochemically (i) and quantitatively (ii). "*" $p<0.01$, compared with respective RFP group. (B) Adenovirus-mediated expression of BMP9 effectively induces matrix mineralization in MSCs. AdROSmBMP9 or Ad-RFP infected imBMSCs were cultured in mineralization medium and subjected to Alizarin Red S staining at the indicated time points. Representative results are shown. (C) Adenovirus-mediated expression of BMP9 effectively induces ectopic bone formation in MSCs. Subconfluent imBMSCs were infected with AdROS-mBMP9 or Ad-RFP (i). The infected cells were collected and injected subcutaneously into athymic nude mice. While no masses were formed in the Ad-RFP group, bony masses were retrieved from the AdROS-mBMP9 group at 4 weeks after implantation and subjected to H&E staining (ii) and Masson's trichrome staining (iii). Representative results are shown.

FIG. 6 is a vector map of the pAdGOSd vector, a destination vector for Gibson assembly-mediated one-step construction of recombinant adenovirus. The pAdGOSd vector co-expresses eGFP marker.

FIG. 7 is a vector map of the pAdROSd vector, a destination vector for Gibson assembly-mediated one-step construction of recombinant adenovirus. The pAdROSd vector co-expresses mRFP marker.

Figures 8A, 8B:
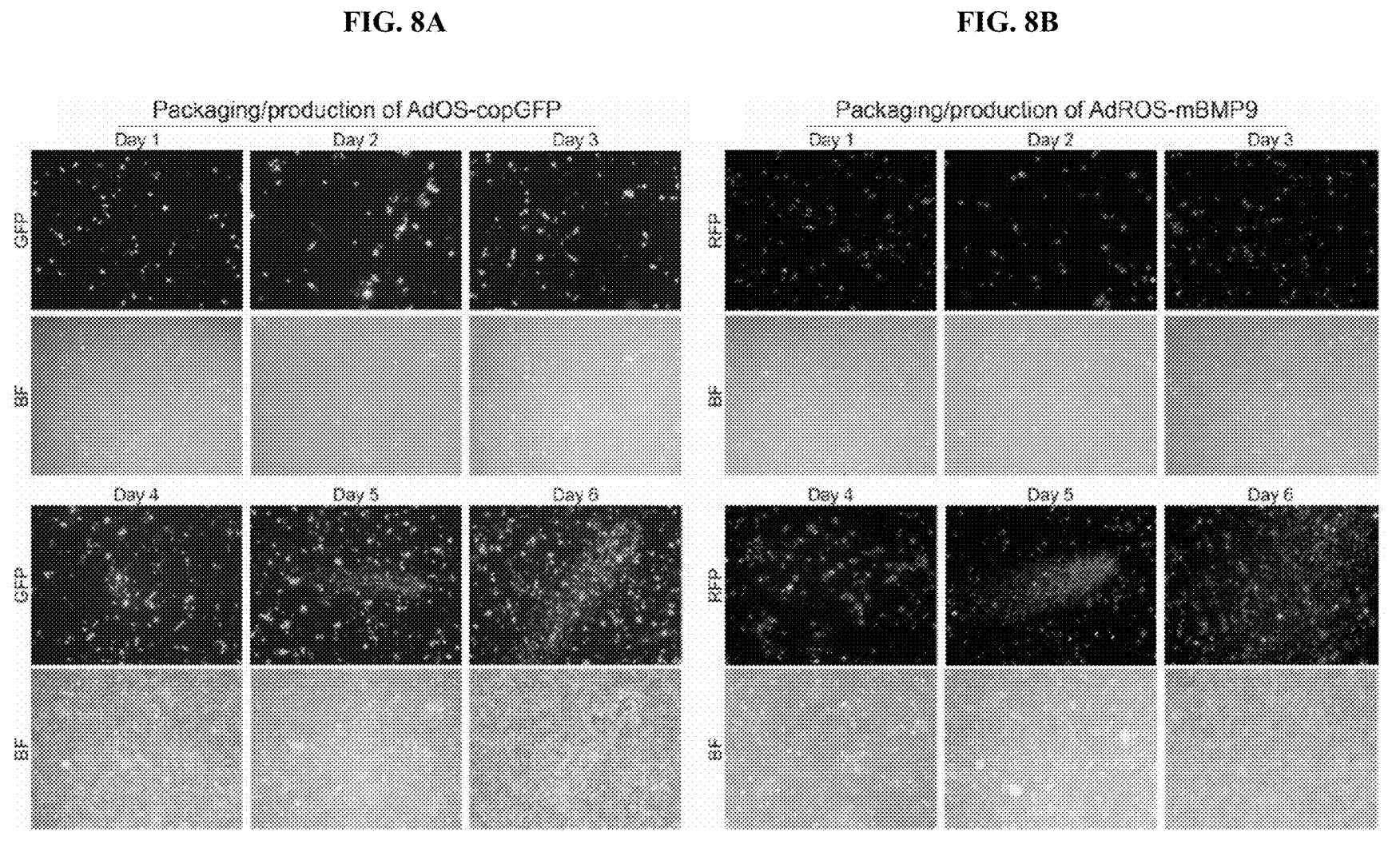
Figure 1A:
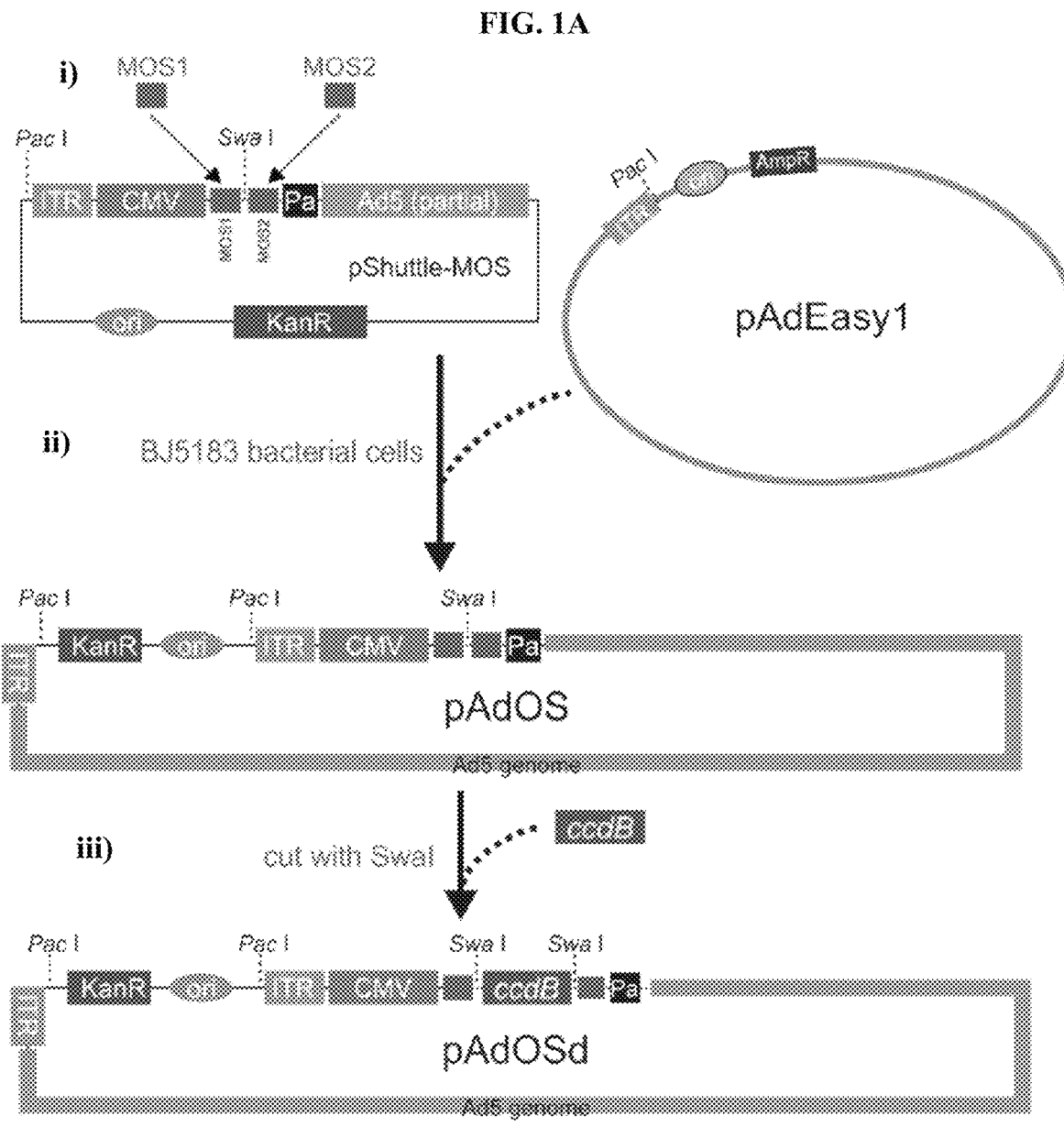

FIG. 8A-B shows packaging and production of recombinant adenoviruses generated from the Gibson Assembly technology. (A) The initial production of AdOS-copGFP virus in 293pTP cells. At the indicated time points, both GFP and bright field (BF) images were recorded at lower magnification (4x). Comet-like images were apparent at 5 days after transfection. Representative images are shown. (B) The initial production of AdROS-mBMP9 virus in 293pTP cells. At the indicated time points, both RFP and bright field (BF) images were recorded at lower magnification (4x). Comet-like images were apparent at 5 days after transfection. Representative images are shown.

DETAILED DESCRIPTION

The present disclosure is predicated, at least in part, on the development of a simplified system and method for constructing adenoviral vectors using Gibson DNA Assembly (GDA). In some embodiments, the disclosure provides adenoviral recipient vectors that contain two unique 20-base pair (bp) cloning nucleic acid sequences that serve as universal overlapping sites for Gibson Assembly reactions at a deleted E1 region of the adenovirus genome. In other embodiments, the recipient adenoviral vectors further comprise a bacterial suicide gene located between the cloning nucleic acid sequences to reduce cloning background.

Gene Transfer Vector

The disclosure provides a gene transfer vector comprising (i) all or part of a viral genome and (ii) a suicide gene flanked by a first cloning nucleic acid sequence and a second cloning nucleic acid sequence, wherein the first and second cloning nucleic acid sequences are different. The term "gene transfer vector," as used herein, refers to a vehicle used to deliver foreign genetic material to a cell, where it can be replicated and/or expressed. Gene transfer vectors ideally enter a wide variety of cell types, have the capacity to accept large nucleic acid sequences, are safe, and can be produced in quantities required for treating patients. Any gene transfer vector can be employed in the present disclosure, including viral and non-viral gene transfer vectors. Examples of suitable viral gene transfer vectors include, but are not limited to, retroviral vectors, adeno-associated virus vectors, vaccinia virus vectors, herpesvirus vectors, parainfluenza-RSV chimeric vectors (PIV-RSV), and adenoviral vectors. Examples of suitable non-viral vectors include, but are not limited to, plasmids, liposomes, and molecular conjugates (e.g., transferrin).

In some embodiments, the gene transfer vector is a viral vector, which comprises all or part of a viral genome. For example, the gene transfer vector may comprise all or part of an adenovirus genome, which is referred to as an "adenoviral vector." Adenovirus is a medium-sized (90-100 nm), nonenveloped icosahedral virus containing approximately 36 kilobases (kb) of double-stranded DNA. The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., *Fields Virology,* 5th ed., Knipe et al. (eds.), Lippincott Williams & Wilkins, Philadelphia, Pa. (2006)). The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

Several features of adenoviruses make them ideal vehicles for transferring genetic material to cells for therapeutic applications (e.g., gene therapy, immunotherapy, or as vaccines). For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.,* 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

The adenovirus capsid mediates the key interactions of the early stages of the infection of a cell by the virus and is required for packaging adenovirus genomes at the end of the adenovirus life cycle. The capsid comprises 252 capsomeres, which includes 240 hexon trimers, 12 penton base pentamer proteins, and 12 trimer fibers (Ginsberg et al., *Virology,* 28: 782-83 (1966)). The hexon comprises three identical proteins, namely polypeptide II (Roberts et al., *Science,* 232: 1148-51 (1986)). The penton base comprises five identical proteins and the fiber comprises three identical proteins. Proteins Ma, VI, and IX are present in the adenoviral coat and are believed to stabilize the viral capsid (Stewart et al., *Cell,* 67: 145-54 (1991), and Stewart et al., *EMBO J.,* 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

The adenoviral vector may be of any serotype or combination of serotypes. Over 50 serotypes of adenovirus have been identified, which are classified as subgroup A (e.g., serotypes 12, 18, and 31), subgroup B (e.g., serotypes 3, 7, 11, 14, 16, 21, 34, 35, 50, and 55), subgroup C (e.g., serotypes 1, 2, 5, and 6), subgroup D (e.g., serotypes 8, 9, 10, 13, 15, 17, 19, 20, 22-30, 32, 33, 36-39, and 42-49, 51, 53, 54, 56), subgroup E (e.g., serotype 4), subgroup F (e.g., serotypes 40 and 41), subgroup G (e.g., serotype 52). Various serotypes of adenovirus are available from the American Type Culture Collection (ATCC, Manassas, Va.). In one embodiment, the adenovirus or adenoviral vector is a serotype 5 adenovirus or adenoviral vector ("Ad5").

The adenoviral vector can be replication-deficient or conditionally replication-competent. An adenoviral vector that is "replication-competent" can replicate in typical host cells, i.e., cells typically capable of being infected by an adenovirus. In contrast, a "replication-deficient" or "replication-incompetent" adenoviral vector requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A "conditionally-replicating" adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific promoter. In such embodiments, replication requires the presence or absence of specific factors that activate or repress the promoter. Conditionally-replicating adenoviral vectors are further described in, e.g., U.S. Pat. Nos. 5,998, 205 and 6,824,771.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

The early region 1A and 1B (E1A and E1B) genes encode proteins required for a productive adenovirus lytic cycle (Fields, supra). E1A is the first viral gene transcribed after infection and produces two related proteins, 243R and 289R, which induce transcription of the other early viral gene regions and stimulate infected cells to enter S-phase of the cell cycle. The E1B region encodes two major proteins, E1B19K and E1B55K. The E1B55K protein binds the cellular tumor suppressor p53 and can block p53-mediated apoptosis and inhibition of viral and cellular replication. The E1B19K protein is a Bcl-2 homologue that interacts with Bax and inhibits apoptosis, allowing the virus to replicate longer (Sundararajan, R. and White, E, J. Virology, 75:7506-7516 (2001)). The E1A proteins have been shown to induce S-phase in infected cells by associating with p300/CBP or the retinoblastoma (Rb) protein (Howe et al., Proc. Natl. Acad. Sci. USA, 87: 5883-5887 (1990); Wang et al., Mol. Cell. Biol., 11: 4253-4265 (1991); Howe, J. A. and Bayley, S. T. Virology, 186: 15-24 (1992)). Rb and p300 regulate the activity of E2F transcription factors, which coordinate the expression of cellular genes required for cell cycle progression (Helin, K., Curr. Opin. Genet. Dev., 8: 28-35 (1998)). Thus, E1A gene products play a role in viral genome replication by driving entry of quiescent cells into the cell cycle, in part, by displacing E2F transcription factors from the retinoblastoma protein (pRb) tumor suppressor (Liu, X. and Marmorstein, R., Genes & Dev., 21: 2711-2716 (2007)).

In some embodiments, the adenoviral vector may comprise a deletion, in whole or in part, of one or more regions of the adenoviral genome. In some embodiments, the adenoviral vector comprises a deletion of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. For the purpose of providing sufficient space in the adenoviral genome for one or more non-native nucleic acid sequences (or "transgenes"), removal of a majority of one or more gene regions may be desirable. In this regard, the adenovirus or adenoviral vector may comprise a deletion of all or part of any of the adenoviral early regions (e.g., E1, E2, E3 and E4 regions), the late regions (e.g., the L1, L2, L3, L4, and L5 regions), genes involved in viral packaging (e.g., the IVa2 gene), and/or virus-associated RNAs (e.g., VA-RNA-1 and/or VA-RNA-2). In one embodiment, the adenoviral vector comprises a deletion of all or part of the E1A region, a deletion of all or part of the E1B region of the adenoviral genome, a deletion of all or part of the E3 region of the adenoviral genome, and/or a deletion of all or part of the E4 region of the adenoviral genome. The size of the deletion may be tailored so as to retain an adenoviral vector whose genome closely matches the optimum genome packaging size. A larger deletion will accommodate the insertion of larger non-native nucleic acid sequences in the adenoviral genome.

First-generation adenoviral vectors ("Ad vectors") are deficient in the E1 region (i.e., E1A and E1B) and E3 region, with an initial transgene cloning capacity of 5.2 kb (1). Second-generation Ad vectors are deficient in more non-structural genes (e.g., E2/E4) in addition to the E1 and E3 regions, leading to increased cloning capacity and decreased cytotoxicity, although these Ad vectors require distinct packaging cells for viral production (1). Third-generation Ad vectors (also known as high-capacity adenoviral vectors (HC-AdVs), gutless AdVs, or helper-dependent AdVs (HD-AdVs)) are deficient in all viral coding sequences, containing only 5' and 3' ITRs and the packaging signal, thus providing a larger capacity for transgenic cloning sequences (36 kb) (1). While HCAdVs offer many benefits with significantly minimized cytotoxicity, their production depends on the presence of a helper adenovirus genome provided in trans, which often compromises virus quantities.

By removing all or part of certain regions of the adenoviral genome, for example, the E1B, E3, and/or E4 regions of the adenoviral genome, the resulting adenoviral vector is able to accept inserts of exogenous non-native nucleic acid sequences while retaining the ability to be packaged into adenoviral capsids. Thus, in another embodiment, the adenoviral vector comprises one or more non-native nucleic acid sequences. A non-native nucleic acid sequence can be inserted at any position in the adenoviral genome so long as insertion allows for the formation of adenovirus or the adenoviral vector particle. A "non-native" nucleic acid sequence is any nucleic acid sequence (e.g., DNA, RNA, or cDNA sequence) that is not a naturally occurring nucleic acid sequence of an adenovirus in a naturally occurring position. The terms "non-native nucleic acid sequence," "heterologous nucleic acid sequence," and "exogenous nucleic acid sequence" are synonymous and can be used interchangeably in the context of the present disclosure. The non-native nucleic acid sequence preferably is DNA and preferably encodes a protein (e.g., one or more nucleic acid sequences encoding one or more proteins). The term "transgene" is defined herein as a non-native nucleic acid sequence that is operably linked to appropriate regulatory elements (e.g., a promoter), such that the non-native nucleic acid sequence can be expressed to produce an RNA or protein (e.g., a regulatory RNA sequence, peptide, or polypeptide). The regulatory elements (e.g., promoter) can be native or non-native to the adenovirus or adenoviral vector.

To facilitate selection of vectors containing a transgene or gene of interest (GOI), the gene transfer vector further comprises a suicide gene. The term "suicide gene," as used herein, refers to a gene whose expression is lethal to a cell in which it is expressed. While an understanding of a mechanism is not needed to practice the present disclosure and while the disclosure is not limited to any particular mechanism, the presence of a suicide gene in the gene transfer vector allows for the selection of cells in which the suicide gene is replaced by a transgene of interest during vector construction, which is an indication of successful vector production. In other words, the presence of the suicide gene allows for selection against vectors that do not incorporate the transgene of interest. Any suitable suicide gene may be incorporated into the gene transfer vector. Suitable suicide genes include, but are not limited to, the cytosine deaminase gene (CD) of *Escherichia coli*, the herpes simplex virus thymidine kinase gene (HSV-tk), and the bacterial suicide gene ccdB. In some embodiments, the suicide gene is a ccdB gene.

In nature, the ccdB gene is located on the F sex factor plasmid of *E. coli* and is part of a toxin-antitoxin system encoded by the ccd operon, which is responsible for plasmid maintenance during cell division. ccdB codes for a toxic protein (CcdB) that acts as a DNA gyrase poison, locking up DNA gyrase with broken double stranded DNA and ultimately causing cell death. The ccdB gene has been used as a positive selection gene in recombinant DNA and molecular cloning methodologies for over 25 years (see, e.g., Bernard, P., Biotechniques, 21(2): 320-3 (1996); Bahassi et al., Mol Microbiol., 15(6): 1031-7 (1995); and Bernard et al., Gene, 148(1):71-4 (1994)).

In some embodiments, the suicide gene is flanked by a first cloning nucleic acid sequence and a second cloning nucleic acid sequence to facilitate vector construction and transgene cloning. The first cloning nucleic acid sequence and second cloning nucleic acid sequence desirably are different. Each of the first and second cloning nucleic acid sequences may be of any suitable size. For example, each of the first and second cloning nucleic acid sequences may be greater than five nucleotides (e.g., 6, 7, 8, 9, or 10 nucleotides), but desirably less than 30 nucleotides (e.g., 29, 25, or 20 nucleotides). In some embodiments, each of the first and second cloning nucleic acid sequences comprises about 15-25 nucleotides (e.g., 16, 17, 18, 19, 20, 21, 22, 23, or 24 nucleotides). In other embodiments, each of the first and second cloning nucleic acid sequences comprises about 20 nucleotides. An exemplary first cloning nucleic acid sequence comprises SEQ ID NO: 1 (AATCG-GAAAGCGGACGCGGA), and an exemplary second cloning nucleic acid sequence comprises SEQ ID NO: 2 (CGAGTATCCCGTGAGCGCTT). The disclosure is not limited to these particular cloning nucleic acid sequences, however.

Compositions

The disclosure further provides a composition comprising the gene transfer vector (e.g., an adenoviral vector) described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the gene transfer vector. Any suitable carrier can be used within the context of the disclosure, and such carriers are well known in the art. The choice of carrier will be determined, in part, by the particular use of the composition (e.g., administration to an animal) and the particular method used to administer the composition. In some embodiments, the pharmaceutical composition can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the gene transfer vector is part of a composition formulated to protect the gene transfer vector from damage prior to administration. For example, the composition can be formulated to reduce loss of the gene transfer vector on devices used to prepare, store, or administer the adenoviral vector, such as glassware, syringes, or needles. The composition can be formulated to decrease the light sensitivity and/or temperature sensitivity of the gene transfer vector. For example, when the gene transfer vector is an adenoviral vector, the composition may comprise a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector and facilitate its administration. Formulations for adenoviral vector-containing compositions are further described in, for example, U.S. Pat. Nos. 6,225,289, 6,514,943, 7,456,009, 7,888,096; 10,272,032 and International Patent Application Publication WO 2000/034444.

Systems and Methods for Producing Adenoviral Vectors

The disclosure further provides systems and methods for producing an adenoviral vector. In some embodiments, the system comprises (a) a destination vector comprising (i) all or part of an adenoviral genome and (ii) a suicide gene flanked by a first cloning nucleic acid sequence and a second cloning nucleic acid sequence, wherein the first and second cloning nucleic acid sequences are different; (b) a transgene comprising a nucleic acid sequence flanked the first cloning nucleic acid sequence and the second cloning nucleic acid sequence; and (c) reagents for Gibson DNA Assembly (GDA). The destination vector may comprise all or a part of an adenoviral genome, as described herein. For example, the destination vector may be an adenoviral vector of any serotype (such as serotype 5) comprising a deletion of the E1 region, and optionally deletions in other early and/or late region genes. Descriptions of the suicide gene, first and second cloning nucleic acid sequences, transgene, and components thereof set forth above in connection with the gene transfer vector also are applicable to those same aspects of the aforementioned system and method.

Gibson DNA Assembly (GDA), named after its developer Daniel G. Gibson (14), is a synthetic biology technique that allows the one-step isothermal DNA assembly of multiple overlapping fragments in a restriction enzyme-free, seamless, and sequence-independent fashion. A typical GDA in vitro recombination system contains three essential isothermal enzymes: 5'-exonuclease to remove nucleotides from the ends of double-stranded DNA molecules and expose complementary single-stranded DNA (ssDNA) overhangs for specific annealing; DNA polymerase to fill in the ssDNA gaps of the joined molecules; and DNA ligase to covalently seal the nicks (15). The GDA method is a useful molecular engineering tool to construct synthetic and natural genes, genetic pathways, and entire genomes (14-16). The GDA method also has been used to generate adenoviral vectors (see, e.g., Pan et al., Viruses 2018 Oct. 18; 10(10):568. doi: 10.3390/v10100568; Zou et al., J Virol Methods 2018 July; 257:85-92. doi: 10.1016/j.jviromet.2018.04.001; Miciak et al., PLoS ONE 13(6): e0199563 (2018). doi.org/10.1371/journal.pone.0199563; and Hamdan et al., Molecular Therapy: Methods & Clinical Development, 20: P625-634 (2021)). Reagents for Gibson DNA Assembly include, but are not limited to 5'-exonucleases (e.g., T5 exonuclease), DNA polymerases (e.g., Phusion DNA polymerase), DNA ligases (e.g., Taq DNA ligase), host cells (e.g., competent *E. coli* cells), and cell culture media.

The disclosure also provides a method of producing an adenoviral vector comprising contacting a cell with the above-described system. Recombinant adenoviral vectors typically are generated using one of four different approaches. The first method developed involves homologous recombination between a shuttle vector and an backbone adenovirus genome vector in packaging cells such as HEK-293 cells (1, 6), but suffers from extremely low efficiency. An alternative technique is the direct ligation of transgene-containing fragments to a linearized E1/E3-deleted adenoviral genome DNA fragment using several restriction enzymes, such as ClaI, I-CeuI, SwaI and PI-SceI engineered in the E1 deletion region (7). This ligation approach, however, is rarely used due to low efficiency and the recombinant virus often requires purification from contaminating wild-type transgene-null Ad viruses. A third approach involves the use of site-specific recombinase and transposase systems, such as the CRE/LOX and FLIP/FRT recombinases and the GATEWAY® transposon system, to insert transgenes into the E1 deletion region at specific recipient sites (8, 9). However, these systems are extensively commercialized with high cost and lack of technical transparency, which limits their widespread use. The fourth approach involves taking advantage of more efficient homologous recombination in microorganisms, such as bacteria and yeast, to generate transgene-containing adenoviral vectors (10-13). An example of such a system is the AdEasy system, which has become one of the most commonly used techniques worldwide to generate Ad vectors (1, 2, 12, 13). An essential component of the AdEasy system is the RecA$^+$ *E. coli* strain BJ5183, which exhibits a high rate of homologous recombination but allows for the generation of stable large recombinants (1, 12, 13). BJ5183 cells, however, exhibit a relatively low transformation efficiency compared with conventional strains used for molecular cloning, which poses technical challenges to researchers. Certain components of the AdEasy system may be used in the connection with the disclosed system and method. Methods for the production and purification of adenoviruses and adenoviral vectors are described in, e.g., U.S. Pat. No. 6,194,191, and International Patent Application Publications WO 99/54441, WO 98/22588, WO 98/00524, WO 96/27677, and WO 2003/078592.

Production of adenoviral vectors also may involve the use of complementing cell lines. The term "complementing cell lines," as used herein, refers to cell lines that provide gene functions not present in a replication-deficient adenoviral vector, but required for viral propagation, at appropriate levels in order to generate high titers of viral vector stock. Such complementing cell lines are known and include, but are not limited to, 293 cells (described in, e.g., Graham et al., J. Gen. Virol., 36: 59-72 (1977)) and PER.C6 cells (described in, e.g., International Patent Application Publication WO 1997/000326, and U.S. Pat. Nos. 5,994,128 and 6,033,908). It has been shown that overexpression of serotype 5 adenovirus precursor terminal protein (pTP) alone, or in combination with E1A overexpression, in HEK-293-based cells, namely 293pTP and RAPA cell lines, respectively, accelerates Ad packaging and amplification processes (17, 18). Thus, in some embodiments, the above described system may be introduced into cells that overexpress pTP and/or E1A. In some instances, one or more replication-essential gene functions lacking in a replication-deficient adenoviral vector can be supplied by a helper virus, e.g., an adenoviral vector that supplies in trans one or more essential gene functions required for replication of the replication-deficient adenoviral vector.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The following examples further illustrate the invention but, of course, should not be construed as in any way limiting its scope.

EXAMPLES

The following materials and methods were used in the experiments described in the Examples.

Cell Culture, Enzymes and Chemicals

Human HEK-293 derivative lines 293pTP and RAPA cells were used for adenovirus packaging and amplification as previously described (17, 18). Mouse bone marrow-derived mesenchymal stem cells imBMSCs were previously characterized (19). All cells were maintained in DMEM supplemented with 10% fetal bovine serum (FBS, Gemini Bio-Products), 100 U/ml penicillin, and 100 µg/ml streptomycin at 37° C. in 5% $CO_2$ as described previously (20-22). All restriction endonucleases, and the Gibson Assembly Master Mix or the NEBUILDER® HiFi DNA Assembly kit were purchased from New England Biolabs (NEB, Ipswich, MA). Unless indicated otherwise, other chemicals were purchased from ThermoFisher Scientific (Waltham, MA) or Millipore Sigma (St. Louis, MO).

Construction of the Adenoviral Backbone-Containing GDA Recipient Vectors pAdOSd, pAdROSd, and pAdGOSd The CMV-PA expression cassette of the pShuttle-CMV, pAdTrack-CMV, or pAdTrace-CMV shuttle vectors used in the AdEasy system (1, 12, 13, 23) were first modified by inserting a SwaI restriction site flanked with two unique 20-bp sequences MOS1 and MOS2, resulting in the pShuttle-MOS vector (from pShuttle-CMV). This vector was linearized with PmeI and subjected to homologous recombination reactions in pAdEasy1-containing BJ5183 bacterial cells. The kanamycin-resistant colonies were grown up and verified by PCR and restriction digestion to generate the pAdOS vector.

In order to reduce the background of GDA reactions, the bacterial suicide gene ccdB expression cassette was PCR amplified with both primers anchored with SwaI sites, ligated into the SwaI-digested pAdOS vector, and transformed into competent DB3.1 bacterial cells. Bacterial colonies were PCR screened, and positive candidate clones were grown up and further verified by PCR, restriction digestions, and DNA sequencing. The resultant GDA recipient vector was designated pAdOSd. Similar recipient vectors were also constructed from pAdTrack-CMV and pAdTrace-CMV shuttle vectors, and designated pAdGOSd and pAdROSd, respectively. All oligo sequences are listed in Table 1. The vector maps and sequences for pAdGOSd and pAdROSd are shown in FIG. 6 and FIG. 7. All cloning and assembly junctions were verified by DNA sequencing.

TABLE 1

| Gene/ Oligo Name | Sequence | Use |
| --- | --- | --- |
| MOS1/2 cassette | GatccAATCGGAAAGCGGACGCGGAatt taaatCGAGTATCCCGTGAGCGCTTt (SEQ ID NO: 3) CtagaAAGCGCTCACGGGATACTCGatt taaatTCCGCGTCCGCTTTCCGATTg (SEQ ID NO: 4) | cloning |
| copGFP Forward | AATCGGAAAGCGGACGCGGAatttacca ccATGGAGAGCGACGACAGCGGCCATG (SEQ ID NO: 5) | GDA |
| copGFP Reverse | AAGCGCTCACGGGATACTCGatttAG CGAGATCCGGTGGAGCCGGG (SEQ ID NO: 6) | |
| mouse BMP9 Forward | AATCGGAAAGCGGACGCGGAatttacca ccatgggcATGCATATGTCCCCTGGGGC CTTC (SEQ ID NO: 7) | |
| mouse BMP9 Reverse | AAGCGCTCACGGGATACTCGatttct acctacacccacactcagccacac (SEQ ID NO: 8) | |
| MOSO1F | AATCGGAAAGCGGACGCGGAattt (SEQ ID NO: 9) | colony PCR |
| MOSO2R | AAGCGCTCACGGGATACTCGattt (SEQ ID NO: 10) | |

Gibson DNA Assembly (GDA) Reactions

The GDA reactions were carried out by using the Gibson Assembly Master Mix or NEBUILDER® HiFi DNA Assembly kit from NEB as described (24). The coding region for the gene of interest (GOI, see below) was PCR amplified using the PHUSION® High-Fidelity PCR kit. Each assembly reaction (usually in 10-15 µl reaction volume) contained approximately 100 ng of insert DNA and 50 ng of the SwaI-linearized pAdOSd, pAdGOSd, or pAdROSd vector, and incubated at 50° C. for 40-60 minutes. After the assembly reaction was completed, the reaction mix was briefly digested with SwaI and transformed into electro-competent DH10B cells. Colony PCR screening was carried out using primers specific for the GOI. Positive clones were further sequencing verified.

Generation and Amplification of Recombinant Adenoviruses Expressing copGFP, and Mouse BMP9 (mBMP9) Using OSCA The coding sequences for copGFP and mouse BMP9 were PCR amplified with forward primers anchored with the MOS1 and kozak sequences and reverse primers anchored with the MOS2 sequence (Table 1). The PCR fragments were gel purified and used for GDA reactions. Positive candidate clones were screened by colony PCR and validated by restriction digestions and DNA sequencing. The resultant recombinant adenovirus plasmids were designated pAdOS-copGFP and pAdROS-mBMP9, respectively.

For making recombinant adenoviruses, these plasmids were first linearized with Pad to liberate adenoviral inverted terminal repeat (ITR) sequences at both ends, and then transfected into 293pTP or RAPA cells as described (17, 18). Apparent adenovirus packaging and production were obtained at 5-7 days after transfection. Adenoviral lysates were prepared by multiple cycles of freeze-thaw as described (13, 23). High titer adenoviruses were obtained through repeated infections of HEK-293, 293pTP, or RAPA cells, and the resultant adenoviruses were designated as AdOS-copGFP and AdROSmBMP9, respectively. Analogous adenovirus expressing only RFP (Ad-RFP) was used as a control (25-29). For the adenoviral infections, polybrene (4-8 µg/ml) was added to enhance infection efficiency as previously reported (30).

Qualitative and Quantitative Assays of Alkaline Phosphatase (ALP) Activity

ALP activity was assessed quantitatively with a modified assay using the GREAT ESCAPE™ SEAP Chemiluminescence assay kit (BD Clontech, Mountain View, CA) and qualitatively with a histochemical staining assay (using a mixture of 0.1 mg/ml napthol AS-MX phosphate and 0.6 mg/ml Fast Blue BB salt), as previously described (31-34). Each assay condition was performed in triplicate and the results were repeated in at least three independent experiments.

Ectopic Bone Formation

All animal studies were conducted by following the guidelines approved by the Institutional Animal Care and Use Committee (IACUC) of The University of Chicago. Stem cell-mediated ectopic bone formation was performed as described (28, 35, 36). Briefly, subconfluent imBMSC cells were infected with AdROS-mBMP9 or Ad-RFP for 16 hours, collected, and resuspended in PBS for subcutaneous injection ($5 \times 10^6$/injection) into the flanks of athymic nude mice (5/group, 4-6 wk old, female, ENVIGO, Indianapolis, IN). At four weeks after implantation, animals were sacrificed, and the implantation sites were retrieved for histologic evaluation and Trichrome staining as described below.

Histological Analysis and Trichrome Staining

Retrieved tissues were fixed, decalcified in 10% buffered formalin, and embedded in paraffin. Serial sections of the embedded specimens were stained with hematoxylin and eosin (H & E). Trichrome staining was carried out as previously described (37-41).

Statistical Analysis

Quantitative ALP assays were performed in triplicate. Data were expressed as mean±SD. Statistical significances were determined by one-way analysis of variance and the student's t test. A value of $p < 0.05$ was considered statistically significant.

Example 1

This example describes the development of destination vectors for the one-step construction of adenovirus (OSCA) system using GDA technology.

To develop a panel of adenoviral vectors that can serve as common recipients for GDA reactions, three of the first-generation adenoviral shuttle vectors of the AdEasy system (12, 13) were modified (i.e., pShuttle-CMV, pAdTrack-CMV and pAdTrace-CMV), by inserting an oligo cassette that contains a SwaI site flanked by two unique 20-bp sequences, namely MOS1 and MOS2 (FIG. 1A, panel i), to generate pShuttle-MOS, pAdTrack-MOS, and pAdTrace-MOS vectors. These plasmids were linearized with PmeI and transformed into BJ5183/pAdEasy1 bacterial cells for homologous recombination (FIG. 1A, panel b). The kanamycin-resistant clones were picked up and subsequently confirmed by PCR and sequencing, resulting in pAdOS, pAdGOS, and pAdROS vectors.

To reduce potential background in GDA reactions, the above vectors were further modified by inserting the suicide gene ccdB expression cassette flanked with SwaI sites through GDA reactions, and grown in DB3.1 bacterial cells, resulting in the OSCA destination/recipient vectors, pAdOSd, pAdGOSd and pAdROSd (FIG. 1A, panel iii). The vector maps and full-length sequences for pAdGOSd and pAdROSd are presented in FIG. 6 and FIG. 7.

Figure 1B:
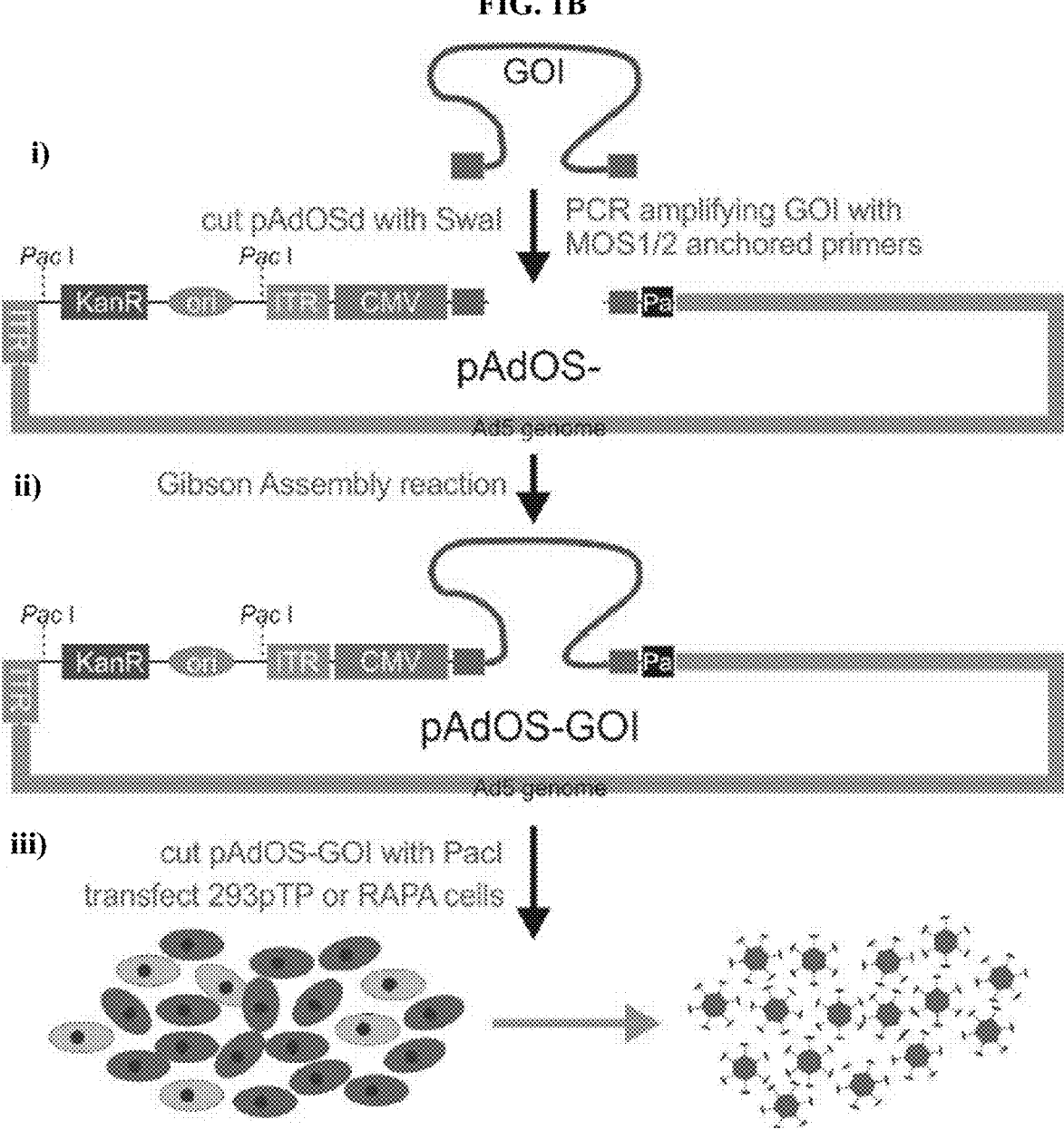

The practical use of the GDA-based one-step construction of adenovirus (OSCA) system for transgene expression is illustrated in FIG. 1B. Briefly, the MOS1 and MOS2-anchored primers were used to amplify the coding region of the gene of interest (GOI) (FIG. 1B, panel i). The resulting PCR fragment was gel purified, and mixed with the SwaI-linearized destination vector, such as pAdOSd, pAdGOSd or pAdROSd, for GDA reactions to generate the GOI-containing recombinant adenoviral plasmid, pAdOS-GOI (FIG. 1B, panel ii). This recombinant adenoviral plasmid was digested with PacI and then transfected into optimized adenovirus packaging cells, such as 293pTP and RAPA, as described (17, 18), leading to robust adenovirus packaging and production in 5-7 days (FIG. 1B, panel iii). The initial adenoviral lysate can be further amplified in HEK-293, 293pTP or RAPA cells to attain high titers for in vitro or in vivo use.

Example 2

This example demonstrates the generation of a copGFP-expressing adenoviral vector using the system described herein.

Figure 2A:
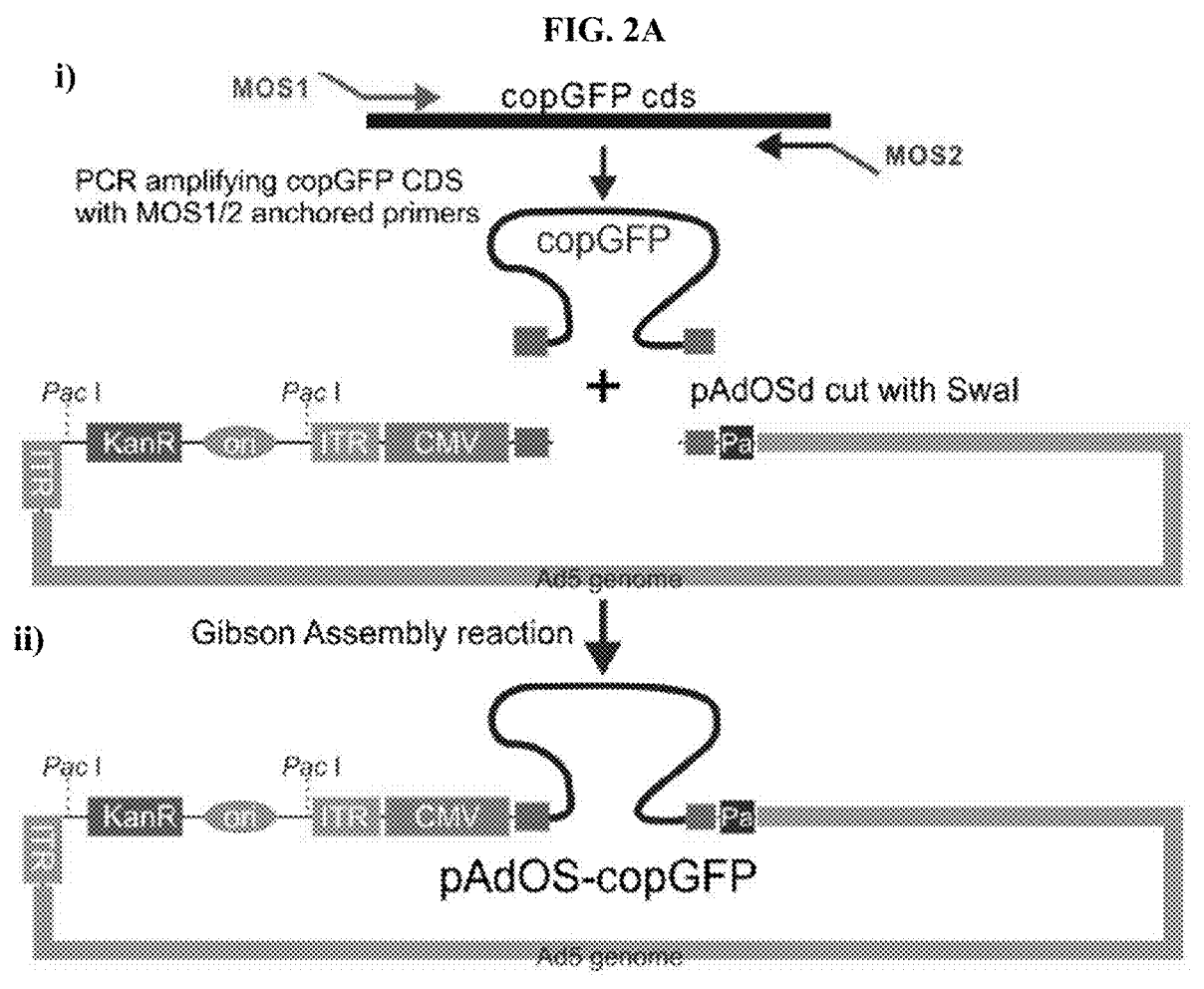

To carry out a proof-of-principle experiment, we the OSCA system described herein was used to make an adenoviral vector expressing the marker gene copGFP. The coding sequence of copGFP was amplified with MOS1 and MOS2 anchored primers, and the amplified fragment was purified (FIG. 2A, panels i & ii), yielding adenoviral plasmid pAdOS-copGFP.

Figures 2B, 2C:
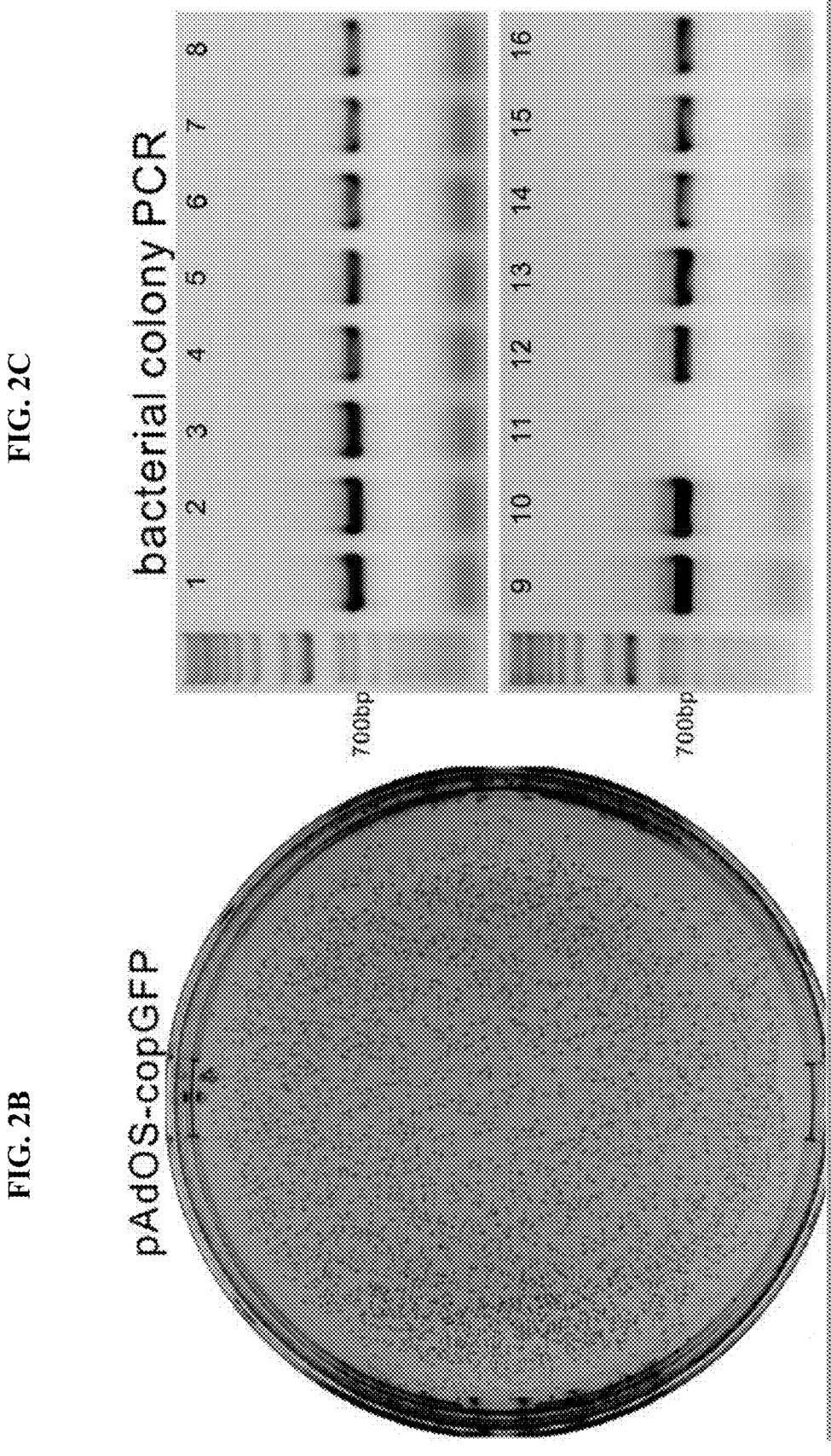

Using the NEBUILDER® HiFi DNA Assembly kit, it was found that the GDA reactions were in general very efficient as ~10% of the assembly products yielded nearly thousands of colonies after direct plating (FIG. 2B). PCR screening of randomly picked up clones indicated that 15 of 16 were positive for the presence of copGFP transgene (FIG. 2C). To further verify the structural integrity of adenoviral genome of the pAdOS-copGFP plasmids generated from the Gibson Assembly reactions, we digested the representative clones, in comparison with the adenoviral backbone vector pAdEasy1, with four restriction enzymes, Hind III (FIG. 2D, panel i), Kpn I (FIG. 2D, panel b), Barn HI (FIG. 2D, panel c), and Sph I (FIG. 2D, panel iv). The restriction digestion results indicated that all three selected clones yielded the same and expected digestion patterns (FIG. 2D). The assembled junctions were further verified by DNA sequencing. Collectively, these results demonstrate that the OSCA system is effective for GDA-based rapid construction of recombinant adenovirus plasmids.

Figures 3A, 3B:
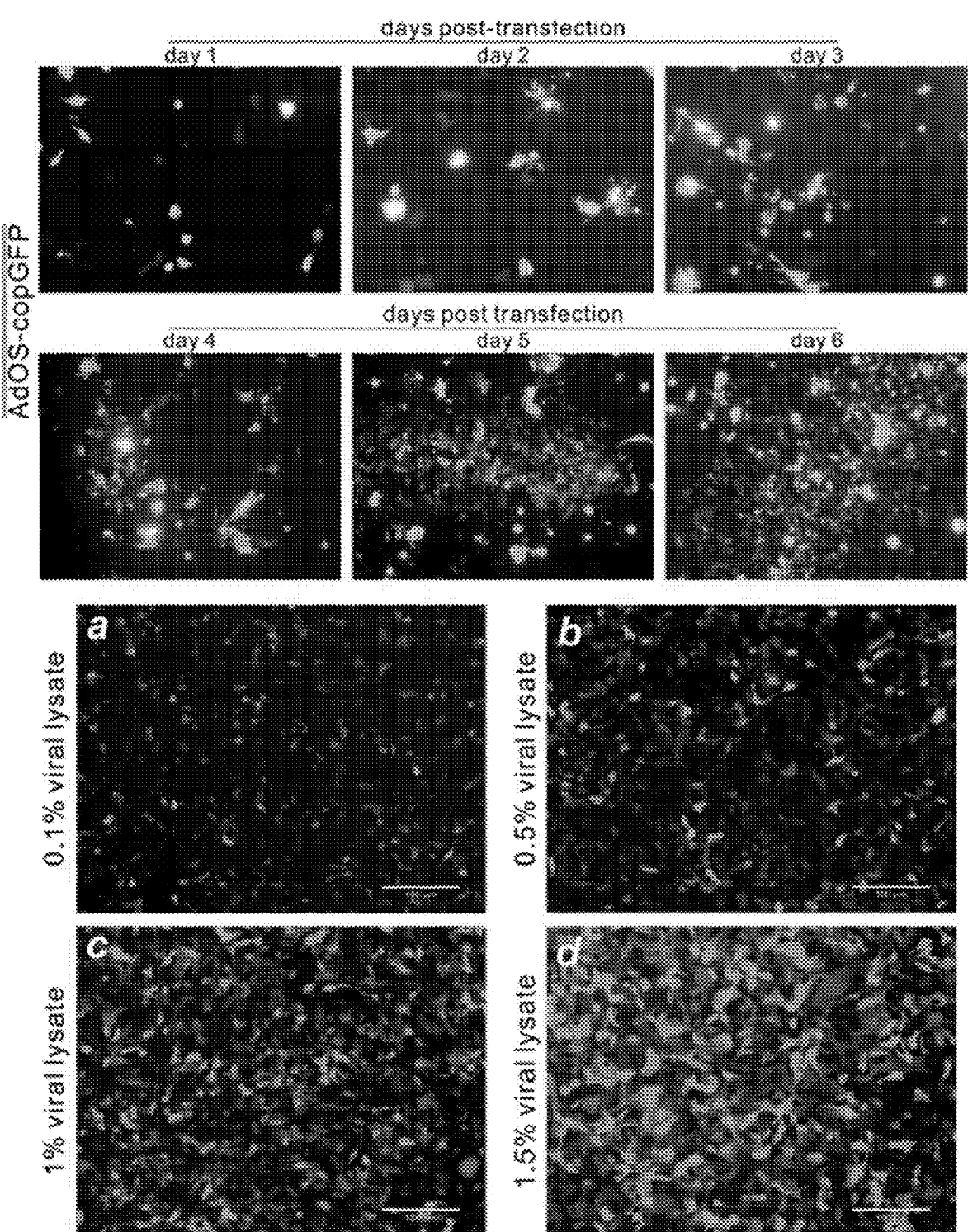

It was next tested whether the pAdOS-copGFP plasmid could be effectively packaged into adenovirus. The pAdOS-copGFP plasmid was first linearized with PacI restriction enzyme, and then transfected into 293pTP cells (or RAPA cells, data not shown). While the transfection efficiency was modest, the GFP signal became increasingly intensified, and formed comet-like foci at 4 days after transfection, becoming apparent at day 7, which was also the endpoint of the adenovirus packaging (FIG. 3A). When the viral lysate was prepared at 7 days after transfection, HEK-293 cells were infected with different titers (as measured by % of the collected viral lysate) and demonstrated that significant copGFP expression was observed in a dose-dependent manner and was detected at levels as low as 0.1% of viral lysate (FIG. 3B, panels a-d).

These results indicate that the adenovirus production system described herein is highly efficient for construction of recombinant adenoviruses.

Example 3

This example demonstrates the high osteogenic activity of mouse BMP9 expressed by an adenoviral vector generated using the system described herein.

The biological functionality of OSCA-produced adenovirus was demonstrated by constructing the adenoviral vector AdROS-mBMP9 to express mouse BMP9 (mBMP9). Human BMP9 is one of the most osteogenic factors in promoting bone formation from mesenchymal stem cells (MSCs) (42-45). However, virtually no studies have been carried out to investigate the osteogenic activity of mouse BMP9 (mBMP9). Here, the coding region of mBMP9 was amplified with MOS1 and MOS2 anchored primers, and the adenoviral vector pAdROS-mBMP9 was generated using the OSCA system (FIG. 4A).

Figures 4A, 4B:
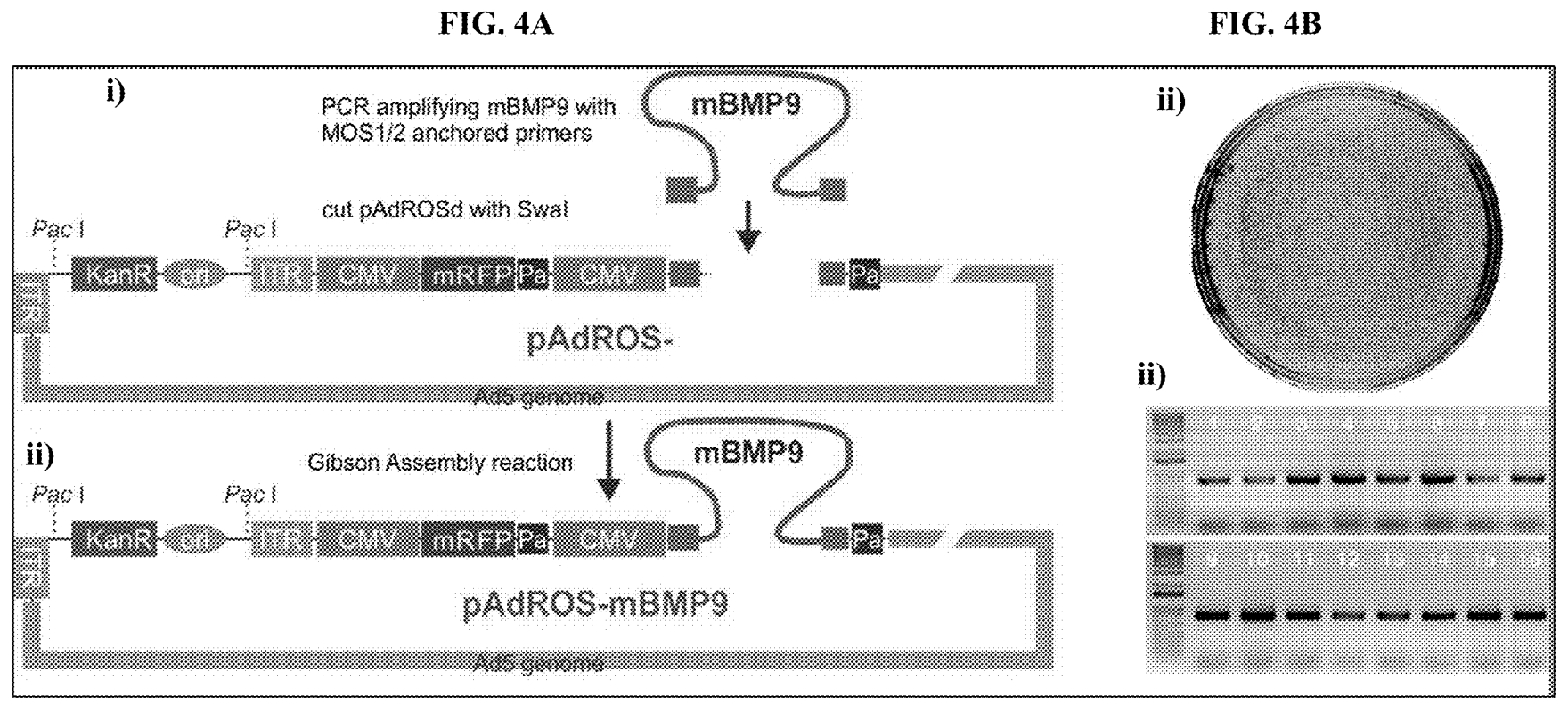
Figures 4C, 4D:
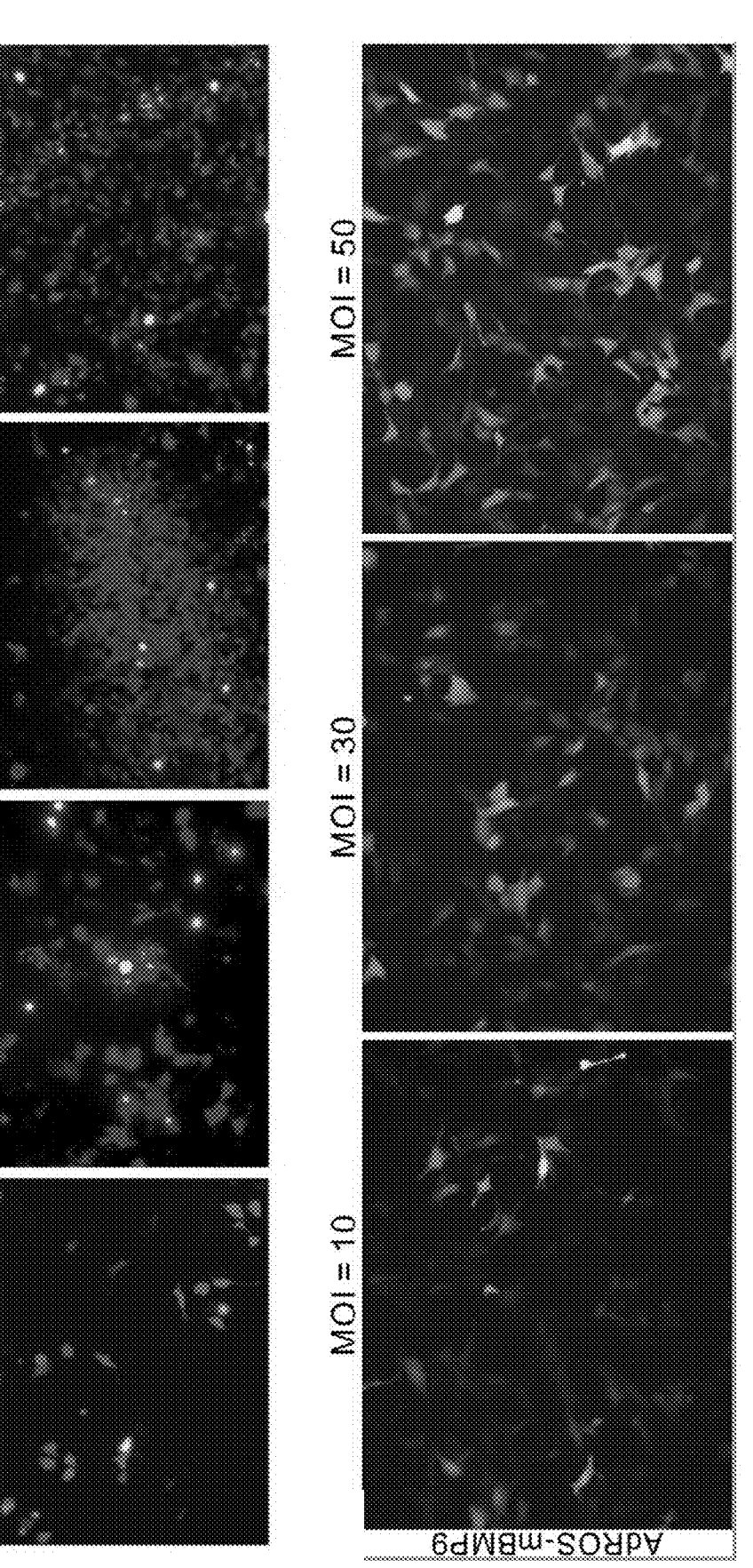

Consistent with the results shown in FIG. 2B-2D, the GDA reactions were effective and generated a high percentage of positive clones (FIG. 4B). Furthermore, the Pac linearized pAdROS-mBMP9 was shown to generate adenovirus with high efficiency in packaging cells (FIG. 4C and FIG. 8B). The generated AdROS-mBMP9 virus was shown to effectively transduce imBMSC MSCs in a titer-dependent fashion (FIG. 4D).

Figure 5A:
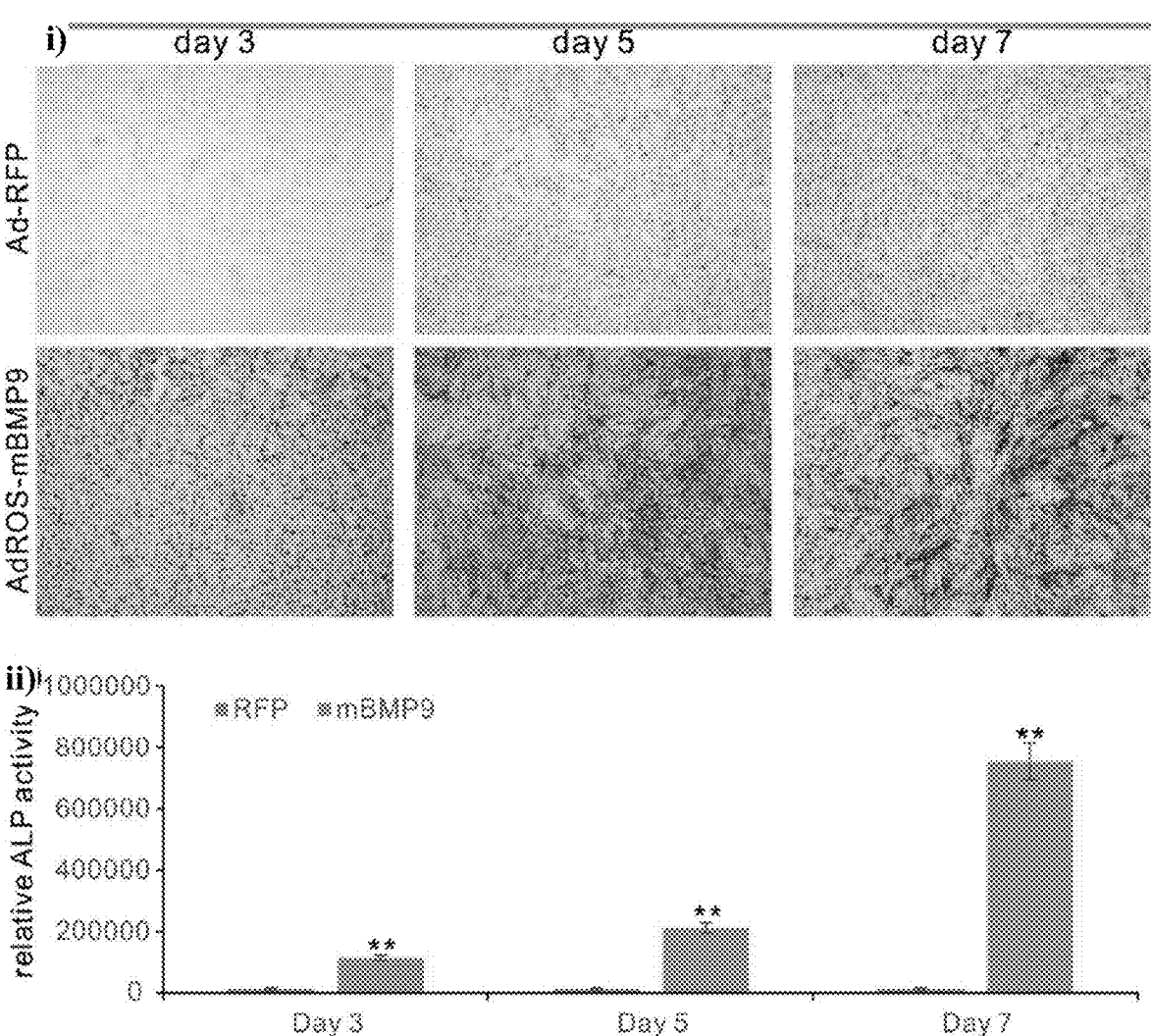
Figures 5B, 5C:
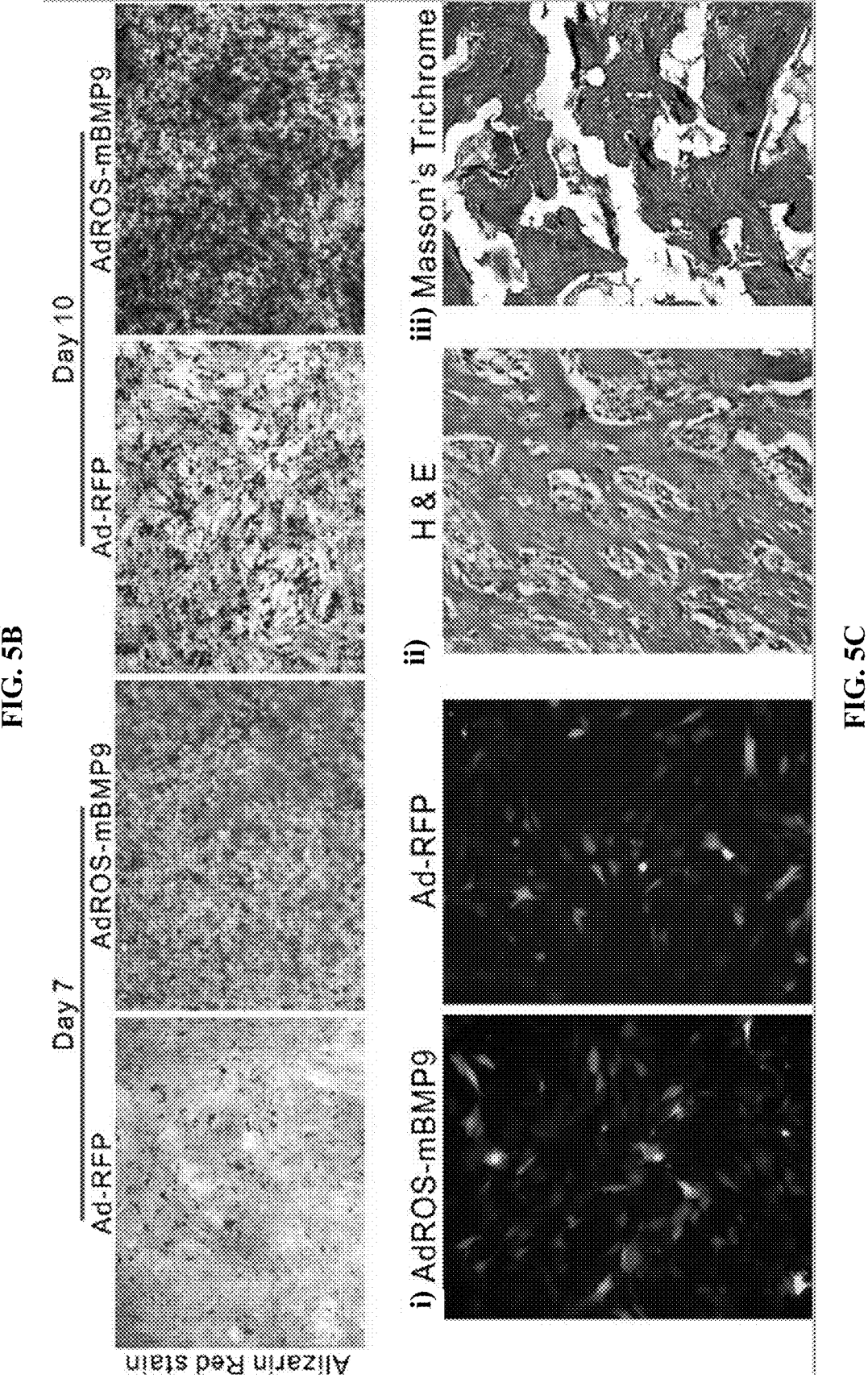

To test the biological function of mouse BMP9, the imBMSCs were infected with AdROSmBMP9 and control Ad-RFP viruses. mBMP9 effectively induced alkaline phosphatase (ALP) activities in a time-course dependent fashion, compared with that of the control Ad-RFP group (FIG. 5A), indicating that adenovirus-mediated expression of mouse BMP9 was able to induce early osteogenic marker ALP in MSCs. Furthermore, the adenovirus-mediated mouse BMP9 expression was shown to induce matrix mineralization (FIG. 5B). When the MSCs were infected with AdROS-mBMP9 or Ad-RFP (FIG. 5C, panel i), collected and injected subcutaneously into the athymic nude mice, robust bone formation was detected in the mBMP9 group, but not in the RFP control group, at 4 weeks after implantation as assessed by H & E staining (FIG. 5C, panel ii). Trichrome staining further revealed that mouse BMP9 induced robust trabecular bone formation with highly mineralized bone matrix (FIG. 5C, panel iii). Collectively, these results demonstrate that mBMP9 can be included in an adenoviral vector produced as described herein, and the resultant adenovirus can effectively transduce MSCs to induce osteogenic differentiation.

Sequences
Nucleic acid sequence of the pAdGOSd vector.

(SEQ ID NO: 11)

```
nnttaattaaggatccnnncctgtcctcgaccgatgcccttgagagccttcaacccagtcagctccttccg gtgggcgcggggcatgactatcgtcgccgcacttatgactgtc ttctttatcatgcaactcgtaggacaggtgccggcagcgctctgggtcattttcggcga ggaccgctttcgctggagcgcgacgatgatcggcctgtcgcttgcggtattcgga atcttgcacgccctcgctcaagccttcgtcactggtcccgccaccaaacgtttcggcgagaa gcaggccattatcgccggcatggcggccgacgcgctgggctacgtcttgc tggcgttcgcgacgcgaggctggatggccttccccattatgattcttctcgct tccggcggcatcgggatgcccgcgttgcaggccatgctgtccaggcaggtagatgacgac catcagggacagcttcaaggatcgctcgcggctcttaccagcctaacttcgatcactgg accgctgatcgtcacggcgatttatgccgcctcggcgagcacatggaacgggtt ggcatggattgtaggcgccgccctataccttgtctgcctccccgcgttgcgtcgcgg tgcatggagccgggccacctcgacctgaatggaagccggcggcacctcgctaac ggattcaccactccaagaattggagccaatcaattcttgcggagaactgtgaatgcgcaaaccaacccttggc agaacatatccatcgcgtccgccatctccagcagccgca cgcggcgcatctcgggcagcgttgggtcctggccacgggtgcgcatgatcgtgctcct gtcgttgaggacccggctaggctggcggggttgccttactggttagcagaatg
```

-continued

```
aatcaccgatacgcgagcgaacgtgaagcgactgctgctgcaaaacgtctgcgacctgagcaacaa catgaatggtcttcggtttccgtgtttcgtaaagtctggaaacgcgg aagtcagcgccctgcaccattatgttccggatctgcatcgcaggatgctgctggctacc ctgtggaacacctacatctgtattaacgaagcgctggcattgaccctgagtgatttt tctctggtcccgccgcatccataccgccagttgtttaccctcacaacgttccagtaaccgggcat gttcatcatcagtaacccgtatcgtgagcatcctctctcgtttcatcggta tcattaccccccatgaacagaaattccccccttacacggaggcatcaagtgaccaaacaggaaa aaaccgcccttaacatggcccgctttatcagaagccagacattaacgcttctg gagaaactcaacgagctggacgcggatgaacaggcagacatctgtgaatcgcttcacgacca cgctgatgagctttaccgcagctgcctcgcgcgtttcggtgatgacggt gaaaacctctgacacatgcagctcccggagacggtcacagcttgtctgtaagcggatgccggg agcagacaagcccgtcagggcgcgtcagcgggtgttggcgggtgtc ggggcgcagccatgacccagtcacgtagcgatagcggagtgtatactggcttaactatgcggcatca gagcagattgtactgagagtgcaccatatgcggtgtgaaataccg cacagatgcgtaaggagaaaataccgcatcaggcgctcttccgcttcctcgctcactgactcgc tgcgctcggtcgttcggctgcggcgagcggtatcagctcactcaaagg cggtaatacggttatccacagaatcaggggataacgcaggaaagaacatgtgagcaaaaggccag caaaaggccaggaaccgtaaaaaggccgcgttgctggcgtttttc cataggctccgcccccctgacgagcatcacaaaaatcgacgctcaagtcagaggtggcg aaacccgacaggactataaagataccaggcgtttccccctggaagctccctc gtgcgctctcctgttccgaccctgccgcttaccggatacctgtccgcctttc tcccttcgggaagcgtggcgctttctcaatgctcacgctgtaggtatctcagttcggtgtaggtc gttcgctccaagctgggctgtgtgcacgaaccccccgttcagcccgaccgctgcgccttatccggta actatcgtcttgagtccaacccggtaagacacgacttatcgccact ggcagcagccactggtaacaggattagcagagcgaggtatgtaggcggtgctacaga gttcttgaagtggtggcctaactacggctacactagaaggacagtatttggtatct gcgctctgctgaagccagttaccttcggaaaaagagttggtagctcttgatccggcaaacaaaccaccg ctggtagcggtggtttttttgtttgcaagcagcagattacgcgca gaaaaaaaggatctcaagaagatcctttgatctttttctacggggtctgacgctcagtggaacgaaaa ctcacgttaagggattttggtcatgagattatcaaaaaggatcttcacc tagatccttttaaattaaaaatgaagttttaaatcaatctaaagtatatatgagtaaacttggtct gacagttaccaatgcttaatcagtgaggcacctatctcagcgatctgtctat ttcgttcatccatagttgcctgactccccgtcgtgtagataactacgatacgggagggcttacca tctggccccagtgctgcaatgataccgcgagacccacgctcaccggctcca gatttatcagcaataaaccagccagccggaagggccgagcgcagaagtggtcctgcaactttt atccgcctccatccagtctattaattgttgccgggaagctagagtaagtagt tcgccagttaatagtttgcgcaacgttgttgnnaaaaaggatcttcacctagatccttttc acgtagaaagccagtccgcagaaacggtgctgaccccggatgaatgtcagcta ctgggctatctggacaagggaaaacgcaagcgcaaagagaaagcaggtagcttgcagtggg cttacatggcgatagctagactgggcggttttatggacagcaagcgaac cggaattgccagctggggcgccctctggtaaggttgggaagccctgcaaagtaaactggatggct
```

-continued

```
ttctcgccgccaaggatctgatggcgcaggggatcaagctctgatc aagagacaggatgaggatcgtttcgcatgattgaacaagatggattgcacgcaggttctcc ggccgcttgggtggagaggctattcggctatgactgggcacaacagacaat cggctgctctgatgccgccgtgttccggctgtcagcgcaggggcgcccggttcttttgtc aagaccgacctgtccggtgccctgaatgaactgcaagacgaggcagcgcg gctatcgtggctggccacgacgggcgttccttgcgcagctgtgctcgacgttgtcactgaagcggg aagggactggctgctattgggcgaagtgccggggcaggatctcct gtcatctccccttgctcctgccgagaaagtatccatcatggctgatgcaatgcggcggctg catacgcttgatccggctacctgcccattcgaccaccaagcgaaacatcgcat cgagcgagcacgtactcggatggaagccggtcttgtcgatcaggatgatctggacgaagagcatc aggggctcgcgccagccgaactgttcgccaggctcaaggcgagc atgcccgacggcgaggatctcgtcgtgacccatggcgatgcctgcttgccgaatatcatggtgga aaatggccgcttttctggattcatcgactgtggccggctgggtgtggc ggaccgctatcaggacatagcgttggctacccgtgatattgctgaagagcttggcggcgaatg ggctgaccgcttcctcgtgctttacggtatcgccgctcccgattcgcagc gcatcgccttctatcgccttcttgacgagttcttctgaattttgttaaaatttttgttaaat cagctcattttttaaccaataggccgaaatcggcaacatcccttataaatcaaaag aatagaccgcgatagggttgagtgttgttccagtttggaacaagagtccactattaaagaa cgtggactccaacgtcaaagggcgaaaaaccgtctatcagggcgatggcccacta cgtgaaccatcacccaaatcaagttttttgcggtcgaggtgccgtaaagctctaaatcggaa ccctaaagggagcccccgatttagagcttgacggggaaagccggcgaac gtggcgagaaaggaagggaagaaagcgaaaggagcgggcgctagggcgctggcaagt gtagcggtcacgctgcgcgtaaccaccacacccgcgcgcttaatgcgcc gnnttaattaannnntcccttccagctctctgcccctttttggattgaagccaatatgataatgaggg ggtggagtttgtgacgtggcgcggggcgtgggaacggggcgggtg acgtagtagtgtggcggaagtgtgatgttgcaagtgtggcggaacacatgtaagcgac ggatgtggcaaaagtgacgtttttggtgtgcgccggtgtacacaggaagtgaca attttcgcgcggtttaggcggatgttgtagtaaatttgggcgtaaccgagtaa gatttggccattttcgcgggaaaactgaataagaggaagtgaaatctgaataattttgtgttac tcatagcgcgtaannncgcgttaagatacattgatgagtttggacaaaccacaactag aatgcagtgaaaaaatgctttatttgtgaaatttgtgatgctattgctttatttgtaacc attataagctgcaataaacaagttaacaacaacaattgcattcattttatgtttcagg ttcaggggggaggtgtgggaggtttttttaaagcaagtaaaacctctacaaatgtggtatgg ctgattatgatcagttatctagatccggtggatctgagtccggacttgtacagctcgtc catgccgagagtgatcccggcggcggtcacgaactccagcaggaccatgtgatc gcgcttctcgttggggtctttgctcagggcggactgggtgctcaggtagtggttgtcgg gcagcagcacgggccgtcgccgatggggtgttctgctggtagtggtcggcg agctgcacgctgccgtcctcgatgttgtggcggatcttgaagttcaccttgatgccgttcttctgcttg tcggccatgatatagacgttgtggctgttgtagttgtactccagcttgtg ccccaggatgttgccgtcctccttgaagtcgatgcccttcagctcgatgcggttcaccagggtgtcgccc
```

-continued tcgaacttcacctcggcgcgggtcttgtagttgccgtcgtccttg aagaagatggtgcgctcctggacgtagccttcgggcatggcggacttgaagaagtcgtg ctgcttcatgtggtcggggtagcggctgaagcactgcacgccgtaggtcagg gtggtcacgagggtgggccagggcacgggcagcttgccggtggtgcagatgaacttcagggt cagcttgccgtaggtggcatcgccctcgccctcgccggacacgctga acttgtggccgtttacgtcgccgtccagctcgaccaggatgggcaccaccccggtgaacagct cctcgcccttgctcaccatggtggcgaccggtagcgctagcggatctga cggttcactaaaccagctctgcttatatagacctcccaccgtacacgcctaccgcccatttgc gtcaatggggcggagttgttacgacattttggaaagtcccgttgattttggtgc caaaacaaactcccattgacgtcaatggggtggagacttggaaatccccgtgagtc aaaccgctatccacgcccattgatgtactgccaaaaccgcatcaccatggtaatagc gatgactaatacgtagatgtactgccaagtaggaaagtcccataaggtcatgtactg ggcataatgccaggcgggccatttaccgtcattgacgtcaatagggggcgtacttg gcatatgatacacttgatgtactgccaagtgggcagtttaccgtaaatactccacccattgacgt caatggaaagtccctattggcgttactatgggaacatacgtcattattgacg tcaatgggcgggggtcgttgggcggtcagccaggcgggccatttaccgtaagttatgtaa cgcggaactccatatatgggctatgaactaatgacccccgtaattgattactatta nnnctagcagatcctggttctttccgcctcagaagccatagagcccaccgcatcccagcatgcctg ctattgtcttcccaatcctccccccttgctgtcctgccccacccaccc cccagaatagaatgacacctactcagacaatgcgatgcaatttcctcattttatta ggaaaggacagtgggagtggcaccttccagggtcaaggaaggcacggggggaggg caaacaacagatggctggcaactagaaggcacagtcgaggctgatcagcgggtttagcgg ccgatatcatttaaattgattttgcggtataagaatatatactgatatgtatacc cgaagtatgtcaaaaagaggtatgctatgaagcagcgtattacagtgacagttgacagcgac agctatcagttgctcaaggcatatatgatgtcaatatctccggtctggtaagc acaaccatgcagaatgaagcccgtcgtctgcgtgccgaacgctggaaagcggaaaatcagg aagggatggctgaggtcgcccggtttattgaaatgaacggctcttttgctg acgagaacaggggctggtgaaatgcagtttaaggtttacacctataaaagagagagccgtta tcgtctgtttgtggatgtacagagtgatattattgacacgcccgggcgacgg atggtgatcccctggccagtgcacgtctgctgtcagataaagtctcccgtgaactttacccggtggtgcatatcgggga tgaaagctggcgcatgatgaccaccgatatggccagtgtgccggtctccgttatcggggaagaagtggctgatctcagc caccgcgaaaatgacatcaaaaacgccattaacctgatgttctggggaatataaatgtcaggctccct tatacacagccagtctgcagctcgctcttcatttaaatcctgaattcggtgtcttctatggaggtcaaaacagc gtggatggcgtctccaggcgatctgacggttcactaaacagc tcgatctctatcactgatagggagatctctatcactgatagggagatctctatcactgatagggat gatctctatcactgatagggagagctctgcttatatagacctcccaccgtac acgcctaccgcccatttgcgtcaatggggcggagttgttacgacattttggaaagtcccgttgattttggttcca aaacaaactcccattgacgtcaatggggtggagacttgga aatccccgtgagtcaaaccgctatccacgcccattgatgtactgccaaaaccgcatcaccatggtaatagcga tgactaatacgtagatgtactgccaagtaggaaagtcccat aaggtcatgtactgggcataatgccaggcgggccatttaccgtcattgacgtcaataggg -continued

```
ggcgtacttggcatatgatacacttgatgtactgccaagtgggcagtttaccgta aatactccacccattgacgtcaatggaaagtccctattggcgttactatgggaacatacgtcattattgacgtcaat gggcgggggtcgttgggcggtcagccaggcgggcca tttaccgtaagttatgtaacgcggaactccatatatgggctatgaactaatgaccccgtaattgattac tattaataactagagnnnntaagggtgggaaagaatatataaggtgg gggtcttatgtagttttgtatctgttttgcagcagccgccgccgccatgagcaccaactcgtttgatggaag cattgtgagctcatatttgacaacgcgcatgcccccatgggccg gggtgcgtcagaatgtgatgggctccagcattgatggtcgccccgtcctgcccgcaaactct actaccttgacctacgagaccgtgtctggaacgccgttggagactgcagc ctccgccgccgcttcagccgctgcagccaccgcccgcg ggattgtgactgactttgctttcctgagcccgcttgcaagcagtgcagcttcccgttcatccgcccgcgatgaca agttgacggctcttttggcacaattggattctttgacccgggaacttaatgtcgtttctcagcagctgttggat ctgcgccagcaggtttctgccctgaaggcttcctcccctcccaa tgcggtttaaaacataaataaaaaaccagactctgtttggatttggatcaagcaagtgtcttgctgtctt tatttaggggtttttgcgcgcgcggtaggcccgggaccagcggtctc ggtcgttgagggtcctgtgtatttttttccaggacgtggtaaaggtgactctggatgttcagatacatgg gcataagcccgtctctggggtggaggtagcaccactgcagagcttc atgctgcggggtggtgttgtagatgatccagtcgtagcaggagcgctgggcgtggtgcctaaaaatgtcttt cagtagcaagctgattgccaggggcaggcccttggtgtaag tgtttacaaagcggttaagctgggatgggtgcatacgtggggatatgagatgcatcttgg actgtattttttaggttggctatgttcccagccatatccctccggggattcatgttgtg cagaaccaccagcacagtgtatccggtgcacttgggaaatttgtcatgtagcttagaag gaaatgcgtggaagaacttggagacgcccttgtgacctccaagattttccatgca ttcgtccataatgatggcaatgggcccacgggcggcggcctgggcgaagat atttctgggatcactaacgtcatagttgtgttccaggatgagatcgtcataggccatttttaca aagcgcgggcggagggtgccagactgcggtataatggttccatccggcccaggggc gtagttaccctcacagatttgcatttcccacgctttgagttcagatgggggggatcat gtctacctgcggggcgatgaagaaaacggtttccggggtaggggagatcagctgggaa gaaagcaggttcctgagcagctgcgacttaccgcagccggtgggcccgtaa atcacacctattaccgggtgcaactggtagttaagagagctgcagctgc cgtcatccctgagcagggggggccacttcgttaagcatgtccctgactcgcatgtttttccctgacc aaatccgccagaaggcgctcgccgcccagcgatagcagttcttgcaagg aagcaaagttttcaacggtttgagaccgtccgccgtaggcatgcttttgagcgtttgaccaag cagttccaggcggtcccacagctcggtcacctgctctacggcatctcgatccagcat atctcctcgtttcgcgggttggggcggctttcgctgtacggcagtagtcggtgctcg tccagacgggccagggtcatgtctttccacgggcgcagggtcctcgtcagcgtagtctgggtcacggt gaaggggtgcgctccgggctgcgcgctggccagggtgcgctt gaggctggtcctgctggtgctgaagcgctgccggtcttcgccctgcgcgtcggccagg tagcatttgaccatggtgtcatagtccagcccctccgcggcgtggccccttggcg cgcagcttgcccttggaggaggcgccgcacgaggggcagtgcagactttttgagggcgtag
```

-continued agcttgggcgcgagaaataccgattccggggagtaggcatccgcgccg caggccccgcagacggtctcgcattccacgagccaggtgagctctggccgttcggggtc aaaaaccaggtttcccccatgcttttttgatgcgtttcttacctctggtttccatga gccggtgtccacgctcggtgacgaaaaggctgtccgtgtccccgtatacagacttgagaggcc tgtcctcgagcggtgttccgcggtcctcctcgtatagaaactcggacca ctctgagacaaaggctcgcgtccaggccagcacgaaggaggctaagtgggaggggtagcgg tcgttgtccactaggggggtccactcgctccagggtgtgaagacacatg tcgccctcttcggcatcaaggaaggtgattggtttgtaggtgtaggccacgtgaccgggtg ttcctgaagggggggctataaaaggggggtggggggcgcgttcgtcctcactctc ttccgcatcgctgtctgcgagggccagctgttggggtgagtactccctctgaaaagcgggca tgacttctgcgctaagattgtcagtttccaaaaacgaggaggatttgatattc acctggcccgcggtgatgcctttgagggtggccgcatccatctggtcagaaaagacaatcttttt tgttgtcaagcttggtggcaaacgacccgtagagggcgttggacagcaa cttggcgatggagcgcagggtttggtttttgtcgcgatcggcgcgctccttggccgcg atgtttagctgcacgtattcgcgcgcaacgcaccgccattcgggaaagacggtgg tgcgctcgtcgggcaccaggtgcacgcgccaaccgcggttgtgcagggtgacaaggtcaacgctgg tggctacctctccgcgtaggcgctcgttggtccagcagaggcg gccgcccttgcgcgagcagaatggcggtaggggggtctagctgcgtctcgtccgggggggtctgcgtc cacggtaaagaccccgggcagcaggcgcgcgtcgaagtagtct atcttgcatccttgcaagtctagcgcctgctgccatgcgcgggcggcaagcgcgcgctcgtat gggttgagtgggggaccccatggcatggggtgggtgagcgcggaggc gtacatgccgcaaatgtcgtaaacgtagaggggctctctgagtattccaagatatgtagggtagca tcttccaccgcggatgctggcgcgcacgtaatcgtatagttcgtgcga gggagcgaggaggtcgggaccgaggttgctacgggcgggctgctctgctcggaagactatc tgcctgaagatggcatgtgagttggatgatatggttggacgctggaaga cgttgaagctggcgtctgtgagacctaccgcgtcacgcacgaaggaggcgtaggagtcgcgcagcttg ttgaccagctcggcggtgacctgcacgtctagggcgcagtag tccagggtttccttgatgatgtcatacttatcctgtccctttttttttccacagctcgcggttga ggacaaactcttcgcggtctttccagtactcttggatcggaaacccgtcggc ctccgaacggtaagagcctagcatgtagaactggttgacggcctggtaggcgcagcatccc ttttctacgggtagcgcgtatgcctgcgcggccttccggagcgaggtgtgggt gagcgcaaaggtgtccctgaccatgactttgaggtactggtatttgaagtcagtgtcgtcg catccgccctgctcccagagcaaaaagtccgtgcgctttttggaacgcggattt ggcagggcgaaggtgacatcgttgaagagtatctttcccgcgcgaggcataaagttgcgtgtgatgcggaagggt cccggcacctcggaacggttgttaattacctgggcg gcgagcacgatctcgtcaaagccgttgatgttgtggcccacaatgtaaagttccaagaagcg cgggatgcccttgatggaaggcaatttttttaagttcctcgtaggtgagctctt caggggagctgagcccgtgctctgaaagggcccagtctgcaagatgagggttggaagcgacgaatgagctcca caggtcacgggccattagcatttgcaggtggtcgcg aaaggtcctaaactggcgacctatggccatttttttctggggtgatgcagtagaaggtaagcgggtcttgttcccagc ggtcccatccaaggttcgcggctaggtctcgcgcgg -continued cagtcactagaggctcatctccgccgaacttcatgaccagcatgaagggcacgagctgcttcccaaaggcccccat ccaagtataggtctctacatcgtaggtgacaaagag acgctcggtgcgaggatgcgagccgatcgggaagaactggatctcccgccaccaattggaggagt ggctattgatgtggtgaaagtagaagtccctgcgacgggccgaac actcgtgctggcttttgtaaaaacgtgcgcagtactggcagcggtgcacgggctgtacatcctgcacgagg ttgacctgacgaccgcgcacaaggaagcagagtgggaattt gagcccctcgcctggcgggtttggctggtggtcttctacttcggctgcttgtccttgaccgtctggctgctcgag gggagttacggtggatcggaccaccacgccgcgcgagc ccaaagtccagatgtccgcgcgcggcggtcggagcttgatgacaacatcgcgcagatgggagctgtcca tggtctggagctcccgcggcgtcaggtcaggcgggagctc ctgcaggtttacctcgcatagacgggtcagggcgcgggctagatccaggtgatacctaatttccaggggctgg ttggtggcggcgtcgatggcttgcaagaggccgcatcc ccgcggcgcgactacggtaccgcgcggcgggcggtgggccgcggggtgtccttggatgatgcatctaaaa gcggtgacgcgggcgagcccccggaggtaggggggg gctccggacccgccgggagagggggcaggggcacgtcggcgccgcgcgcgggcaggagctggtgctgcgcgcgta ggttgctggcgaacgcgacgacgcggcggt tgatctcctgaatctggcgcctctgcgtgaagacgacgggcccggtgagcttgagcctgaaagagagttcg acagaatcaatttcggtgtcgttgacggcggcctggcgcaa aatctcctgcacgtctcctgagttgtcttgataggcgatctcggccatgaactgctcgatctcttcctcct ggagatctccgcgtccggctcgctccacggtggcggcgaggtcg ttggaaatgcgggccatgagctgcgagaaggcgttgaggcctccctcgttccagacgcggctgtagaccac gcccccttcggcatcgcgggcgcgcatgaccacctgcgc gagattgagctccacgtgccgggcgaagacggcgtagtttcgcaggcgctgaaagaggtagttgagggtgg tggcggtgtgttctgccacgaagaagtacataacccagc gtcgcaacgtggattcgttgatatcccccaaggcctcaaggcgctccatggcctcgtagaagtccacggcgaag ttgaaaaactgggagttgcgcgccgacacggttaactc ctcctccagaagacggatgagctcggcgacagtgtcgcgcacctcgcgctcaaaggctacaggggc ctcttcttcttcttcaatctcctcttccataagggcctccccttcttctt cttctggcggcggtgggggaggggggacacggcggcgacgacggcgcaccgggaggcggtcgacaaagcg ctcgatcatctccccgcggcgacggcgcatggtctc ggtgacggcgcggccgttctcgcggggggcgcagtggaagacgccgcccgtcatgtcccggttatgggttggc gggggctgccatgcggcagggatacggcgctaac gatgcatctcaacaattgttgtgtaggtactccgccgccgagggacctgagcgagtccgcatcg accggatcggaaaacctctcgagaaaggcgtctaaccagtcacagtc gcaaggtaggctgagcaccgtggcgggcggcagcgggcggcggtcggggttgtttctggcgg aggtgctgctgatgatgtaattaaagtaggcggtcttgagacggcgg atggtcgacagaagcaccatgtccttgggtccggcctgctgaatgcgcaggcggtcggccatgccccaggct tcgttttgacatcggcgcaggtctttgtagtagtcttgcatg agcctttctaccggcacttcttcttctccttcctcttgtcctgcatctcttgcatct atcgctgcggcggcggcggagtttggccgtaggtggcgccctcttcctcccatgcgtg -continued tgaccccgaagcccctcatcggctgaagcagggctaggtcggcgacaacgcgctcggctaatatg gcctgctgcacctgcgtgagggtagactggaagtcatccatgtccaca aagcggtggtatgcgcccgtgttgatggtgtaagtgcagttggccataacggaccagttaacg gtctggtgacccggctgcgagagctcggtgtacctgagacgcgagtaa gccctcgagtcaaatacgtagtcgttgcaagtccgcaccaggtactggtatcccaccaaaaagtgcggc ggcggctggcggtagaggggccagcgtagggtggccggggg ctccgggggcgagatcttccaacataaggcgatgatatccgtagatgtacctggacatccaggtgatgccg gcggcggtggtggaggcgcgcggaaagtcgcggacgcg gttccagatgttgcgcagcggcaaaaagtgctccatggtcgggacgctctggccggtc aggcgcgcgcaatcgttgacgctctaccgtgcaaaaggagagcctgtaagcg ggcactcttccgtggtctggtggataaattcgcaagggtatcatggcggacgaccggggttc gagccccgtatccggccgtccgccgtgatccatgcggttaccgcccgcgt gtcgaacccaggtgtgcgacgtcagacaacggggagtgctccttttggcttccttccaggcgcggcggctg ctgcgctagcttttttggccactggccgcgcgcagcgtaa gcggttaggctggaaagcgaaagcattaagtggctcgctccctgtagccggagggttattttccaagggt tgagtcgcgggacccccggttcgagtctcggaccggccgga ctgcggcgaacgggggtttgcctccccgtcatgcaagaccccgcttgcaaattcctccggaaacagggacg agcccctttttttgcttttcccagatgcatccggtgctgcggc agatgcgccccctcctcagcagcggcaagagcaagagcagcggcagacatgcagggcaccctcccctcct cctaccgcgtcaggaggggcgacatccgcggttgacg cggcagcagatggtgattacgaacccccgcggcgccgggccggcactac ctggacttggaggagggcgagggcctggcgcggctaggagcgccctctcctgagcgg tacccaagggtgcagctgaagcgtgatacgcgtgaggcgtacgtgccgcggcagaacctgtttcgcgaccgcg agggagaggagcccgaggagatgcgggatcgaaa gttccacgcagggcgcgagctgcggcatggcctgaatcgcgagcggttgctgcgcgagga ggactttgagcccgacgcgcgaaccgggattagtcccgcgcgcgcaca cgtggcggccgccgacctggtaaccgcatacgagcagacggtgaaccaggagattaactttcaaa aaagctttaacaaccacgtgcgtacgcttgtggcgcgcgaggagg tggctataggactgatgcatctgtgggactttgtaagcgcgctggagcaaaacccaaatagcaagccgct catggcgcagctgttccttatagtgcagcacagcagggacaa cgaggcattcagggatgcgctgctaaacatagtagagcccgagggccgctggctgctcgat ttgataaacatcctgcagagcatagtggtgcaggagcgcagcttgagcct ggctgacaaggtggccgccatcaactattccatgcttagcctgggcaagttttacgcccgcaagatataccata ccccttacgttcccatagacaaggaggtaaagatcgagg ggttctacatgcgcatggcgctgaaggtgcttaccttgagcgacgacctgggcgtttatcgcaa cgagcgcatccacaaggccgtgagcgtgagccggcggcgcgagctc agcgaccgcgagctgatgcacagcctgcaaagggccctggctggcacgggcagcggcgatagagaggccga gtcctactttgacgcggggcgctgacctgcgctgggc cccaagccgacgcgccctggaggcagctggggccggacctgggctggcggtggcacccgcgcgcgctggc aacgtcggcggcgtggaggaatatgacgaggacgat gagtacgagccagaggacggcgagtactaagcggtgatgtttctgatcagatgatgcaagacgcaacggacccggcggtg -continued cgggcggcgctgcagagccagccgtccggccttaactccacggacgactggcgccaggtc atggaccgcatcatgtcgctgactgcgcgcaatcctgacgcgttccggcagcagccgcaggccaaccggctctccgca attctggaagcggtggtcccggcgcgcgcaaaccccacgcacgagaaggtgctggcgatcgt aaacgcgctggccgaaaacagggccatccggcccgacgaggccgg cctggtctacgacgcgctgcttcagcgcgtggctcgttacaacagcggcaacgtgcag accaacctggaccggctggtggggggatgtgcgcgaggccgtggcgcagcgt gagcgcgcgcagcagcagggcaacctgggctccatggttgcactaaacgccttcctgagtac acagcccgccaacgtgccgcggggacaggaggactacaccaactttg tgagcgcactgcggctaatggtgactgagacaccgcaaagtgaggtgtaccagtctgggccagactattt tttccagaccagtagacaaggcctgcagaccgtaaacctgagccaggcttttcaaaaacttgcaggggctgtgg ggggtgcgggctcccacaggcgaccgcgcgaccgtgtctagcttgctgacgcccaactcgcgcctgttgctgctgctaata gcgcccttcacggacagtggcagcgtgtcccgggacacatacctaggtcacttgctgacactgtaccgcgaggccata ggtcaggcgcatgtggacgagcatactttccag gagattacaagtgtcagccgcgcgctggggcaggaggacacgggcagcctggaggcaaccct aaactacctgctgaccaaccggcggcagaagatcccctcgttgcac agtttaaacagcgaggaggagcgcattttgcgctacgtgcagcagagcgtgagccttaacc tgatgcgcgacggggtaacgcccagcgtggcgctggacatgaccgcgc gcaacatggaaccgggcatgtatgcctcaaaccggccgtttatcaaccgcctaatggactacttg catcgcgcggccgccgtgaaccccgagtatttcaccaatgccatcttg aacccgcactggctaccgcccctggtttctacaccgggggattcgaggtgcccgagggtaacgatg gattcctctgggacgacatagacgacagcgtgtttcccgcaac cgcagaccctgctagagttgcaacagcgcgagcaggcagaggcggcgctgcgaaaggaaagcttccgcaggcc aagcagcttgtccgatctaggcgctgcggccccgc ggtcagatgctagtagcccatttccaagcttgatagggtctcttaccagcactcgcaccacccgcccgcgc ctgctgggcgaggaggagtacctaaacaactcgctgctgca gccgcagcgcgaaaaaaacctgcctccggcatttcccaacaacgggatagagagcctagtggacaagatgagtag atggaagacgtacgcgcaggagcacagggacgt gccaggcccgcgcccgcccacccgtcgtcaaaggcacgaccgtcagcggggtctggtgtgggaggacga tgactcggcagacgacagcagcgtcctggatttgggagggagtggcaacccgtttgcgcaccttcgcccc aggctggggagaatgttttaaaaaaaaaaaagcatgatgcaaaataaaaaaactcaccaaggccatggcaccgagcgttg gttttcttgtattcccccttagtatgcggcgcgcggcgatgtatgaggaaggtcctcctccctcctacgagag tgtggtgagcgcggcgccagtggcggcggcgctgggttctc ccttcgatgctcccctggacccgccgtttgtgcctccgcggtacctgcgcgcctaccgggggg agaaacagcatccgttactctgagttggcaccccctattcgacaccacccgt gtgtacctggtggacaacaagtcaacggatgtggcatccctgaactaccagaacgacca cagcaactttctgaccacggtcattcaaaacaatgactacagcccggggggag gcaagcacacagaccatcaatcttgacgaccggtcgcactggggcggcgacctgaaaac catcctgcataccaacatgccaaatgtgaacgagttcatgtttaccaataagtt taaggcgcgggtgatggtgtcgcgcttgcctactaaggacaatcaggtggagctgaaata cgagtgggtggagttcacgctgcccgagggcaactactccgagaccatga -continued

```
ccatagaccttatgaacaacgcgatcgtggagcactacttgaaagtgggcagacagaacggggttctggaaagcg acatcggggtaaagtttgacacccgcaacttcagac tggggtttgaccccgtcactggtcttgtcatgcctggggtatatacaaacgaagccttccatccagacatcattttg ctgccaggatgcggggtggacttcacccacagccgcct gagcaacttgttgggcatccgcaagcggcaacccttccaggagggctttaggatcacctacgatgatct ggagggtggtaacattcccgcactgttggatgtggacgcctacc aggcgagcttgaaagatgacaccgaacagggcggggggtggcgcaggcggcagcaacagcagtggcagcgg cgcggaagagaactccaacgcggcagccgcggca atgcagccggtggaggacatgaacgatcatgccattcgcggcgacacc tttgccacacgggctgaggagaagcgcgctgaggccgaagcagcggccgaagctgccgc ccccgctgcgcaacccgaggtcgagaagcctcagaagaaaccggtgatcaaacccctgacagaggacagc aagaaacgcagttacaacctaataagcaatgacagcac cttcacccagtaccgcagctggtaccttgcatacaactacggcgaccctcagaccggaatccgctcatggaccctgc tttgcactcctgacgtaacctgcggctcggagcag gtctactggtcgttgccagacatgatgcaagaccccgtgaccttccgctccacgcgccagatcagcaactttccggt ggtgggcgccgagctgttgcccgtgcactccaaga gcttctacaacgaccaggccgtctactcccaactcatccgccagtttacctctctgacccacgtgttcaa tcgctttcccgagaaccagatttttggcgcgcccgccagcccccca ccatcaccaccgtcagtgaaaacgttcctgctctcacagatcacgggacgctaccgctgcgcaacagcatcgg aggagtccagcgagtgaccattactgacgccagacgc cgcacctgcccctacgtttacaaggccctgggcatagtctcgccgcgcgtcctatcgagccgcacttt ttgagcaagcatgtccatccttatatcgcccagcaataacacaggc tggggcctgcgcttcccaagcaagatgtttggcggggccaagaagcgctccgaccaacacccagtgcgcgtgcgcgggc actaccgcgcgccctggggcgcgcacaaacgcggccgcactgggcgcaccaccgtcgatgacgc catcgacgcggtggtggaggaggcgcgcaactacacgcccacgccgccaccagtgtccacagtggacgcgg ccattcagaccgtggtgcgcggagcccggcgctatgctaaaatgaagagacggcggaggcgcgtagcacgt cgccaccgccgccgacccggcactgccgcccaacgc gcggcggcggccctgcttaaccgcgcacgtcgcaccggccgacgggcggccatgcgggccgctc gaaggctggccgcgggtattgtcactgtgccccccaggtccag gcgacgagcggccgccgcagcagccgcgggccattagtgctatgactcagggtcgcaggggcaacgtgtattg ggtgcgcgactcggttagcggcctgcgcgtgcccgtgcgcacccgcccccgcgcaactagattgcaagaaa aaactacttagactcgtactgttgtatgtatccagcggcggcggcgcgcaacgaagctatgtccaagcgcaaaatc aaagaagagatgctccaggtcatcgcgccggagatctatggccccccgaagaaggaagagcagg attacaagccccgaaagctaaagcgggtcaaaaagaaaaagaaa gatgatgatgatgaacttgacgacgaggtggaactgctgcacgctaccgcgcccaggcgacgggtacag tggaaaggtcgacgcgtaaaacgtgttttgcgacccggcac caccgtagtctttacgcccggtgagcgctccacccgcacctacaagcgcgtgtatgatgaggtgtacggcgacg aggacctgcttgagcaggcaacgagcgcctcgggg agtttgcctacggaaagcggcataaggacatgctggcgttgccgctggacgagggcaacccaac acctagcctaaagcccgtaacactgcagcaggtgctgcccgcgctt gcaccgtccgaagaaaagcgcggcctaaagcgcgagtctggtgacttggcacccaccgtgc
```

-continued agctgatggtacccaagcgccagcgactggaagatgtcttggaaaaaat gaccgtggaacctgggctggagcccgaggtccgcgtgcggccaatcaagcaggtggcgccgggactgggcgt gcagaccgtggacgttcagatacccactaccagtag caccagtattgccaccgccacagagggcatggagacacaaacgtccccggttgcctcag cggtggcggatgccgcggtgcaggcggtcgctgcggccgcgtccaagac ctctacggaggtgcaaacggacccgtggatgtttcgcgtttcagcccccggcgcccgcgcggt tcgaggaagtacggcgccgccagcgcgctactgcccgaatatgccc tacatccttccattgcgcctacccccggctatcgtggctacacctaccgccccagaagacga gcaactacccgacgccgaaccaccactggaacccgccgccgccgtcgc cgtcgccagcccgtgctggccccgatttccgtgcgcagggtggctcgcgaaggaggcaggacc ctggtgctgccaacagcgcgctaccaccccagcatcgtttaaaagc cggtctttgtggttcttgcagatatggccctcacctgccgcctccgtttcccggtgccggga ttccgaggaagaatgcaccgtaggaggggcatggccggccacggcctgac gggcggcatgcgtcgtgcgcaccaccggcggcggcgcgcgtcgcaccgtcgcatgcgcggcggta tcctgcccctccttattccactgatcgccgcggcgattggcgcc gtgcccggaattgcatccgtggccttgcaggcgcagagacactgattaaaaacaagttgcatgtggaaaaatcaaa ataaaaagtctggactctcacgctcgcttggtcctgta actattttgtagaatggaagacatcaacttttgcgtctctggccccgcgacacggctcgcgcccgttcatgggaaa ctggcaagatatcggcaccagcaatatgagcggtggc gccttcagctggggctcgctgtggagcggcattaaaaatttcggttccaccgttaagaactatggcagcaag gcctggaacagcagcacaggccagatgctgagggataag ttgaaagagcaaaatttccaacaaaggtggtagatggcctggcctctggcattagcggggtggtggacctggccaac caggcagtgcaaaataagattaacagtaagcttg atccccgccctcccgtagaggagcctccaccggccgtggagacagtgtctccagaggggcgtggcg aaaagcgtccgcgccccgacagggaagaaactctggtgacgc aaatagacgagcctccctcgtacgaggaggcactaaagcaaggcctgcccaccacccgtcccatcgcgccc atggctaccggagtgctgggccagcacacacccgtaac gctggacctgcctccccccgccgacacccagcagaaacctgtgctgccaggcccgaccgccgttgttgtaaccc gtcctagccgcgcgtccctgcgccgcgccgccagcggtccgcgatcgttgcggcccgtagccagtggcaactggc aaagcacactgaacagcatcgtgggtctgggggtgcaatccctgaagcgccgacgatgcttctgaatagct aacgtgtcgtatgtgtgtcatgtatgcgtccatgtcgccgccagaggagctgctgagccgccgcgcgcccgctttccaag atggctacccccttcgatgatgccgcagtggtctt acatgcacatctcgggccaggacgcctcggagtacctgagcccccgggctggtgcagtttg cccgcgccaccgagacgtacttcagcctgaataacaagtttagaaacccca cggtggcgcctacgcacgacgtgaccacagaccggtcccagcgtttgacgctgcggttcatccctgtgg accgtgaggatactgcgtactcgtacaaggcgcggttcaccctagctgtgggtgataaccgtgtgctggacatggcttcc acgtactttgacatccgcgcgtgctggacaggggccctacttttaagccctactctggcactgcctacaacgccc tggctcccaagggtgccccaaatccttgcgaatgggatgaagctgctactgctcttga aataaacctagaagaagaggacgatgacaacgaagacgaagtagacgagcaa gctgagcagcaaaaaactcacgtatttgggcaggcgccttattctggtataaatattacaaaggag -continued

```
ggtattcaaataggtgtcgaaggtcaaacacctaaatatgccgataaaaacatttcaacctgaacctcaaataggagaa tctcagtggtacgaaactgaaattaatcatgcagctgggagagtccttaaaaagactaccccaatgaaaccatgttacggttcat atgcaaaacccacaaatgaaaatggagggcaaggcattcttgtaaagcaacaaaatggaaagctagaaagtcaagtggaaatg caattttttctcaactactgaggcgaccgc aggcaatggtgataacttgactcctaaagtggtattgtacagtgaagatgtagatatagaaaccccagacactcatatttcttaca tgcccactattaaggaaggtaactcacgagaactaatgggccaacaatctatgcccaacaggcctaattacattgcttttaggga caattttattggtctaatgtattacaacagcacgggtaatatgggtgttctggcgggccaagcatcgcagttgaatgctgttgtag atttgcaagacagaaacacagagct ttcataccagcttttgcttgattccattggtgatagaaccaggtacttttctatgtggaatcaggctgtt gacagctatgatccagatgttagaattattgaaaatcatggaactgaagatgaacttccaaattactgctttccactg ggaggtgtgattaatacagagactcttaccaaggtaaaacctaaaacaggtcaggaaaatggatgggaaaaagat gctacagaattttcagataaaaatgaaataagagttggaaataattttgccatggaaatcaatctaaatgccaacctgt ggagaaatttcctgtactccaacatagcgctgtatttgcccgacaagctaaagtacagtccttccaacgtaaaaatttctga taacccaaacacctacgactacatgaacaagcg agtggtggctcccgggttagtggactgctacattaaccttggagcacgctggtcccttgactatatggaca acgtcaacccatttaaccaccaccgcaatgctggcctgcgctaccgctcaatgttgctgggcaatggtcgctat gtgcccttccacatccaggtgcctcagaagttctttgccattaaaaacctccttctcctgccgggctcatacacctacgagtgga acttcaggaaggatgttaacatggttctgcagagctccctaggaaatgacctaagggttgacggagccagcatt aagtttgatagcatttgcctttacgccaccttcttccccatg gcccacaacaccgcctccacgcttgaggccatgcttagaaacgacaccaacgaccagtcctttaacgactatct ctccgccgccaacatgctctaccctataccc gccaacg ctaccaacgtgcccatatccatcccctcccgcaactgggcggctttccgcggctgggccttcacgcgccttaagactaag gaaaccccatcactgggctcgggctacgaccc ttattacacctactctggctctataccctacctagatggaaccttttacctcaaccacacctttaagaaggt ggccattacctttgactcttctgtcagctggcctggcaatgaccgcctgcttacccccaacgagtttgaaattaa gcgctcagttgacggggagggttacaacgttgcccagtgtaacatgaccaaagactggttcctggtacaaatgctagctaa ctacaacattggctaccagggcttctatatcccagagagctacaaggaccgcatgtactccttctttag aaacttccagcccatgagccgtcaggtggtggatgatactaaatacaag gactaccaacaggtgggcatcctacaccaacacaacaactctggatttgttggctaccttgcccccacca tgcgcgaaggacaggcctaccctgctaacttcccctatccgctt ataggcaagaccgcagttgacagcattacccagaaaaagtttctttgcgatcgcacccttggcgcatccca ttctccagtaactttatgtccatgggcgcactcacagacctgg gccaaaaccttctctacgccaactccgcccacgcgctagacatgacttttgaggtggatcccatggacgagcccacccttct ttatgtttttgtttgaagtctttgacgtggtccgtg tgcaccggccgcaccgcggcgtcatcgaaaccgtgtacctgcgcacgcccttctcggccggcaacgc cacaacataaagaagcaagcaacatcaacaacagctgccgcc atgggctccagtgagcaggaactgaaagccattgtcaaagatcttggttgtgggccatatttttttgggcacctatgac aagcgctttccaggctttgtttctccacacaagctcgc ctgcgccatagtcaatacggccggtcgcgagactgggggcgtacactggatggcctt tgcctggaacccgcactcaaaaacatgctacctctttgagcccttggcttttctga ccagcgactcaagcaggtttaccagtttgagtacgagtcactcctgcgccgtagcgccattgcttcttcccccgaccgct
```

-continued gtataacgctggaaaagtccacccaaagcgtacaggggcccaactcggccgcctgtggactattctgctgcatgtt tctccacgcctttgccaactggccccaaactcccatggatcacaaccccaccatgaaccttattaccggggg tacccaactccatgctcaacagtccccaggtacagcccaccctgcgtcgcaaccaggaacagctctacagcttcctggagc gccactcgccctacttccgcagccacagtgc gcagattaggagcgccacttcttttttgtcacttgaaaaacatgtaaaaataatgtactaga gacactttcaataaaggcaaatgcttttatttgtacactctcgggtgattattta cccccacccttgccgtctgcgccgtttaaaaatcaaaggggttctgccgcgcatcgctatgcgccactggcagggacacgt tgcgatactggtgtttagtgctccacttaaactcaggcacaaccatccgcggcagctcggtgaagttttcac tccacaggctgcgcaccatcaccaacgcgtttagcaggtcgggcgccgatatcttgaagtcgcagttggggcctccg ccctgcgcgcgcgagttgcgatacacaggggttgcagcactggaacactatcagcgccgggtggtgcacgctggccag cacgctcttgtcggagatcagatccgcgtccaggtcctccgcgttgctcagggcgaacggagtcaactttggtagc tgccttcccaaaaagggcgcgtgcccaggctttgagttgcactcgcaccgtagtggcatcaaaaggtga ccgtgcccggtctgggcgttaggatacagcgcctgcataaaagccttgatctgcttaaaagccacctgagcctttgcgcc ttcagagaagaacatgccgcaagacttgccggaaaactgattggccggacaggccgcgtcgtgcacgcagcaccttgc gtcggtgttggagatctgcaccacatttcggccccaccggttcttcacgatcttggccttgctagact gctccttcagcgcgcgctgcccgttttcgctcgtcacatccatttcaatcacgtgctccttatttatcata atgcttccgtgtagacacttaagctcgccttcgatctcagcgca gcggtgcagccacaacgcgcagcccgtgggctcgtgatgcttgtaggtcacctctgcaaacgactgcaggtacgcctgcaggaat cgccccatcatcgtcacaaaggtcttgttgctggtgaaggtcagctgcaacccgcggtgctcctcgt tcagccaggtcttgcatacggccgccagagcttccacttggtcaggcagtagtttgaagttcgcctttagatcgttat ccacgtggtacttgtccatcagcgcgcgcgcagcctccatgcccttctcccacgcagacacgatcggcacactcagcgggttcat caccgtaatttcactttccgcttcgctgggctcttcctcttcctcttgcgtccgcataccacgcgccactgggtcgtcttcattca gccgccgcactgtgcgcttacctcctttgccatgcttgattagcaccggtgggttgctga aacccaccatttgtagcgccacatcttctctttcttcctcgctgtccacgattacctctggtgatggcgggcgctcgggctt gggagaagggcgcttctttttcttcttgggcgcaatggccaaatccgccgccgaggtc gatggccgcgggctgggtgtgcgcggcaccagcgcgtcttgtgatgagtcttcctcgtcctcggactcgatacgccgcctcatccgctttt tttggggcgcccggggaggcggcggcgacggggacggggacgacacgtcctccatggttgg gggacgtcgcgccgcaccgcgtccgcgctcggggggtggtttcgcgctgctcctcttcccgactggccatttccttctccta taggcagaaaaagatcatggagtcagtcgagaagaaggacagcctaaccgcccccctctgagttcgccaccaccgcctc caccgatgccgccaacgcgcctaccaccttccccgtcgaggcaccccgcttgaggaggaggaagtga ttatcgagcaggacccaggttttgtaagcgaagacgacgaggaccgctcagtaccaacgagggataaaaaagcaagaccaggaca acgcagaggcaaacgaggaacaagtcgggcggggggacgaaaggcatggcgactacctagatg tgggagacgacgtgctgttgaagcatctgcagcgccagtgcgccattatctgcgacgcgttgcaagagcgcagc gatgtgcccctcgccatagcggatgtcagccttgcctacgaacgccacctattctcaccgcgcgtaccccccaaacg ccaagaaaacggcacatgcgagcccaacccgcgcctcaacttctaccccgtatttgccgtgccagaggtgct tgccacctatcacatctttttccaaaactgcaagatacccctatcctgccgtgccaaccgcagccgagcggacaagc agctggccttgcgggcagggcgctgtcatacctgatatcgcctcgctcaacgaagtgccaaaaatctttgagggtctt ggacgcgacgagaagcgcgcggcaaacgctctgcaacaggaaaacagcgaaatgaaagtcactctgga gtgttggtggaactcgagggtgacaacgcgcgcctagccgtactaaaacgcagcatcgaggtcacccactttgcctacccggc acttaacctaccccccaaggtcatgagcacagtcatgagtgagctgatcgtgcgccgtgcgcagcccctggagaggga -continued

```
tgcaaatttgcaagaacaaacagaggagggcctacccgcagttggcgacgagcagctag cgcgctggcttcaaacgcgcgagcctgccgacttggaggagcgacgcaaactaatgatggccgcagtgctcgttaccgtgga gcttgagtgcatgcagcggttctttgctgacccggagatgcagcgcaagctagaggaaacattg cactacacctttcgacagggctacgtacgccaggcctgcaagatctccaacgtggagctctgcaacctggtctccta ccttggaattttgcacgaaaaccgccttgggcaaaacgtgcttcattccacgctcaagggcgaggcgcgccgcgactacgtc cgcgactgcgtttacttatttctatgctacacctggcagacggccatgggcgtttggcagcagtgc ttggaggagtgcaacctcaaggagctgcagaaactgctaaagcaaaacttgaaggacctatggacggccttcaacga gcgctccgtggccgcgcacctggcggacatcattttccccgaacgcctgcttaaaaccctgcaacagggt ctgccagacttcaccagtcaaagcatgttgcagaactttagga actttatcctagagcgctcaggaatcttgcccgccacctgctgtgcacttcctagcgactttgtgcccattaagtaccg cgaatgccctccgccgctttggggccactgctaccttctgcagctagccaactaccttgcctaccact ctgacataatggaagacgtgagcggtgacggtctactggagtgtcactgtcgctgcaacctatgcaccccgcaccgctccct ggtttgcaattcgcagctgcttaacgaaagtcaaattatcggtacctttgagctgcagggtccctcgcctgacgaaaagtccgc ggctccggggttgaaactcactccggggctgtggacgtcggcttaccttcgca aatttgtacctgaggactaccacgcccacgagattaggttctacgaagaccaatcccgcccgccaaatgcggagctt accgcctgcgtcattacccagggccacattcttggccaattgcaagccatcaacaaagcccgc caagagtttctgctacgaaagggacggggggtttacttggacccccagtccggcgaggagc tcaacccaatccccccgccgccgcagccctatcagcagcagccgcgggcccttgcttcccaggatggcaccca aaaagaagctgcagctgccgccgccacccacggacgaggaggaatactgggacagtcaggcagaggaggttttg gacgaggaggaggaggacatgatggaagactgggagagcctagacgaggaagcttccgaggtcgaaga ggtgtcagacgaaacaccgtcaccctcggtcgcattcccctcgccggcgccccagaaatcggcaaccggttccagcatggc tacaacctccgctcctcaggcgccgccggcactgcccgttcgccgacccaaccgtagatgggacaccactggaacc agggccggtaagtccaagcagccgccgccgttagcccaagagcaacaacagcgccaaggct accgctcatggcgcgggcacaagaacgccatagttgcttgcttgcaagactgtgggggcaacatctc cttcgcccgccgctttcttctctaccatcacggcgtggccttcccccgtaacatcctgcattactaccgtcatctc tacagcccatactgcaccggcggcagcggcagcggcagcaacagcagcggccacacagaagcaaaggcgaccggatagca agactctgacaaagcccaagaaatccacagcggcggcagcagcaggaggaggagcgctgcgtct ggcgcccaacgaacccgtatcgacccgcgagcttagaaacaggattttttcccactctgtatgctatatttcaaca gagcaggggccaagaacaagagctgaaaataaaaaaacaggtctctgcgatccctcacccgcagctgcctgtatcacaaaagc gaagatcagcttcggcgcacgctggaagacgcggaggctctcttcagtaaatactgcgcgctgactcttaaggactagtttc gcgcccttctcaaatttaagcgcgaaaactacgtcatctccagcggccacacccggcgcca gcacctgtcgtcagcgccattatgagcaaggaaattcccacgccctacatgtggagttaccagccacaaatgggacttgcg gctggagctgcccaagactactcaacccgaataaactacatgagcgcgggaccccacatgatatcccgggtcaacg gaatccgcgcccaccgaaaccgaattctcttggaacaggcggctattaccaccacacctcgta ataaccttaatccccgtagttggcccgctgccctggtgtaccaggaaagtcccgctcccaccactgtggtacttcccagagacgc ccaggccgaagttcagatgactaactcaggggcgcagcttgcgggcggctttcgtcacagggtgcg gtcgcccgggcagggtataactcacctgacaatcagagggcgaggtattcagctcaacgacgagtcgg tgagctcctcgcttggtctccgtccggacgggacatttcagatcggcggcgccggccgtccttcattcacgcctcgtcaggcaatcct aactctgcagacctcgtcctctgagccgcgctctggaggcattggaactctgcaatttat tgaggagtttgtgccatcggtctactttaacccccttctcgggacctcccggccact atccggatcaatttattcctaactttgacgcggtaaaggactcggcggacggctacgactgaatgt
``` taagtggagaggcagagcaactgcgcctgaaacacctggtccactgtcgccgccacaagtgctttgcccgcgac tccggtgagttttgctactttgaattgcccgaggatcatatcgagggcccggcgcacggcgtccggcttaccgcccagggagag cttgcccgtagcctgattcgggagtttacccagcgcccctgctagttgagcgggacaggggaccctgtgttctcac tgtgatttgcaactgtcctaaccttggattacatcaagatcctctagttataactagagtacccgg ggatcttattccctttaactaataaaaaaaaataataaagcatcacttaccttaaaatcagttagcaaatttctgt ccagtttattcagcagacctccttgccctcctcccagctctggtattgcagcttcctcctggc tgcaaactttctccacaatctaaatggaatgtcagtttcctcctgttcctgtccatccgcacccactatcttc atgttgttgcagatgaagcgcgcaagaccgtctgaagataccttcaaccccgtgtatccatatgacacggaaaccgg tcctccaactgtgccttttcttactcctccctttgtatcccccaatgggtttcaagagagtcccccct ggggtactctctttgcgcctatccgaacctctagttacctccaatggcatgcttgcgctcaaaatgggcaacggcctctctct ggacgaggccggcaaccttacctcccaaaatgtaaccactgtgagcccacctctcaaaaaaaccaagtcaaaca taaacctggaaatatctgcacccctcacagttacctcagaagccctaactgtggctgccgccgcacctctaatggtcgcgg gcaacacactcaccatgcaatcacaggccccgctaaccgtgcacgactccaaacttagcattgccacccaagga cccctcacagtgtcagaaggaaagctagccctgcaaacatcaggcccctcaccaccaccgatagcagtacccttactat cactgcctcacccccctctaactactgccactggtagcttgggcattgacttgaaagagcccatttatacacaaaatggaaaac taggactaaagtacggggctcctttgcatgtaacagacgacctaaacactttgaccgtagcaact ggtccaggtgtgactattaataatacttccttgcaaactaaagttactggagccttgggttttgattcacaaggcaatatgca acttaatgtagcaggaggactaaggattgattctcaaaacagacgcccttatacttgatgttagttatccgtttgatg ctcaaaaccaactaaatctaagactaggacagggccctcttttttataaactcagcccacaacttggatattaacta caacaaaggcctttacttgtttacagcttcaaacaattccaaaaagcttgaggttaacctaagcactgc caaggggttgatgtttgacgctacagccatagccattaatgcagga gatgggcttgaatttggttcacctaatgcaccaaacacaaatcccctcaaaacaaaaattgg ccatggcctagaatttgattcaaacaaggctatggttcctaaactaggaactg gccttagttttgacagcacaggtgccattacagtaggaaacaaaaataatgataagctaa ctttgtggaccacaccagctccatctcctaactgtagactaaatgcagagaaag atgctaaactcactttggtcttaacaaaatgtggcagtcaaatacttgctacagtttcagttt tggctgttaaaggcagtttggctccaatatctggaacagttcaaagtgctcatcttattataagatttgacgaaaatggagt gctactaaacaattccttcctggacccagaatattggaactttagaaatggagatcttactgaaggcacagcctatacaaac gctgttggatttatgcctaacctatcagcttatccaaaatctcacggtaaaactgccaaaagtaacatt gtcagtcaagtttacttaaacggagacaaaactaaacctgtaacactaaccattacac taaacggtacacaggaaacaggagacacaactccaagtgcatactctatgtcattttcatg ggactggtctggccacaactacattaatgaaatatttgcca catcctcttacacttttttcatacattgcccaagaataaagaatcgtttgtgttatg tttcaacgtgtttattttttcaattgcagaaaatttcaagtcatttttcatt cagtagtatagccccaccaccacatagcttatacagatcaccgtaccttaatcaaactcacagaaccctag tattcaacctgccacctccctcccaacacacagagtacacagtcctttctccccggctggccttaaaaagc atcatatcatgggtaacagacatattcttaggtgttatattccacacggtttcctg tcgagccaaacgctcatcagtgatattaataaactccccgggcagctcacttaagttcatgtcgct gtccagctgctgagccacaggctgctgtccaacttgcggttgcttaacgggcggcgaaggagaagtccacgc ctacatgggggtagagtcataatcgtgcatcaggatagg -continued gcggtggtgctgcagcagcgcgcgaataaactgctgccgccgccgctccgtcctgcaggaatacaacatggcagtggtctcctcag cgatgattcgcaccgcccgcagcataaggcgccttgtcctccgggcacagcagcgcaccctgatctcacttaaatcagcacag taactgcagcacagcaccacaatattgttcaaaatcccacagtgcaaggcgct gtatccaaagctcatggcggggaccacagaacccacgtggccatcataccacaagcgcaggtagattaa gtggcgacccctcataaacacgctggacataaacattacctct tttggcatgttgtaattcaccacctcccggtaccatataaacctctgattaaacatggcgccatccaccaccatcctaaaccagctgg ccaaaacctgcccgccggctatacactgcagggaaccgggactggaacaatgacagtggagagcccaggactcgtaaccatggat catcatgctcgtcatgatatcaatgttggcacaacacaggcacacgtgcatac acttcctcaggattacaagctcctcccgcgttagaaccatatcccagggaacaacccattcctgaatcagc gtaaatcccacactgcagggaagacctcgcacgtaactcacg ttgtgcattgtcaaagtgttacattcgggcagcagcggatgatcctccagtatggtagc gcgggtttctgtctcaaaaggaggtagacgatccctactgtacggagtgcgccga gacaaccgagatcgtgttggtcgtagtgtcatgccaaatggaacgccggacgtagtcatattt cctgaagcaaaaccaggtgcgggcgtgacaaacagatctgcgtctccgg tctcgccgcttagatcgctctgtgtagtagttgtagtatatccactctctcaaagcatccaggcgccccc tggcttcgggttctatgtaaactccttcatgcgccgctgccctgat aacatccaccaccgcagaataagccacacccagccaacctacacattcgttctgcgagtca cacacgggaggagcgggaagagctggaagaaccatgtttttttttttttattccaaa agattatccaaaacctcaaaatgaagatctattaagtgaacgcgctcccctccggtggcgtggtcaaactc tacagccaaagaacagataatggcatttgtaagatgttgcaca atggcttccaaaaggcaaacggccctcacgtccaagtggacgtaaaggctaaacccttcagggtgaatctcctctat aaacattccagcaccttcaaccatgcccaaataattc tcatctcgccaccttctcaatatatctctaagcaaatcccgaatattaagtccggccattgtaaaaatc tgctccagagcgccctccaccttcagcctcaagcagcgaatcatga ttgcaaaaattcaggttcctcacagacctgtataagattcaaaagcgg aacattaacaaaaataccgcgatcccgtaggtcccttcgcagggccagctgaacataatcgtgcagg tctgcacggaccagcgcggccacttccccgccaggaaccttgacaaaagaacccacactgattatgaca cgcatactcggagctatgctaaccagcgtagccccgatgtaa gctttgttgcatgggcggcgatataaaatgcaaggtgctgctcaaaaaatcaggcaaagcctcgcgcaaaaaagaa agcacatcgtagtcatgctcatgcagataaaggcag gtaagctccggaaccaccacagaaaaagacaccattttctctcaaacatgtctgcgggtttctgcataaacacaaaataaa ataacaaaaaaacatttaaacattagaagcctg tcttacaacaggaaaaacaacccttataagcataagacggactacggccatgccg gcgtgaccgtaaaaaaaactggtcaccgtgattaaaaagcaccaccgacagctcctc ggtcatgtccggagtcataatgtaagactcggtaaacacatcaggttgattcatcggtcagtgc taaaaagcgaccgaaatagcccggggggaatacatacccgcaggcgtag agacaacattacagcccccataggaggtataacaaaattaataggagagaaaaacacataaacacctg aaaaaccctcctgcctaggcaaaatagcaccctcccgctccag aacaacatacagcgcttcacagcggcagcctaacagtcagccttaccagtaaa aaagaaaacctattaaaaaaacaccactcgacacggcaccagctcaatcagtcacagt gtaaaaaagggccaagtgcagagcgagtatatataggactaaaaaaatgacgtaacggttaaagtccacaaaaaacacccagaaaccgcac -continued gcgaacctacgcccagaa acgaaagccaaaaaacccacaacttcctcaaatcgtcacttccgttttcccacgttacgtaacttcccatttt aagaaaactacaattcccaacacatacaagttactccgc cctaaaacctacgtcacccgccccgttcccacgccccgcgccacgtcacaaactccaccccctcattatcatattggcttcaa tccaaaataaggtatattattgatgatnnn Nucleic acid sequence of the pAdROSd vector.

(SEQ ID NO: 12)

nnttaattaaggatccnnncctgtcctcgaccgatgcccttgagagccttcaacccagtcagctccttccggtgggcgcggggcatgactatc gtcgccgcacttatgactgtcttctttatcatgcaactcgtaggacaggtgccggcagcgctctgggtcattttcggcgaggaccgctttcgctgg agcgcgacgatgatcggcctgtcgcttgcggtattcggaatcttgcacgccctcgctcaagccttcgtcactggtcccgccaccaaacgtttcg gcgagaagcaggccattatcgccggcatggcggccgacgcgctgggctacgtcttgctggcgttcgcgacgcgaggctggatggccttccc cattatgattcttctcgcttccggcggcatcgggatgcccgcgttgcaggccatgctgtccaggcaggtagatgacgaccatcagggacagctt caaggatcgctcgcggctcttaccagcctaacttcgatcactggaccgctgatcgtcacggcgatttatgccgcctcggcgagcacatggaac gggttggcatggattgtaggcgccgccctataccttgtctgcctccccgcgttgcgtcgcggtgcatggagccgggccacctcgacctgaatg gaagccggcggcacctcgctaacggattcaccactccaagaattggagccaatcaattcttgcggagaactgtgaatgcgcaaaccaacccctt ggcagaacatatccatcgcgtccgccatctccagcagccgcacgcggcgcatctcgggcagcgttgggtcctggccacgggtgcgcatgat cgtgctcctgtcgttgaggacccggctaggctggcggggttgccttactggttagcagaatgaatcaccgatacgcgagcgaacgtgaagcg actgctgctgcaaaacgtctgcgacctgagcaacaacatgaatggtcttcggtttccgtgtttcgtaaagtctggaaacgcggaagtcagcgcc ctgcaccattatgttccggatctgcatcgcaggatgctgctggctaccctgtggaacacctacatctgtattaacgaagcgctggcattgaccctg agtgattttctctggtcccgccgcatccataccgccagttgtttaccctcacaacgttccagtaaccgggcatgttcatcatcagtaacccgtatc gtgagcatcctctctcgtttcatcggtatcattaccccccatgaacagaaattccccctttacacggaggcatcaagtgaccaaacaggaaaaaacc gcccttaacatggcccgctttatcagaagccagacattaacgcttctggagaaactcaacgagctggacgcggatgaacaggcagacatctgt gaatcgcttcacgaccacgctgatgagctttaccgcagctgcctcgcgcgtttcggtgatgacggtgaaaacctctgacacatgcagctcccg gagacggtcacagcttgtctgtaagcggatgccgggagcagacaagcccgtcagggcgcgtcagcgggtgttggcgggtgtcggggcgc agccatgacccagtcacgtagcgatagcggagtgtatactggcttaactatgcggcatcagagcagattgtactgagagtgcaccatatgcggt gtgaaataccgcacagatgcgtaaggagaaaataccgcatcaggcgctcttccgcttcctcgctcactgactcgctgcgctcggtcgttcggct gcggcgagcggtatcagctcactcaaaggcggtaatacggttatccacagaatcaggggataacgcaggaaagaacatgtgagcaaaagg ccagcaaaaggccaggaaccgtaaaaaggccgcgttgctggcgtttttccataggctccgcccccctgacgagcatcacaaaaatcgacgct caagtcagaggtggcgaaacccgacaggactataaagataccaggcgtttccccctggaagctccctcgtgcgctctcctgttccgaccctgc cgcttaccggatacctgtccgcctttctcccttcgggaagcgtggcgctttctcaatgctcacgctgtaggtatctcagttcggtgtaggtcgttcg ctccaagctgggctgtgtgcacgaaccccccgttcagcccgaccgctgcgccttatccggtaactatcgtcttgagtccaacccggtaagaca cgacttatcgccactggcagcagccactggtaacaggattagcagagcgaggtatgtaggcggtgctacagagttcttgaagtggtggcctaa ctacggctacactagaaggacagtatttggtatctgcgctctgctgaagccagttaccttcggaaaaagagttggtagctcttgatccggcaaac aaaccaccgctggtagcggtggtttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaattaaaaatg aagttttaaatcaatctaaagtatatatgagtaaacttggtctgacagttaccaatgcttaatcagtgaggcacctatctcagcgatctgtctatttcgt tcatccatagttgcctgactccccgtcgtgtagataactacgatacgggagggcttaccatctggccccagtgctgcaatgataccgcgagacc cacgctcaccggctccagatttatcagcaataaaccagccagccggaagggccgagcgcagaagtggtcctgcaactttatccgcctccatc cagtctattaattgttgccgggaagctagagtaagtagttcgccagttaatagtttgcgcaacgttgttgnnaaaaaggatcttcacctagatcctttt tcacgtagaaagccagtccgcagaaacggtgctgaccccggatgaatgtcagctactgggctatctggacaagggaaaacgcaagcgcaaa gagaaagcaggtagcttgcagtgggcttacatggcgatagctagactgggcggttttatggacagcaagcgaaccggaattgccagctgggg -continued

```
cgccctctggtaaggttgggaagccctgcaaagtaaactggatggctttctcgccgccaaggatctgatggcgcaggggatcaagctctgatc aagagacaggatgaggatcgtttcgcatgattgaacaagatggattgcacgcaggttctccggccgcttgggtggagaggctattcggctatg actgggcacaacagacaatcggctgctctgatgccgccgtgttccggctgtcagcgcaggggcgcccggttcttttttgtcaagaccgacctgt ccggtgccctgaatgaactgcaagacgaggcagcgcggctatcgtggctggccacgacgggcgttccttgcgcagctgtgctcgacgttgtc actgaagcgggaagggactggctgctattgggcgaagtgccggggcaggatctcctgtcatctcaccttgctcctgccgagaaagtatccatc atggctgatgcaatgcggcggctgcatacgcttgatccggctacctgcccattcgaccaccaagcgaaacatcgcatcgagcgagcacgtac tcggatggaagccggtcttgtcgatcaggatgatctggacgaagagcatcaggggctcgcgccagccgaactgttcgccaggctcaaggcg agcatgcccgacggcgaggatctcgtcgtgacccatggcgatgcctgcttgccgaatatcatggtggaaaatggccgcttttctggattcatcg actgtggccggctgggtgtggcggaccgctatcaggacatagcgttggctacccgtgatattgctgaagagcttggcggcgaatgggctgac cgcttcctcgtgctttacggtatcgccgctcccgattcgcagcgcatcgccttctatcgccttcttgacgagttcttctgaattttgttaaaatttttg ttaaatcagctcattttttaaccaataggccgaaatcggcaacatcccttatataaatcaaaagaatagaccgcgatagggttgagtgttgttccagtttg gaacaagagtccactattaaagaacgtggactccaacgtcaaagggcgaaaaaccgtctatcagggcgatggcccactacgtgaaccatcac ccaaatcaagttttttgcggtcgaggtgccgtaaagctctaaatcggaacccaaagggagcccccgatttagagcttgacggggaaagccgg cgaacgtggcgagaaaggaagggaagaaagcgaaaggagcgggcgctagggcgctggcaagtgtagcggtcacgctgcgcgtaacca ccacacccgcgcgcttaatgcgccgnnnnnnttaattaannntccttccagctctctgcccctttggattgaagccaatatgataatgaggg ggtggagtttgtgacgtggcgcggggcgtgggaacggggcgggtgacgtagtagtgtggcggaagtgtgatgttgcaagtgtggcggaac acatgtaagcgacggatgtggcaaaagtgacgttttggtgtgcgccggtgtacacaggaagtgacaattttcgcgcggtttttaggcggatgttg tagtaaatttgggcgtaaccgagtaagatttggccattttcgcgggaaaactgaataagaggaagtgaaatctgaataattttgtgttactcatagc gcgtaannngtagttattaatagtaatcaattacggggtcattagttcatagcccatatatggagttccgcgttacataacttacggtaaatggccc gcctggctgaccgcccaacgacccccgcccattgacgtcaataatgacgtatgttcccatagtaacgccaataggactttccattgacgtcaat gggtggagtatttacggtaaactgcccacttggcagtacatcaagtgtatcatatgccaagtacgccccctattgacgtcaatgacggtaaatgg cccgcctggcattatgcccagtacatgaccttatgggactttcctacttggcagtacatctacgtattagtcatcgctattaccatggtgatgcggttt tggcagtacatcaatgggcgtggatagcggtttgactcacggggatttccaagtctccaccccattgacgtcaatgggagtttgttttggcacca aaatcaacgggactttccaaaatgtcgtaacaactccgccccattgacgcaaatgggcggtaggcgtgtacggtgggaggtctatataagcag agctggtttagtgaaccgtcagatccgctagaccatggcctcctccgaggacgtcatcaaggagttcatgcgcttcaaggtgcgcatggaggg ctccgtgaacggccacgagttcgagatcgagggcgagggcgagggccgcccctacgagggcacccagaccgccaagctgaaggtgacc aagggcggccccctgcccttcgcctgggacatcctgtcccctcagttccagtacggctccaaggcctacgtgaagcaccccgccgacatccc cgactacttgaagctgtccttccccgagggcttcaagtgggagcgcgtgatgaacttcgaggacggcggcgtggtgaccgtgacccaggact cctccctgcaggacggcgagttcatctacaaggtgaagctgcgcggcaccaacttccccctccgacggccccgtaatgcagaagaagaccat gggctgggaggcctccaccgagcggatgtaccccgaggacggcgccctgaagggcgagatcaagatgaggctgaagctgaaggacggc ggccactacgacgccgaggtcaagaccacctacatggccaagaagcccgtgcagctgcccggcgcctacaagaccgacatcaagctgga catcacctcccacaacgaggactacaccatcgtggaacagtacgagcgcgccgagggccgccactccaccggcgccaatccaccggatct agataactgatcataatcagccataccacatttgtagaggttttacttgctttaaaaaacctcccacacctcccctgaacctgaaacataaaatga atgcaattgttgttgttaacttgtttattgcagcttataatggttacaaataaagcaatagcatcacaaatttcacaaataaagcatttttttcactgc attctagttgtggtttgtccaaactcatcaatgtatcttaacgcgtctctagttattaatagtaatcaattacggggtcattagttcatagcccatat atggagttccgcgttacataacttacggtaaatggcccgcctggctgaccgcccaacgacccccgcccattgacgtcaataatgacgtatgttcccata gtaacgccaataggactttccattgacgtcaatgggtggagtatttacggtaaactgcccacttggcagtacatcaagtgtatcatatgccaagt acgccccctattgacgtcaatgacggtaaatggcccgcctggcattatgcccagtacatgaccttatgggactttcctacttggcagtacatctac gtattagtcatcgctattaccatggtgatgcggttttggcagtacatcaatgggcgtggatagcggtttgactcacggggatttccaagtctccacc ccattgacgtcaatgggagtttgttttggaaccaaaatcaacgggactttccaaaatgtcgtaacaactccgccccattgacgcaaatgggcggt aggcgtgtacggtgggaggtctatataagcagagctctccctatcagtgatagagatctccctatcagtgatagagatctccctatcagtgatag
```

-continued

```
agatctccctatcagtgatagagatcgagctgtttagtgaaccgtcagatcgcctggagacgccatccacgctgttttgacctccatagaagaca ccgaattcaggggatccaatcggaaagcggacgcggaatttaaattgattttttgcggtataagaatatatactgatatgtatacccgaagtatgtc aaaaagaggtatgctatgaagcagcgtattacagtgacagttgacagcgacagctatcagttgctcaaggcatatatgatgtcaatatctccggt ctggtaagcacaaccatgcagaatgaagcccgtcgtctgcgtgccgaacgctggaaagcggaaatcaggaagggatggctgaggtcgcc cggtttattgaaatgaacggctcttttgctgacgagaacaggggctggtgaaatgcagtttaaggtttacacctataaaagagagagccgttatc gtctgtttgtggatgtacagagtgatattattgacacgcccgggcgacggatggtgatcccctggccagtgcacgtctgctgtcagataaagtc tcccgtgaactttacccggtggtgcatatcggggatgaaagctggcgcatgatgaccaccgatatggccagtgtgccggtctccgttatcggg gaagaagtggctgatctcagccaccgcgaaaatgacatcaaaaacgccattaacctgatgttctggggaatataaatgtcaggctcccttatac acagccagtctgcagctcgctcttcatttaaatcgagtatcccgtgagcgcctttctagagatatcggccgctaaacccgctgatcagcctcgact gtgccttctagttgccagccatctgttgtttgcccctcccccgtgccttccttgaccctggaagtgccactcccactgtcctttcctaataaaatga ggaaattgcatcgcattgtctgagtaggtgtcattctattctgggggtggggtggggcaggacagcaagggggaggattgggaagacaata gcaggcatgctggggatgcggtgggctctatggcttctgaggcggaaagaaccaggatctgctaggatctnntaagggtgggaaagaatata taaggtgggggtcttatgtagtttttgtatctgttttgcagcagccgccgccgccatgagcaccaactcgtttgatggaagcattgtgagctcatattt gacaacgcgcatgcccccatgggccggggtgcgtcagaatgtgatgggctccagcattgatggtcgcccgtcctgcccgcaaactctacta ccttgacctacgagaccgtgtctggaacgccgttggagactgcagcctccgccgccgcttcagccgctgcagccaccgcccgcgggattgtg actgactttgctttcctgagcccgcttgcaagcagtgcagcttcccgttcatccgcccgcgatgacaagttgacggctcttttggcacaattggatt ctttgacccgggaacttaatgtcgtttctcagcagctgttggatctgcgccagcaggtttctgccctgaaggcttcctcccctcccaatgcggttta aaacataaataaaaaaccagactctgtttggatttggatcaagcaagtgtcttgctgtctttatttaggggttttgcgcgcgcggtaggcccggga ccagcggtctcggtcgttgagggtcctgtgtatttttttccaggacgtggtaaaggtgactctggatgttcagatacatgggcataagcccgtctct gggtggaggtagcaccactgcagagcttcatgctgcgggggtggtgttgtagatgatccagtcgtagcaggagcgctgggcgtggtgcctaa aaatgtctttcagtagcaagctgattgccaggggcaggcccttggtgtaagtgtttacaaagcggttaagctgggatgggtgcatacgtgggga tatgagatgcatcttcggactgtatttttaggttggctatgttcccagccatatccctccggggattcatgttgtgcagaaccaccagcacagtgtatc cggtgcacttgggaaatttgtcatgtagcttagaaggaaatgcgtggaagaacttggagacgcccttgtgacctccaagattttccatgcattcgt ccataatgatggcaatgggcccacgggcggcggcctgggcgaagatatttctgggatcactaacgtcatagttgtgttccaggatgagatcgtc ataggccatttttacaaagcgcgggcggagggtgccagactgcggtataatggttccatccggcccaggggcgtagttaccctcacagatttg catttcccacgctttgagttcagatggggggatcatgtctacctgcggggcgatgaagaaaacggtttccggggtaggggagatcagctggga agaaagcaggttcctgagcagctgcgacttaccgcagccggtgggcccgtaaatcacacctattaccgggtgcaactggtagttaagagagc tgcagctgccgtcatccctgagcaggggggccacttcgttaagcatgtccctgactcgcatgtttttccctgaccaaatccgccagaaggcgctc gccgcccagcgatagcagttcttgcaaggaagcaaagttttttcaacggtttgagaccgtccgccgtaggcatgcttttgagcgtttgaccaagc agttccaggcggtcccacagctcggtcacctgctctacggcatctcgatccagcatatctcctcgtttcgcgggttggggcggctttcgctgtac ggcagtagtcggtgctcgtccagacgggccagggtcatgtctttccacgggcgcagggtcctcgtcagcgtagtctgggtcacggtgaaggg gtgcgctccgggctgcgcgctggccagggtgcgcttgaggctggtcctgctggtgctgaagcgctgccggtcttcgccctgcgcgtcggcca ggtagcatttgaccatggtgtcatagtccagcccctccgcggcgtggcccttggcgcgcagcttgcccttggaggaggcgccgcacgaggg gcagtgcagacttttgagggcgtagagcttgggcgcgagaaataccgattccggggagtaggcatccgcgccgcaggccccgcagacggt ctcgcattccacgagccaggtgagctctggccgttcggggtcaaaaaccaggtttcccccatgctttttgatgcgtttcttacctctggtttccatga gccggtgtccacgctcggtgacgaaaaggctgtccgtgtccccgtatacagacttgagaggcctgtcctcgacggtgttccgcggtcctcct cgtatagaaactcggaccactctgagacaaaggctcgcgtccaggccagcacgaaggaggctaagtgggaggggtagcggtcgttgtcca ctaggggggtccactcgctccagggtgtgaagacacatgtcgccctcttcggcatcaaggaaggtgattggtttgtaggtgtaggccacgtgac cgggtgttcctgaaggggggctataaaagggggtggggcgcgttcgtcctcactctcttccgcatcgctgtctgcgagggccagctgttggg gtgagtactccctctgaaaagcgggcatgacttctgcgctaagattgtcagtttccaaaaacgaggaggatttgatattcacctggcccgcggtg
```

-continued atgcctttgagggtggccgcatccatctggtcagaaaagacaatcttttttgttgtcaagcttggtggcaaacgacccgtagagggcgttggaca gcaacttggcgatggagcgcagggtttggttttttgtcgcgatcggcgcgctccttggccgcgatgtttagctgcacgtattcgcgcgcaacgca ccgccattcgggaaagacggtggtgcgctcgtcgggcaccaggtgcacgcgccaaccgcggttgtgcagggtgacaaggtcaacgctggt ggctacctctccgcgtaggcgctcgttggtccagcagaggcggccgcccttgcgcgagcagaatggcggtaggggggtctagctgcgtctcg tccggggggtctgcgtccacggtaaagacccgggcagcaggcgcgcgtcgaagtagtctatcttgcatccttgcaagtctagcgcctgctg ccatgcgcgggcggcaagcgcgcgctcgtatgggttgagtgggggaccccatggcatggggtgggtgagcgcggaggcgtacatgccgc aaatgtcgtaaacgtagaggggctctctgagtattccaagatatgtagggtagcatcttccaccgcggatgctggcgcgcacgtaatcgtatagt tcgtgcgagggagcgaggaggtcgggaccgaggttgctacgggcgggctgctctgctcggaagactatctgcctgaagatggcatgtgagt tggatgatatggttggacgctggaagacgttgaagctggcgtctgtgagacctaccgcgtcacgcacgaaggaggcgtaggagtcgcgcag cttgttgaccagctcggcggtgacctgcacgtctagggcgcagtagtccagggtttccttgatgatgtcatacttatcctgtcccttttttttttcca cagctcgcggttgaggacaaactcttcgcggtctttccagtactcttggatcggaaacccgtcggcctccgaacggtaagagcctagcatgtagaac tggttgacggcctggtaggcgcagcatccctttttctacgggtagcgcgtatgcctgcgcggccttccggagcgaggtgtgggtgagcgcaaa ggtgtccctgaccatgactttgaggtactggtatttgaagtcagtgtcgtcgcatccgccctgctcccagagcaaaaagtccgtgcgcttttttgga acgcggatttggcagggcgaaggtgacatcgttgaagagtatctttcccgcgcgaggcataaagttgcgtgtgatgcggaagggtcccggca cctcggaacggttgttaattacctgggcggcgagcacgatctcgtcaaagccgttgatgttgtggcccacaatgtaaagttccaagaagcgcg ggatgcccttgatggaaggcaatttttttaagttcctcgtaggtgagctcttcaggggagctgagcccgtgctctgaaagggcccagtctgcaag atgagggttggaagcgacgaatgagctccacaggtcacgggccattagcatttgcaggtggtcgcgaaaggtcctaaactggcgacctatgg ccattttttctggggtgatgcagtagaaggtaagcgggtcttgttcccagcggtcccatccaaggttcgcggctaggtctcgcgcggcagtcact agaggctcatctccgccgaacttcatgaccagcatgaagggcacgagctgcttcccaaaggcccccatccaagtataggtctctacatcgtag gtgacaaagagacgctcggtgcgaggatgcgagccgatcgggaagaactggatctcccgccaccaattggaggagtggctattgatgtggt gaaagtagaagtccctgcgacgggccgaacactcgtgctggcttttgtaaaaacgtgcgcagtactggcagcggtgcacgggctgtacatcct gcacgaggttgacctgacgaccgcgcacaaggaagcagagtgggaatttgagcccctcgcctggcgggtttggctggtggtcttctacttcg gctgcttgtccttgaccgtctggctgctcgaggggagttacggtggatcggaccaccacgccgcgcgagcccaaagtccagatgtccgcgcg cggcggtcggagcttgatgacaacatcgcgcagatgggagctgtccatggtctggagctcccgcggcgtcaggtcaggcgggagctcctgc aggtttacctcgcatagacgggtcagggcgcgggctagatccaggtgatacctaatttccaggggctggttggtggcggcgtcgatggcttgc aagaggccgcatccccgcggcgcgactacggtaccgcgcggcgggcggtgggccgcggggggtgtccttggatgatgcatctaaaagcgg tgacgcgggcgagcccccggaggtaggggggggctccggacccgccgggagaggggcaggggcacgtcggcgccgcgcgcgggca ggagctggtgctgcgcgcgtaggttgctggcgaacgcgacgacgcggcggttgatctcctgaatctggcgcctctgcgtgaagacgacggg cccggtgagcttgagcctgaaagagagttcgacagaatcaatttcggtgtcgttgacggcggcctggcgcaaaatctcctgcacgtctcctga gttgtcttgataggcgatctcggccatgaactgctcgatctcttcctcctggagatctccgcgtccggctcgctccacggtggcggcgaggtcgt tggaaatgcgggccatgagctgcgagaaggcgttgaggcctccctcgttccagacgcggctgtagaccacgcccccttcggcatcgcgggc gcgcatgaccacctgcgcgagattgagctccacgtgccgggcgaagacggcgtagtttcgcaggcgctgaaagaggtagttgagggtggtg gcggtgtgttctgccacgaagaagtacataacccagcgtcgcaacgtggattcgttgatatcccccaaggcctcaaggcgctccatggcctcg tagaagtccacggcgaagttgaaaaactgggagttgcgcgccgacacggttaactcctcctccagaagacggatgagctcggcgacagtgtc gcgcacctcgcgctcaaaggctacaggggcctcttcttcttcttcaatctcctcttccataaagggcctcccccttcttcttcttctggcggcggtggg ggagggggggacacggcggcgacgacggcgcaccgggaggcggtcgacaaagcgctcgatcatctccccgcggcgacggcgcatggtc tcggtgacggcgcggccgttctcgcggggcgcagttggaagacgccgcccgtcatgtcccggttatgggttggcggggggctgccatgc ggcagggatacggcgctaacgatgcatctcaacaattgttgtgtaggtactccgccgccgagggacctgagcgagtccgcatcgaccggatc ggaaaacctctcgagaaaggcgtctaaccagtcacagtcgcaaggtaggctgagcaccgtggcgggcggcagcgggcggcggtcggggt tgtttctggcggaggtgctgctgatgatgtaattaaagtaggcggtcttgagacggcggatggtcgacagaagcaccatgtccttgggtccggc ctgctgaatgcgcaggcggtcggccatgccccaggcttcgttttgacatcggcgcaggtctttgtagtagtcttgcatgagcctttctaccggca -continued

```
cttcttcttctccttcctcttgtcctgcatctcttgcatctatcgctgcggcggcggcggagtttggccgtaggtggcgccctcttcctcccatgcgt gtgaccccgaagcccctcatcggctgaagcagggctaggtcggcgacaacgcgctcggctaatatggcctgctgcacctgcgtgagggtag actggaagtcatccatgtccacaaagcggtggtatgcgcccgtgttgatggtgtaagtgcagttggccataacggaccagttaacggtctggtg acccggctgcgagagctcggtgtacctgagacgcgagtaagccctcgagtcaaatacgtagtcgttgcaagtccgcaccaggtactggtatc ccaccaaaaagtgcggcggcggctggcggtagaggggccagcgtagggtggccggggctccgggggcgagatcttccaacataaggcg atgatatccgtagatgtacctggacatccaggtgatgccggcggcggtggtggaggcgcgcggaaagtcgcggacgcggttccagatgttg cgcagcggcaaaaagtgctccatggtcgggacgctctggccggtcaggcgcgcgcaatcgttgacgctctaccgtgcaaaaggagagcct gtaagcgggcactcttccgtggtctggtggataaattcgcaagggtatcatggcggacgaccggggttcgagccccgtatccggccgtccgc cgtgatccatgcggttaccgcccgcgtgtcgaacccaggtgtgcgacgtcagacaacggggagtgctccttttggcttccttccaggcgcgg cggctgctgcgctagcttttttggccactggccgcgcgcagcgtaagcggttaggctggaaagcgaaagcattaagtggctcgctccctgtag ccggagggttattttccaagggttgagtcgcgggacccccggttcgagtctcggaccggccggactgcggcgaacgggggtttgcctcccc gtcatgcaagacccgcgcttgcaaattcctccggaaacagggacgagcccctttttttgcttttcccagatgcatccggtgctgcggcagatgcgc cccctcctcagcagcggcaagagcaagagcagcggcagacatgcagggcaccctcccctcctcctaccgcgtcaggaggggcgacatc cgcggttgacgcggcagcagatggtgattacgaacccccgcggcgccgggccggcactacctggacttggaggagggcgagggcctg gcgcggctaggagcgccctctcctgagcggtacccaagggtgcagctgaagcgtgatacgcgtgaggcgtacgtgccgcggcagaacctg tttcgcgaccgcgagggagaggagcccgaggagatgcgggatcgaaagttccacgcagggcgcgagctgcggcatggcctgaatcgcga gcggttgctgcgcgaggaggactttgagcccgacgcgcgaaccgggattagtcccgcgcgcgcacacgtggcggccgccgacctggtaa ccgcatacgagcagacggtgaaccaggagattaactttcaaaaaagctttaacaaccacgtgcgtacgcttgtggcgcgcgaggaggtggct ataggactgatgcatctgtgggactttgtaagcgcgctggagcaaaacccaaatagcaagccgctcatggcgcagctgttccttatagtgcagc acagcagggacaacgaggcattcagggatgcgctgctaaacatagtagagcccgagggccgctggctgctcgatttgataaacatcctgcag agcatagtggtgcaggagcgcagcttgagcctggctgacaaggtggccgccatcaactattccatgcttagcctgggcaagttttacgcccgc aagatataccatacccccttacgttcccatagacaaggaggtaaagatcgaggggttctacatgcgcatggcgctgaaggtgcttaccttgagcg acgacctgggcgtttatcgcaacgagcgcatccacaaggccgtgagcgtgagccggcggcgcgagctcagcgaccgcgagctgatgcac agcctgcaaagggccctggctggcacgggcagcggcgatagagaggccgagtcctactttgacgcgggcgctgacctgcgctgggcccc aagccgacgcgcccctggaggcagctggggccggacctgggctggcggtggcaccgcgcgcgctggcaacgtcggcggcgtggagga atatgacgaggacgatgagtacgagccagaggacggcgagtactaagcggtgatgtttctgatcagatgatgcaagacgcaacggacccgg cggtgcgggcggcgctgcagagccagccgtccggcccttaactccacggacgactggcgccaggtcatggaccgcatcatgtcgctgactg cgcgcaatcctgacgcgttccggcagcagccgcaggccaaccggctctccgcaattctggaagcggtggtcccggcgcgcgcaaaccccca cgcacgagaaggtgctggcgatcgtaaacgcgctggccgaaaacagggccatccggcccgacgaggccgcctggtctacgacgcgctg cttcagcgcgtggctcgttacaacagcggcaacgtgcagaccaacctggaccggctggtgggggatgtgcgcgaggccgtggcgcagcgt gagcgcgcgcagcagcagggcaacctgggctccatggttgcactaaacgccttcctgagtacacagcccgccaacgtgccgcggggacag gaggactacaccaactttgtgagcgcactgcggctaatggtgactgagacaccgcaaagtgaggtgtaccagtctgggccagactattttttcc agaccagtagacaaggcctgcagaccgtaaacctgagccaggctttcaaaaacttgcaggggctgtggggggtgcgggctcccacaggcg accgcgcgaccgtgtctagcttgctgacgcccaactcgcgcctgttgctgctgctaatagcgcccttcacggacagtggcagcgtgtcccggg acacatacctaggtcacttgctgacactgtaccgcgaggccataggtcaggcgcatgtgacgagcatactttccaggagattacaagtgtca gccgcgcgctggggcaggaggacacgggcagcctggaggcaacccaaactacctgctgaccaaccggcggcagaagatcccctcgttg cacagtttaaacagcgaggaggagcgcattttgcgctacgtgcagcagagcgtgagccttaacctgatgcgcgacggggtaacgcccagcg tggcgctggacatgaccgcgcgcaacatggaaccgggcatgtatgcctcaaaccggccgtttatcaaccgcctaatggactacttgcatcgcg cggccgccgtgaaccccgagtatttcaccaatgccatcttgaacccgcactggctaccgcccccctggtttctacaccggggggattcgaggtgc ccgagggtaacgatggattcctctgggacgacatagacgacagcgtgttttccccgcaaccgcagaccctgctagagttgcaacagcgcgag
```

-continued

```
caggcagaggcggcgctgcgaaaggaaagcttccgcaggccaagcagcttgtccgatctaggcgctgcggccccgcggtcagatgctagt agcccatttccaagcttgatagggtctcttaccagcactcgcaccacccgcccgcgcctgctgggcgaggaggagtacctaaacaactcgctg ctgcagccgcagcgcgaaaaaaacctgcctccggcatttcccaacaacgggatagagagcctagtggacaagatgagtagatggaagacgt acgcgcaggagcacagggacgtgccaggcccgcgcccgcccacccgtcgtcaaaggcacgaccgtcagcggggtctggtgtgggagga cgatgactcggcagacgacagcagcgtcctggatttgggagggagtggcaacccgtttgcgcaccttcgccccaggctggggagaatgtttt aaaaaaaaaaaagcatgatgcaaaataaaaaactcaccaaggccatggcaccgagcgttggttttcttgtattccccttagtatgcggcgcgcg gcgatgtatgaggaaggtcctcctccctcctacgagagtgtggtgagcgcggcgccagtggcggcggcgctgggttctcccttcgatgctcc cctggacccgccgtttgtgcctccgcggtacctgcggcctaccgggggggagaaacagcatccgttactctgagttggcacccctattcgacac cacccgtgtgtacctggtggacaacaagtcaacgatgtggcatccctgaactaccagaacgaccacagcaactttctgaccacggtcattca aaacaatgactacagcccggggggaggcaagcacacagaccatcaatcttgacgaccggtcgcactggggcggcgacctgaaaaccatcct gcataccaacatgccaaatgtgaacgagttcatgtttaccaataagtttaaggcgcgggtgatggtgtcgcgcttgcctactaaggacaatcagg tggagctgaaatacgagtgggtggagttcacgctgcccgagggcaactactccgagaccatgaccatagaccttatgaacaacgcgatcgtg gagcactacttgaaagtgggcagacagaacggggttctggaaagcgacatcggggtaaagtttgacacccgcaacttcagactggggtttga ccccgtcactggtcttgtcatgcctggggtatatacaaacgaagccttccatccagacatcattttgctgccaggatgcggggtggacttcaccc acagccgcctgagcaacttgttgggcatccgcaagcggcaacccttccaggagggctttaggatcacctacgatgatctggagggtggtaac attcccgcactgttggatgtggacgcctaccaggcgagcttgaaagatgacaccgaacagggcgggggtggcgcaggcggcagcaacag cagtggcagcggcgcggaagagaactccaacgcggcagccgcggcaatgcagccggtggaggacatgaacgatcatgccattcgcggc gacacctttgccacacgggctgaggagaagcgcgctgaggccgaagcagcggccgaagctgccgcccccgctgcgcaacccgaggtcg agaagcctcagaagaaaccggtgatcaaacccctgacagaggacagcaagaaacgcagttacaacctaataagcaatgacagcacccttcac ccagtaccgcagctggtaccttgcatacaactacggcgaccctcagaccggaatccgctcatggaccctgctttgcactcctgacgtaacctgc ggctcggagcaggtctactggtcgttgccagacatgatgcaagaccccgtgaccttccgctccacgcgccagatcagcaactttccggtggtg ggcgccgagctgttgcccgtgcactccaagagcttctacaacgaccaggccgtctactcccaactcatccgccagtttacctctctgacccacg tgttcaatcgctttcccgagaaccagattttggcgcgcccgccagcccccaccatcaccaccgtcagtgaaaacgttcctgctctcacagatca cgggacgctaccgctgcgcaacagcatcggaggagtccagcgagtgaccattactgacgccagacgccgcacctgcccctacgtttacaag gccctgggcatagtctcgccgcgcgtcctatcgagccgcacttttttgagcaagcatgtccatccttatatcgcccagcaataacacaggctggg gcctgcgcttcccaagcaagatgtttggcggggccaagaagcgctccgaccaacacccagtgcgcgtgcgcgggcactaccgcgcgccct ggggcgcgcacaaacgcggccgcactgggcgcaccaccgtcgatgacgccatcgacgcggtggtggaggaggcgcgcaactacacgc ccacgccgccaccagtgtccacagtggacgcggccattcagaccgtggtgcgcggagcccggcgctatgctaaaatgaagagacggcgg aggcgcgtagcacgtcgccaccgccgccgacccggcactgccgcccaacgcgcggcggcggccctgcttaaccgcgcacgtcgcaccg gccgacgggcggccatgcgggccgctcgaaggctggccgcgggtattgtcactgtgcccccccaggtccaggcgacgagcggccgccgc agcagccgcggccattagtgctatgactcagggtcgcaggggcaacgtgtattgggtgcgcgactcggttagcggcctgcgcgtgcccgtg cgcacccgccccccgcgcaactagattgcaagaaaaaactacttagactcgtactgttgtatgtatccagcggcggcggcgcgcaacgaagc tatgtccaagcgcaaaatcaaagaagagatgctccaggtcatcgcgccggagatctatggccccccgaagaaggaagagcaggattacaag ccccgaaagctaaagcgggtcaaaaagaaaaagaaagatgatgatgatgaacttgacgacgaggtggaactgctgcacgctaccgcgccc aggcgacgggtacagtggaaaggtcgacgcgtaaaacgtgttttgcgacccggcaccaccgtagtctttacgcccggtgagcgctccaccc gcacctacaagcgcgtgtatgatgaggtgtacggcgacgaggacctgcttgagcaggccaacgagcgcctcggggagtttgcctacggaaa gcggcataaggacatgctggcgttgccgctggacgagggcaacccaacacctagcctaaagcccgtaacactgcagcaggtgctgcccgc gcttgcaccgtccgaagaaaagcgcgggcctaaagcgcgagtctggtgacttggcacccaccgtgcagctgatggtacccaagcgccagcg actggaagatgtcttggaaaaaatgaccgtggaacctgggctggagcccgaggtccgcgtgcggccaatcaagcaggtggcgccgggact gggcgtgcagaccgtggacgttcagatacccactaccagtagcaccagtattgccaccgccacagagggcatggagacacaaacgtcccc ggttgcctcagcggtggcggatgccgcggtgcaggcggtcgctgcggccgcgtccaagacctctacggaggtgcaaacggacccgtggat
```

```
gtttcgcgtttcagcccccggcgcccgcgcggttcgaggaagtacggcgccgccagcgcgctactgcccgaatatgccctacatccttccat tgcgcctaccccggctatcgtggctacacctaccgccccagaagacgagcaactacccgacgccgaaccaccactggaacccgccgccg ccgtcgccgtcgccagcccgtgctggccccgatttccgtgcgcagggtggctcgcgaaggaggcaggaccctggtgctgccaacagcgcg ctaccaccccagcatcgtttaaaagccggtctttgtggttcttgcagatatggccctcacctgccgcctccgtttcccggtgccgggattccgag gaagaatgcaccgtaggaggggcatggccggccacggcctgacgggcggcatgcgtcgtgcgcaccaccggcggcggcgcgcgtcgc accgtcgcatgcgcggcggtatcctgcccctccttattccactgatcgccgcggcgattggcgccgtgcccggaattgcatccgtggccttgca ggcgcagagacactgattaaaaacaagttgcatgtggaaaaatcaaaataaaaagtctggactctcacgctcgcttggtcctgtaactattttgta gaatggaagacatcaactttgcgtctctggccccgcgacacggctcgcgcccgttcatgggaaactggcaagatatcggcaccagcaatatg agcggtggcgccttcagctggggctcgctgtggagcggcattaaaaatttcggttccaccgttaagaactatggcagcaaggcctggaacag cagcacaggccagatgctgaggataagttgaaagagcaaaatttccaacaaaaggtggtagatggcctggcctctggcattagcggggtgg tggacctggccaaccaggcagtgcaaaataagattaacagtaagcttgatccccgccctcccgtagaggagcctccaccggccgtggagac agtgtctccagaggggcgtggcgaaaagcgtccgcgccccgacagggaagaaactctggtgacgcaaatagacgagcctccctcgtacga ggaggcactaaagcaaggcctgcccaccacccgtcccatcgcgcccatggctaccggagtgctgggccagcacacacccgtaacgctgga cctgcctccccccgccgacacccagcagaaacctgtgctgccaggcccgaccgccgttgttgtaaccgtcctagccgcgcgtccctgcgcc gcgccgccagcggtccgcgatcgttgcggcccgtagccagtggcaactggcaaagcacactgaacagcatcgtgggtctgggggtgcaat ccctgaagcgccgacgatgcttctgaatagctaacgtgtcgtatgtgtgtcatgtatgcgtccatgtcgccgccagaggagctgctgagccgcc gcgcgcccgctttccaagatggctaccccttcgatgatgccgcagtggtcttacatgcacatctcgggccaggacgcctcggagtacctgagc cccgggctggtgcagtttgcccgcgccaccgagacgtacttcagcctgaataacaagtttagaaaccccacggtggcgcctacgcacgacgt gaccacagaccggtcccagcgtttgacgctgcggttcatccctgtggaccgtgaggatactgcgtactcgtacaaggcgcggttcaccctagc tgtgggtgataaccgtgtgctggacatggcttccacgtactttgacatccgcggcgtgctggacaggggccctacttttaagccctactctggca ctgcctacaacgccctggctcccaagggtgccccaaatccttgcgaatgggatgaagctgctactgctcttgaaataaacctagaagaagagg acgatgacaacgaagacgaagtagacgagcaagctgagcagcaaaaaactcacgtatttgggcaggcgccttattctggtataaatattacaa aggagggtattcaaataggtgtcgaaggtcaaacacctaaatatgccgataaaacatttcaacctgaacctcaaataggagaatctcagtggta cgaaactgaaattaatcatgcagctgggagagtccttaaaaagactaccccaatgaaaccatgttacggttcatatgcaaaacccacaaatgaa aatggagggcaaggcattcttgtaaagcaacaaaatggaaagctagaaagtcaagtggaaatgcaattttttctcaactactgaggcgaccgca ggcaatggtgataacttgactcctaaagtggtattgtacagtgaagatgtagatatagaaaccccagacactcatatttcttacatgcccactatta aggaaggtaactcacgagaactaatgggccaacaatctatgcccaacaggcctaattacattgcttttagggacaattttattggtctaatgtatta caacagcacgggtaatatgggtgttctggcgggccaagcatcgcagttgaatgctgttgtagatttgcaagacagaaacacagagctttcatac cagcttttgcttgattccattggtgatagaaccaggtactttttctatgtggaatcaggctgttgacagctatgatccagatgttagaattattgaaaa tcatggaactgaagatgaacttccaaattactgctttccactgggaggtgtgattaatacagagactcttaccaaggtaaaacctaaaacaggtcag gaaaatggatgggaaaaagatgctacagaatttttcagataaaaatgaaataagagttggaaataattttgccatggaaatcaatctaaatgccaa cctgtggagaaatttcctgtactccaacatagcgctgtatttgcccgacaagctaaagtacagtccttccaacgtaaaaatttctgataacccaaac acctacgactacatgaacaagcgagtggtggctcccgggttagtggactgctacattaaccttggagcacgctggtcccttgactatatggaca acgtcaacccatttaaccaccaccgcaatgctggcctgcgctaccgctcaatgttgctgggcaatggtcgctatgtgcccttccacatccaggtg cctcagaagttctttgccattaaaaaacctccttctcctgccgggctcatacacctacgagtggaacttcaggaaggatgttaacatggttctgcag agctccctaggaaatgacctaaggggttgacggagccagcattaagtttgatagcatttgcctttacgccaccttcttccccatggcccacaacac cgcctccacgcttgaggccatgcttagaaacgacaccaacgaccagtcctttaacgactatctctccgccgccaacatgctctaccctataccc gccaacgctaccaacgtgcccatatccatccctcccgcaactgggcggctttccgcggctgggccttcacgcgccttaagactaaggaaac cccatcactgggctcgggctacgaccttattacacctactctggctctataccctacctagatggaacctttacctcaaccacacctttaagaag gtggccattaccttttgactcttctgtcagctggcctggcaatgaccgcctgcttaccccccaacgagtttgaaattaagcgctcagttgacgggga
```

-continued

```
gggttacaacgttgcccagtgtaacatgaccaaagactggttcctggtacaaatgctagctaactacaacattggctaccagggcttctatatccc agagagctacaaggaccgcatgtactccttctttagaaacttccagcccatgagccgtcaggtggtggatgatactaaatacaaggactaccaa caggtgggcatcctacaccaacacaacaactctggatttgttggctaccttgcccccaccatgcgcgaaggacaggcctaccctgctaacttcc cctatccgcttataggcaagaccgcagttgacagcattacccagaaaaagtttctttgcgatcgcaccctttggcgcatcccattctccagtaactt tatgtccatgggcgcactcacagacctgggccaaaaccttctctacgccaactccgcccacgcgctagacatgacttttgaggtggatcccatg gacgagcccaccccttctttatgtttttgtttgaagtctttgacgtggtccgtgtgcaccggccgcaccgcggcgtcatcgaaaccgtgtacctgcgc acgcccttctcggccggcaacgccacaacataaagaagcaagcaacatcaacaacagctgccgccatgggctccagtgagcaggaactga aagccattgtcaaagatcttggttgtgtgggccatatttttttgggcacctatgacaagcgctttccaggctttgtttctccacacaagctcgcctgcgcc atagtcaatacggccggtcgcgagactgggggcgtacactggatggcctttgcctggaacccgcactcaaaaacatgctacctctttgagccc tttggcttttctgaccagcgactcaagcaggtttaccagtttgagtacgagtcactcctgcgccgtagcgccattgcttcttcccccgaccgctgta taacgctggaaaagtccacccaaagcgtacaggggcccaactcggccgcctgtggactattctgctgcatgtttctccacgcctttgccaactg gccccaaactcccatggatcacaaccccaccatgaaccttattaccggggtacccaactccatgctcaacagtccccaggtacagcccaccct gcgtcgcaaccaggaacagctctacagcttcctggagcgccactcgccctacttccgcagccacagtgcgcagattaggagcgccacttcttt ttgtcacttgaaaaacatgtaaaaataatgtactagagacactttcaataaaggcaaatgcttttatttgtacactctcgggtgattatttaccccc acccttgccgtctgcgccgtttaaaaatcaaaggggttctgccgcgcatcgctatgcgccactggcagggacacgttgcgatactggtgtttagtgc tccacttaaactcaggcacaaccatccgcggcagctcggtgaagtttttcactccacaggctgcgcaccatcaccaacgcgtttagcaggtcgg gcgccgatatcttgaagtcgcagttggggcctccgccctgcgcgcgcgagttgcgatacacagggttgcagcactggaacactatcagcgcc gggtggtgcacgctggccagcacgctcttgtcggagatcagatccgcgtccaggtcctccgcgttgctcagggcgaacggagtcaactttggt agctgccttcccaaaaagggcgcgtgcccaggctttgagttgcactcgcaccgtagtggcatcaaaaggtgaccgtgcccggtctgggcgtta ggatacagcgcctgcataaaagccttgatctgcttaaaagccacctgagcctttgcgccttcagagaagaacatgccgcaagacttgccggaa aactgattggccggacaggccgcgtcgtgcacgcagcaccttgcgtcggtgttggagatctgcaccacatttcggccccaccggttcttcacg atcttggccttgctagactgctccttcagcgcgcgctgcccgttttcgctcgtcacatccatttcaatcacgtgctccttatttatcataatgcttcc gtgtagacacttaagctcgccttcgatctcagcgcagcggtgcagccacaacgcgcagcccgtgggctcgtgatgcttgtaggtcacctctgcaa acgactgcaggtacgcctgcaggaatcgccccatcatcgtcacaaaggtcttgttgctggtgaaggtcagctgcaacccgcggtgctcctcgtt cagccaggtcttgcatacggccgcagagcttccacttggtcaggcagtagtttgaagttcgcctttagatcgttatccacgtggtacttgtccatc agcgcgcgcgcagcctccatgcccttctcccacgcagacgatcggcacactcagcgggttcatcaccgtaatttcacttttccgcttcgctgg gctcttcctcttcctcttgcgtccgcataccacgcgccactgggtcgtcttcattcagccgccgcactgtgcgcttacctcctttgccatgcttgatt agcaccggtgggttgctgaaacccaccatttgtagcgccacatcttctctttcttcctcgctgtccacgattacctctggtgatggcgggcgctcg ggcttgggagaagggcgcttcttttttcttcttgggcgcaatggccaaatccgccgccgaggtcgatggccgcgggctgggtgtgcgcggcac cagcgcgtcttgtgatgagtcttcctcgtcctcggactcgatacgccgcctcatccgcttttttggggggcgcccggggaggcggcggcgacgg ggacggggacgacacgtcctccatggttgggggacgtcgcgccgcaccgcgtccgcgctcggggtggtttcgcgctgctcctcttcccga ctggccatttccttctcctataggcagaaaaagatcatggagtcagtcgagaagaaggacagcctaaccgcccctctgagttcgccaccacc gcctccaccgatgccgccaacgcgcctaccaccttccccgtcgaggcaccccgcttgaggaggaggaagtgattatcgagcaggaccca ggttttgtaagcgaagacgacgaggaccgctcagtaccaacagaggataaaaagcaagaccaggacaacgcagaggcaaacgaggaaca agtcgggcggggggacgaaaggcatggcgactacctagatgtgggagacgacgtgctgttgaagcatctgcagcgccagtgcgccattatc tgcgacgcgttgcaagagcgcagcgatgtgcccctcgccatagcggatgtcagccttgcctacgaacgccacctattctcaccgcgcgtacc ccccaaacgccaagaaaacggcacatgcgagcccaacccgcgcctcaacttctaccccgtatttgccgtgccagaggtgcttgccacctatc acatcttttttccaaaactgcaagataccccctatcctgccgtgccaaccgcagccgagcggacaagcagctggccttgcgggcagggcgctgtca tacctgatatcgcctcgctcaacgaagtgccaaaaatctttgagggtcttggacgcgacgagaagcgcgcggcaaacgctctgcaacaggaa aacagcgaaaatgaaagtcactctggagtgttggtggaactcgagggtgacaacgcgcgcctagccgtactaaaacgcagcatcgaggtca cccactttgcctacccggcacttaacctaccccccaaggtcatgagcacagtcatgagtgagctgatcgtgcgccgtgcgcagcccctggaga
```

-continued

```
gggatgcaaatttgcaagaacaaacagaggagggcctacccgcagttggcgacgagcagctagcgcgctggcttcaaacgcgcgagcctg ccgacttggaggagcgacgcaaactaatgatggccgcagtgctcgttaccgtggagcttgagtgcatgcagcggttctttgctgacccggaga tgcagcgcaagctagaggaaacattgcactacacctttcgacagggctacgtacgccaggcctgcaagatctccaacgtggagctctgcaac ctggtctcctaccttggaattttgcacgaaaaccgccttgggcaaaacgtgcttcattccacgctcaagggcgaggcgcgccgcgactacgtcc gcgactgcgtttacttatttctatgctacacctggcagacggccatgggcgtttggcagcagtgcttggaggagtgcaacctcaaggagctgca gaaactgctaaagcaaaacttgaaggacctatggacggccttcaacgagcgctccgtggccgcgcacctggcggacatcattttccccgaac gcctgcttaaaaccctgcaacagggtctgccagacttcaccagtcaaagcatgttgcagaacttttaggaactttatcctagagcgctcaggaatc ttgcccgccacctgctgtgcacttcctagcgactttgtgcccattaagtaccgcgaatgccctccgccgctttggggccactgctaccttctgcag ctagccaactaccttgcctaccactctgacataatggaagacgtgagcggtgacggtctactggagtgtcactgtcgctgcaacctatgcaccc cgcaccgctccctggtttgcaattcgcagctgcttaacgaaagtcaaattatcggtacctttgagctgcaggtccctcgcctgacgaaaagtcc gcggctccggggttgaaactcactccggggctgtggacgtcggcttaccttcgcaaatttgtacctgaggactaccacgcccacgagattagg ttctacgaagaccaatcccgccgcccaaatgcggagcttaccgcctgcgtcattacccagggccacattcttggccaattgcaagccatcaaca aagcccgccaagagtttctgctacgaaagggacgggggggtttacttggacccccagtccggcgaggagctcaacccaatccccccgccgcc gcagccctatcagcagcagccgcgggccccttgcttcccaggatggcacccaaaaagaagctgcagctgccgccgccacccacggacgag gaggaatactgggacagtcaggcagaggaggtttttggacgaggaggaggaggacatgatggaagactgggagagcctagacgaggaag cttccgaggtcgaagaggtgtcagacgaaacaccgtcaccctcggtcgcattcccctcgccggcgccccagaaatcggcaaccggttccag catggctacaacctccgctcctcaggcgccgccggcactgcccgttcgccgacccaaccgtagatgggacaccactggaaccagggccgg taagtccaagcagccgccgccgttagcccaagagcaacaacagcgccaaggctaccgctcatggcgcgggcacaagaacgccatagttgc ttgcttgcaagactgtgggggcaacatctccttcgcccgccgctttcttctctaccatcacggcgtggccttcccccgtaacatcctgcattactac cgtcatctctacagcccatactgcaccggcgggcagcggcagcggcagcaacagcagcggccacacagaagcaaaggcgaccggatagc aagactctgacaaagcccaagaaatccacagcggcggcagcagcaggaggaggagcgctgcgtctggcgcccaacgaacccgtatcgac ccgcgagcttagaaacaggatttttcccactctgtatgctatatttcaacagagcagggggccaagaacaagagctgaaaataaaaaacaggtct ctgcgatccctcacccgcagctgcctgtatcacaaaagcgaagatcagcttcggcgcacgctggaagacgcggaggctctcttcagtaaatac tgcgcgctgactcttaaggactagtttcgcgccctttctcaaatttaagcgcgaaaactacgtcatctccagcggccacacccggcgccagcac ctgtcgtcagcgccattatgagcaaggaaattcccacgccctacatgtggagttaccagccacaaatgggacttgcggctggagctgcccaag actactcaacccgaataaactacatgagcgcgggacccccacatgatatcccgggtcaacggaatccgcgcccaccgaaaccgaattctcttg gaacaggcggctattaccaccacacctcgtaataaccttaatccccgtagttggcccgctgccctggtgtaccaggaaagtcccgctcccacc actgtggtacttcccagagacgcccaggccgaagttcagatgactaactcaggggcgcagcttgcgggcggctttcgtcacagggtgcggtc gcccgggcagggtataactcacctgacaatcagagggcgaggtattcagctcaacgacgagtcggtgagctcctcgcttggtctccgtccgg acgggacatttcagatcggcggcgccggccgtccttcattcacgcctcgtcaggcaatcctaactctgcagacctcgtcctctgagccgcgctc tggaggcattggaactctgcaatttattgaggagtttgtgccatcggtctactttaaccccttctcgggacctcccggccactatccggatcaatttta ttcctaactttgacgcggtaaaggactcggcggacggctacgactgaatgttaagtggagaggcagagcaactgcgcctgaaacacctggtc cactgtcgccgccacaagtgctttgcccgcgactccggtgagttttgctactttgaattgcccgaggatcatatcgagggcccggcgcacggc gtccggcttaccgcccagggagagcttgcccgtagcctgattcgggagtttacccagcgcccctgctagttgagcgggacaggggaccctg tgttctcactgtgatttgcaactgtcctaaccttggattacatcaagatcctctagttataactagagtacccggggatcttattcccttttaactaataa aaaaaaataataaagcatcacttacttaaaatcagttagcaaatttctgtccagtttattcagcagcacctccttgccctcctcccagctctggtattg cagcttcctcctggctgcaaactttctccacaatctaaatggaatgtcagtttcctcctgttcctgtccatccgcacccactatcttcatgttgttgcag atgaagcgcgcaagaccgtctgaagataccttcaacccgtgtatccatatgacacggaaaccggtcctccaactgtgcctttctcttactcctccc tttgtatcccccaatgggtttcaagagagtcccctggggtactctctttgcgcctatccgaacctctagttacctccaatggcatgcttgcgctcaa aatgggcaacggcctctctctggacgaggccggcaaccttacctcccaaaatgtaaccactgtgagcccacctctcaaaaaaaccaagtcaaa
```

-continued

```
cataaacctggaaatatctgcacccctcacagttacctcagaagccctaactgtggctgccgccgcacctctaatggtcgcgggcaacacactc accatgcaatcacaggccccgctaaccgtgcacgactccaaacttagcattgccacccaaggacccctcacagtgtcagaaggaaagctagc cctgcaaacatcaggcccctcaccaccaccgatagcagtacccttactatcactgcctcaccccctctaactactgccactggtagcttgggc attgacttgaaagagcccatttatacacaaaatggaaaactaggactaaagtacggggctcctttgcatgtaacagacgacctaaacactttgac cgtagcaactggtccaggtgtgactattaataatacttccttgcaaactaaagttactggagccttgggttttgattcacaaggcaatatgcaactta atgtagcaggaggactaaggattgattctcaaaacagacgccttatacttgatgttagttatccgtttgatgctcaaaaccaactaaatctaagact aggacagggccctcttttttataaactcagcccacaacttggatattaactacaacaaaggcctttacttgtttacagcttcaaacaattccaaaaag cttgaggttaacctaagcactgccaagggggttgatgtttgacgctacagccatagccattaatgcaggagatgggcttgaatttggttcacctaat gcaccaaacacaaatcccctcaaaacaaaaattggccatggcctagaatttgattcaaacaaggctatggttcctaaactaggaactggccttag ttttgacagcacaggtgccattacagtaggaaacaaaaataatgataagctaactttgtggaccacaccagctccatctcctaactgtagactaaa tgcagagaaagatgctaaactcactttggtcttaacaaaatgtggcagtcaaatacttgctacagtttcagttttggctgttaaaggcagtttggctc caatatctggaacagttcaaagtgctcatcttattataagatttgacgaaatggagtgctactaaacaattccttcctggacccagaatattggaac tttagaaatggagatcttactgaaggcacagcctatacaaacgctgttggatttatgcctaacctatcagcttatccaaaatctcacggtaaaactg ccaaagtaacattgtcagtcaagtttacttaaacggagacaaaactaaacctgtaacactaaccattacactaaacggtacacaggaaacagg agacacaactccaagtgcatactctatgtcattttcatgggactggtctggccacaactacattaatgaaatatttgccacatcctcttacacttttttca tacattgcccaagaataaagaatcgtttgtgttatgtttcaacgtgtttattttttcaattgcagaaaatttcaagtcattttttcattcagtagtatagc cccaccaccacatagcttatacagatcaccgtaccttaatcaaactcacagaaccctagtattcaacctgccacctccctcccaacacacagagtaca cagtcctttctccccggctggccttaaaaagcatcatatcatgggtaacagacatattcttaggtgttatattccacacggtttcctgtcgagccaaa cgctcatcagtgatattaataaactccccgggcagctcacttaagttcatgtcgctgtccagctgctgagccacaggctgctgtccaacttgcggt tgcttaacgggcggcgaaggagaagtccacgcctacatgggggtagagtcataatcgtgcatcaggatagggcggtggtgctgcagcagcg cgcgaataaactgctgccgccgccgctccgtcctgcaggaatacaacatggcagtggtctcctcagcgatgattcgcaccgcccgcagcata aggcgccttgtcctccgggcacagcagcgcaccctgatctcacttaaatcagcacagtaactgcagcacagcaccacaatattgttcaaaatcc cacagtgcaaggcgctgtatccaaagctcatggcggggaccacagaacccacgtggccatcataccacaagcgcaggtagattaagtggcg acccctcataaacacgctggacataaacattacctcttttggcatgttgtaattcaccacctcccggtaccatataaacctctgattaaacatggcg ccatccaccaccatcctaaaccagctggccaaaacctgcccgccggctatacactgcagggaaccgggactggaacaatgacagtggaga gcccaggactcgtaaccatggatcatcatgctcgtcatgatatcaatgttggcacaacacaggcacacgtgcatacacttcctcaggattacaag ctcctcccgcgttagaaccatatcccagggaacaacccattcctgaatcagcgtaaatcccacactgcagggaagacctcgcacgtaactcac gttgtgcattgtcaaagtgttacattcgggcagcagcggatgatcctccagtatggtagcgcgggtttctgtctcaaaaggaggtagacgatccc tactgtacggagtgcgccgagacaaccgagatcgtgttggtcgtagtgtcatgccaaatggaacgccggacgtagtcatatttcctgaagcaaa accaggtgcgggcgtgacaaacagatctgcgtctccggtctcgccgcttagatcgctctgtgtagtagttgtagtatatccactctctcaaagcat ccaggcgccccctggcttcgggttctatgtaaactccttcatgcgccgctgccctgataacatccaccaccgcagaataagccacacccagcc aacctacacattcgttctgcgagtcacacacgggaggagcgggaagagctggaagaaccatgttttttttttttattccaaaagattatccaaaacc tcaaaatgaagatctattaagtgaacgcgctcccctccggtggcgtggtcaaactctacagccaaagaacagataatggcatttgtaagatgttg cacaatggcttccaaaaggcaaacggccctcacgtccaagtggacgtaaaggctaaacccttcagggtgaatctcctctataaacattccagca ccttcaaccatgcccaaataattctcatctcgccaccttctcaatatatctctaagcaaatcccgaatattaagtccggccattgtaaaaatctgctcc agagcgccctccaccttcagcctcaagcagcgaatcatgattgcaaaaattcaggttcctcacagacctgtataagattcaaaagcggaacatt aacaaaaataccgcgatcccgtaggtcccttcgcagggccagctgaacataatcgtgcaggtctgcacggaccagcgcggccacttcccctg ccaggaaccttgacaaaagaacccacactgattatgacacgcatactcggagctatgctaaccagcgtagccccgatgtaagctttgttgcatg ggcggcgatataaaatgcaaggtgctgctcaaaaaatcaggcaaagcctcgcgcaaaaaagaaagcacatcgtagtcatgctcatgcagata aaggcaggtaagctccggaaccaccacagaaaaagacaccattttttctctcaaacatgtctgcgggtttctgcataaacacaaaataaaataac aaaaaaacatttaaacattagaagcctgtcttacaacaggaaaaacaacccttataagcataagacggactacggccatgccggcgtgaccgt
```

-continued

```
aaaaaaactggtcaccgtgattaaaaagcaccaccgacagctcctcggtcatgtccggagtcataatgtaagactcggtaaacacatcaggttg attcatcggtcagtgctaaaaagcgaccgaaatagcccgggggaatacatacccgcaggcgtagagacaacattacagccccataggagg tataacaaaattaataggagagaaaaacacataaacacctgaaaaaccctcctgcctaggcaaaatagcaccctcccgctccagaacaacata cagcgcttcacagcggcagcctaacagtcagccttaccagtaaaaaagaaaacctattaaaaaaacaccactcgacacggcaccagctcaat cagtcacagtgtaaaaaagggccaagtgcagagcgagtatatataggactaaaaaatgacgtaacggttaaagtccacaaaaaacacccaga aaaccgcacgcgaacctacgcccagaaacgaaagccaaaaaacccacaacttcctcaaatcgtcacttccgtttccccacgttacgtaacttcc cattttaagaaaactacaattcccaacacatacaagttactccgccctaaaacctacgtcacccgccccgttcccacgccccgcgccacgtcac aaactccacccctcattatcatattggcttcaatccaaaataaggtatattattgatgatnnn
```

15

REFERENCES

All references, including publications, patent applications, and patents, cited herein are hereby incorporated by reference to the same extent as if each reference were individually and specifically indicated to be incorporated by reference and were set forth in its entirety herein.

1. Lee, C. S., Bishop, E. S., Zhang, R., Yu, X., Farina, E. M., Yan, S., Zhao, C., Zheng, Z., Shu, Y., Wu, X. et al. (2017) Adenovirus-Mediated Gene Delivery: Potential Applications for Gene and Cell-Based Therapies in the New Era of Personalized Medicine. *Genes Dis,* 4, 43-63.

2. Breyer, B., Jiang, W., Cheng, H., Zhou, L., Paul, R., Feng, T. and He, T. C. (2001) Adenoviral vector-mediated gene transfer for human gene therapy. *Curr Gene Ther,* 1, 149-162.

3. Crystal, R. G. (2014) Adenovirus: the first effective in vivo gene delivery vector. *Hum Gene Ther,* 25, 3-11.

4. Ehrke-Schulz, E., Zhang, W., Gao, J. and Ehrhardt, A. (2017) Recent Advances in Preclinical Developments Using Adenovirus Hybrid Vectors. *Hum Gene Ther,* 28, 833-841.

5. Maggio, I., Stefanucci, L., Janssen, J. M., Liu, J., Chen, X., Mouly, V. and Goncalves, M. A. (2016) Selection-free gene repair after adenoviral vector transduction of designer nucleases: rescue of dystrophin synthesis in DMD muscle cell populations. *Nucleic Acids Res,* 44, 1449-1470.

6. Graham, F. L. and Prevec, L. (1995) Methods for construction of adenovirus vectors. *Molecular biotechnology,* 3, 207-220.

7. Mizuguchi, H. and Kay, M. A. (1998) Efficient construction of a recombinant adenovirus vector by an improved in vitro ligation method. *Hum Gene Ther,* 9, 2577-2583.

8. Hardy, S., Kitamura, M., Harris Stansil, T., Dai, Y. M. and Phipps, M. L. (1997) Construction of adenovirus vectors through Cre-lox recombination. *Journal of Virology,* 71, 1842-1849.

9. Ng, P., Parks, R. J., Cummings, D. T., Evelegh, C. M., Sankar, U. and Graham, F. L. (1999) A high-efficiency Cre/loxP-based system for construction of adenoviral vectors. *Hum Gene Ther,* 10, 2667-2672.

10. Ketner, G., Spencer, F., Tugendreich, S., Connelly, C. and Hieter, P. (1994) Efficient manipulation of the human adenovirus genome as an infectious yeast artificial chromosome clone. *Proceedings of the National Academy of Sciences of the United States of America,* 91, 6186-6190.

11. Chartier, C., Degryse, E., Gantzer, M., Dieterle, A., Pavirani, A. and Mehtali, M. (1996) Efficient generation of recombinant adenovirus vectors by homologous recombination in *Escherichia coli. J Virol,* 70, 4805-4810.

12. He, T. C., Zhou, S., da Costa, L. T., Yu, J., Kinzler, K. W. and Vogelstein, B. (1998) A simplified system for generating recombinant adenoviruses. *Proceedings of the National Academy of Sciences of the United States of America,* 95, 2509-2514.

13. Luo, J., Deng, Z. L., Luo, X., Tang, N., Song, W. X., Chen, J., Sharff, K. A., Luu, H. H., Haydon, R. C., Kinzler, K. W. et al. (2007) A protocol for rapid generation of recombinant adenoviruses using the AdEasy system. *Nature protocols,* 2, 1236-1247.

14. Gibson, D. G., Young, L., Chuang, R. Y., Venter, J. C., Hutchison, C. A., 3rd and Smith, H. O. (2009) Enzymatic assembly of DNA molecules up to several hundred kilobases. *Nat Methods,* 6, 343-345.

15. Gibson, D. G. (2011) Enzymatic assembly of overlapping DNA fragments. *Methods Enzymol,* 498, 349-361.

16. Lienert, F., Lohmueller, J. J., Garg, A. and Silver, P. A. (2014) Synthetic biology in mammalian cells: next generation research tools and therapeutics. *Nat Rev Mol Cell Biol,* 15, 95-107.

17. Wu, N., Zhang, H., Deng, F., Li, R., Zhang, W., Chen, X., Wen, S., Wang, N., Zhang, J., Yin, L. et al. (2014) Overexpression of Ad5 precursor terminal protein accelerates recombinant adenovirus packaging and amplification in HEK-293 packaging cells. *Gene Ther,* 21, 629-637.

18. Wei, Q., Fan, J., Liao, J., Zou, Y., Song, D., Liu, J., Cui, J., Liu, F., Ma, C., Hu, X. et al. (2017) Engineering the Rapid Adenovirus Production and Amplification (RAPA) Cell Line to Expedite the Generation of Recombinant Adenoviruses. *Cellular physiology and biochemistry international journal of experimental cellular physiology, biochemistry, and pharmacology,* 41, 2383-2398.

19. Hu, X., Li, L., Yu, X., Zhang, R., Yan, S., Zeng, Z., Shu, Y., Zhao, C., Wu, X., Lei, J. et al. (2017) CRISPR/Cas9-mediated reversibly immortalized mouse bone marrow stromal stem cells (BMSCs) retain multipotent features of mesenchymal stem cells (MSCs). *Oncotarget,* 8, 111847-111865.

20. Huang, X., Chen, Q., Luo, W., Pakvasa, M., Zhang, Y., Zheng, L., Li, S., Yang, Z., Zeng, H., Liang, F. et al. (2020) SATB2: A versatile transcriptional regulator of craniofacial and skeleton development, neurogenesis and tumorigenesis, and its applications in regenerative medicine. *Genes & Diseases.*

21. Wu, X., Li, Z., Zhang, H., He, F., Qiao, M., Luo, H., Zhang, J., Zhang, M., Mao, Y., Wagstaff, W. et al. (2021) Modeling colorectal tumorigenesis using the organoids derived from conditionally immortalized mouse intestinal crypt cells (ciMICs). *Genes & Diseases.*

22. Wang, X., Zhao, L., Wu, X., Luo, H., Wu, D., Zhang, M., Zhang, J., Pakvasa, M., Wagstaff, W., He, F. et al. (2021)

Development of a simplified and inexpensive RNA depletion method for plasmid DNA purification using size selection magnetic beads (SSMBs). *Genes Dis,* 8, 298-306.

23. He, T.-C. (2004), *Adenoviral Vectors in Current Protocols in Human Genetics.* John Wiley & Sons, Inc., New York, Vol. Unit 12.4, pp. 12.14.11-12.14.25.

24. Deng, F., Chen, X., Liao, Z., Yan, Z., Wang, Z., Deng, Y., Zhang, Q., Zhang, Z., Ye, J., Qiao, M. et al. (2014) A simplified and versatile system for the simultaneous expression of multiple siRNAs in mammalian cells using Gibson DNA Assembly. *PloS one,* 9, e113064.

25. Mao, Y., Ni, N., Huang, L., Fan, J., Wang, H., He, F., Liu, Q., Shi, D., Fu, K., Pakvasa, M. et al. (2021) Argonaute (AGO) proteins play an essential role in mediating BMP9-induced osteogenic signaling in mesenchymal stem cells (MSCs). *Genes & Diseases.*

26. Fan, J., Feng, Y., Zhang, R., Zhang, W., Shu, Y., Zeng, Z., Huang, S., Zhang, L., Huang, B., Wu, D. et al. (2020) A simplified system for the effective expression and delivery of functional mature microRNAs in mammalian cells. *Cancer Gene Ther,* 27, 424-437.

27. Fan, J., Wei, Q., Liao, J., Zou, Y., Song, D., Xiong, D., Ma, C., Hu, X., Qu, X., Chen, L. et al. (2017) Noncanonical Wnt signaling plays an important role in modulating canonical Wnt-regulated stemness, proliferation and terminal differentiation of hepatic progenitors. *Oncotarget,* 8, 27105-27119.

28. Li, R., Zhang, W., Cui, J., Shui, W., Yin, L., Wang, Y., Zhang, H., Wang, N., Wu, N., Nan, G. et al. (2014) Targeting BMP9-promoted human osteosarcoma growth by inactivation of notch signaling. *Curr Cancer Drug Targets,* 14, 274-285.

29. Cao, D., Lei, Y., Ye, Z., Zhao, L., Wang, H., Zhang, J., He, F., Huang, L., Shi, D., Liu, Q. et al. (2020) Blockade of IGF/IGF-1R signaling axis with soluble IGF-1R mutants suppresses the cell proliferation and tumor growth of human osteosarcoma. *American journal of cancer research,* 10, 3248-3266.

30. Zhao, C., Wu, N., Deng, F., Zhang, H., Wang, N., Zhang, W., Chen, X., Wen, S., Zhang, J., Yin, L. et al. (2014) Adenovirus-mediated gene transfer in mesenchymal stem cells can be significantly enhanced by the cationic polymer polybrene. *PloS one,* 9, e92908.

31. Zhang, B., Yang, L., Zeng, Z., Feng, Y., Wang, X., Wu, X., Luo, H., Zhang, J., Zhang, M., Pakvasa, M. et al. (2020) Leptin Potentiates BMP9-Induced Osteogenic Differentiation of Mesenchymal Stem Cells Through the Activation of JAK/STAT Signaling. *Stem Cells Dev,* 29, 498-510.

32. Luo, W., Zhang, L., Huang, B., Zhang, H., Zhang, Y., Zhang, F., Liang, P., Chen, Q., Cheng, Q., Tan, D. et al. (2021) BMP9-initiated osteogenic/odontogenic differentiation of mouse tooth germ mesenchymal cells (TGMCS) requires Wnt/beta-catenin signalling activity. *J Cell Mol Med,* 25, 2666-2678.

33. He, F., Ni, N., Zeng, Z., Wu, D., Feng, Y., Li, A. J., Luu, B., Li, A. F., Qin, K., Wang, E. et al. (2020) FAMSi: A Synthetic Biology Approach to the Fast Assembly of Multiplex siRNAs for Silencing Gene Expression in Mammalian Cells. *Mol Ther Nucleic Acids,* 22, 885-899.

34. Zhang, Z., Liu, J., Zeng, Z., Fan, J., Huang, S., Zhang, L., Zhang, B., Wang, X., Feng, Y., Ye, Z. et al. (2019) lncRNA Rmst acts as an important mediator of BMP9-induced osteogenic differentiation of mesenchymal stem cells (MSCs) by antagonizing Notch-targeting microRNAs. *Aging* (Albany NY), 11, 12476-12496.

35. Kang, Q., Sun, M. H., Cheng, H., Peng, Y., Montag, A. G., Deyrup, A. T., Jiang, W., Luu, H. H., Luo, J., Szatkowski, J. P. et al. (2004) Characterization of the distinct orthotopic boneforming activity of 14 BMPs using recombinant adenovirus-mediated gene delivery. *Gene Ther,* 11, 1312-1320.

36. Li, R., Zhang, W., Yan, Z., Liu, W., Fan, J., Feng, Y., Zeng, Z., Cao, D., Haydon, R. C., Luu, H. H. et al. (2021) Long non-coding RNA (LncRNA) HOTAIR regulates BMP9-induced osteogenic differentiation by targeting the proliferation of mesenchymal stem cells (MSCs). *Aging* (Albany N. Y.), 13, 4199-4214.

37. Chen, L., Jiang, W., Huang, J., He, B. C., Zuo, G. W., Zhang, W., Luo, Q., Shi, Q., Zhang, B. Q., Wagner, E. R. et al. (2010) Insulin-like growth factor 2 (IGF-2) potentiates BMP-9-induced osteogenic differentiation and bone formation. *J Bone Miner Res,* 25, 2447-2459.

38. Yan, S., Zhang, R., Wu, K., Cui, J., Huang, S., Ji, X., An, L., Yuan, C., Gong, C., Zhang, L. et al. (2018) Characterization of the essential role of bone morphogenetic protein 9 (BMP9) in osteogenic differentiation of mesenchymal stem cells (MSCs) through RNA interference. *Genes Dis,* 5, 172-184.

39. Song, D., Zhang, F., Reid, R. R., Ye, J., Wei, Q., Liao, J., Zou, Y., Fan, J., Ma, C., Hu, X. et al. (2017) BMP9 induces osteogenesis and adipogenesis in the immortalized human cranial suture progenitors from the patent sutures of craniosynostosis patients. *J Cell Mol Med,* 21, 2782-2795.

40. Ye, J., Wang, J., Zhu, Y., Wei, Q., Wang, X., Yang, J., Tang, S., Liu, H., Fan, J., Zhang, F. et al. (2016) A thermoresponsive polydiolcitrate-gelatin scaffold and delivery system mediates effective bone formation from BMP9-transduced mesenchymal stem cells. *Biomed Mater,* 11, 025021.

41. Zhang, H., Wang, J., Deng, F., Huang, E., Yan, Z., Wang, Z., Deng, Y., Zhang, Q., Zhang, Z., Ye, J. et al. (2015) Canonical Wnt signaling acts synergistically on BMP9-induced osteo/odontoblastic differentiation of stem cells of dental apical papilla (SCAPs). *Biomaterials,* 39, 145-154.

42. Cheng, H., Jiang, W., Phillips, F. M., Haydon, R. C., Peng, Y., Zhou, L., Luu, H. H., An, N., Breyer, B., Vanichakarn, P. et al. (2003) Osteogenic activity of the fourteen types of human bone morphogenetic proteins (BMPs). *J Bone Joint Surg Am,* 85, 1544-1552.

43. Mostafa, S., Pakvasa, M., Coalson, E., Zhu, A., Alverdy, A., Castillo, H., Fan, J., Li, A., Feng, Y., Wu, D. et al. (2019) The wonders of BMP9: From mesenchymal stem cell differentiation, angiogenesis, neurogenesis, tumorigenesis, and metabolism to regenerative medicine. *Genes Dis,* 6, 201-223.

44. Liu, W., Deng, Z., Zeng, Z., Fan, J., Feng, Y., Wang, X., Cao, D., Zhang, B., Yang, L., Liu, B. et al. (2020) Highly expressed BMP9/GDF2 in postnatal mouse liver and lungs may account for its pleiotropic effects on stem cell differentiation, angiogenesis, tumor growth and metabolism. *Genes Dis,* 7, 235-244.

45. Zhang, L., Luo, Q., Shu, Y., Zeng, Z., Huang, B., Feng, Y., Zhang, B., Wang, X., Lei, Y., Ye, Z. et al. (2019) Transcriptomic landscape regulated by the 14 types of bone morphogenetic proteins (BMPs) in lineage commitment and differentiation of mesenchymal stem cells (MSCs). *Genes Dis,* 6, 258-275.

The invention claimed is:

1. A gene transfer vector comprising (i) all or part of a viral genome, wherein the viral genome does not comprise an E1 region and (ii) a suicide gene flanked by a first cloning nucleic acid sequence and a second cloning nucleic acid sequence, wherein the first cloning nucleic acid sequence comprises SEQ ID NO: 1 (AATCG-GAAAGCGGACGCGGA) and the second cloning nucleic acid sequence comprises SEQ ID NO: 2 (CGAGTATCCCGTGAGCGCTT).

2. The gene transfer vector of claim 1, wherein the viral genome is an adenovirus genome.

3. The gene transfer vector of claim 2, wherein the adenovirus is serotype 5.

4. The gene transfer vector of claim 1, wherein the suicide gene is a bacterial suicide gene.

5. The gene transfer vector of claim 4, wherein the bacterial suicide gene is a ccdB gene.

6. A composition comprising the gene transfer vector of claim 1 and a pharmaceutically acceptable carrier.

7. A system for producing an adenoviral vector, which comprises:
   (a) a vector comprising (i) all or part of an adenoviral genome, wherein the viral genome does not comprise an E1 region and (ii) a suicide gene flanked by a first cloning nucleic acid sequence and a second cloning nucleic acid sequence, wherein the first cloning nucleic acid sequence comprises SEQ ID NO: 1 (AATCG-GAAAGCGGACGCGGA) and the second cloning nucleic acid sequence comprises SEQ ID NO: 2 (CGAGTATCCCGTGAGCGCTT) wherein the first and second cloning nucleic acid sequences are different;
   (b) a transgene flanked by the first cloning nucleic acid sequence and the second cloning nucleic acid sequence; and
   (c) reagents for isothermal DNA assembly.

8. The system of claim 7, wherein the adenovirus is serotype 5.

9. The system of claim 7, wherein the suicide gene is a bacterial suicide gene.

10. The system of claim 9, wherein the bacterial suicide gene is a ccdB gene.

11. A method of producing an adenoviral vector comprising contacting a cell with the system of claim 7.

* * * * *

SEQUENCE LISTING

Sequence total quantity: 12
SEQ ID NO: 1            moltype = DNA   length = 20
FEATURE                 Location/Qualifiers
source                  1..20
                        mol_type = other DNA
                        organism = synthetic construct
SEQUENCE: 1
aatcggaaag cggacgcgga                                                     20

SEQ ID NO: 2            moltype = DNA   length = 20
FEATURE                 Location/Qualifiers
source                  1..20
                        mol_type = other DNA
                        organism = synthetic construct
SEQUENCE: 2
cgagtatccc gtgagcgctt                                                     20

SEQ ID NO: 3            moltype = DNA   length = 54
FEATURE                 Location/Qualifiers
source                  1..54
                        mol_type = other DNA
                        organism = synthetic construct
SEQUENCE: 3
gatccaatcg gaaagcggac gcggaattta aatcgagtat cccgtgagcg cttt       54

SEQ ID NO: 4            moltype = DNA   length = 54
FEATURE                 Location/Qualifiers
source                  1..54
                        mol_type = other DNA
                        organism = synthetic construct
SEQUENCE: 4
ctagaaagcg ctcacgggat actcgattta aattccgcgt ccgctttccg attg       54

SEQ ID NO: 5            moltype = DNA   length = 55
FEATURE                 Location/Qualifiers
source                  1..55
                        mol_type = other DNA
                        organism = synthetic construct
SEQUENCE: 5
aatcggaaag cggacgcgga atttaccacc atggagagcg acgacagcgg ccatg      55

SEQ ID NO: 6            moltype = DNA   length = 46
FEATURE                 Location/Qualifiers
source                  1..46
                        mol_type = other DNA
                        organism = synthetic construct
SEQUENCE: 6
aagcgctcac gggatactcg atttagcgag atccggtgga gccggg                46

SEQ ID NO: 7            moltype = DNA   length = 60
FEATURE                 Location/Qualifiers
source                  1..60
                        mol_type = other DNA
                        organism = synthetic construct
SEQUENCE: 7
aatcggaaag cggacgcgga atttaccacc atgggcatgc atatgtcccc tggggccttc  60

SEQ ID NO: 8            moltype = DNA   length = 50
FEATURE                 Location/Qualifiers
source                  1..50
                        mol_type = other DNA
                        organism = synthetic construct
SEQUENCE: 8
aagcgctcac gggatactcg atttctacct acacccacac tcagccacac             50

SEQ ID NO: 9            moltype = DNA   length = 24
FEATURE                 Location/Qualifiers
source                  1..24
                        mol_type = other DNA
                        organism = synthetic construct
SEQUENCE: 9
aatcggaaag cggacgcgga attt                                         24

SEQ ID NO: 10           moltype = DNA   length = 24
FEATURE                 Location/Qualifiers
source                  1..24
                        mol_type = other DNA
                        organism = synthetic construct

```
SEQUENCE: 10
aagcgctcac gggatactcg attt                                                      24

SEQ ID NO: 11          moltype = DNA   length = 37894
FEATURE                Location/Qualifiers
source                 1..37894
                       mol_type = other DNA
                       organism = synthetic construct
SEQUENCE: 11
nnttaattaa ggatccnnnc ctgtcctcga ccgatgccct tgagagcctt caacccagtc        60
agctccttcc ggtgggcgcg gggcatgact atcgtcgccg cacttatgac tgtcttcttt       120
atcatgcaac tcgtaggaca ggtgccggca gcgctctggg tcattttcgg cgaggaccgc       180
tttcgctgga gcgcgacgat gatcggcctg tcgcttgcgg tattcggaat cttgcacgcc       240
ctcgctcaag ccttcgtcac tggtcccgcc accaaacgtt tcggcgagaa gcaggccatt       300
atcgccggca tggcggccga cgcgctgggc tacgtcttgc tggcgttcgc gacgcgaggc       360
tggatggcct tccccattat gattcttctc gcttccggcg gcatcgggat gcccgcgttg       420
caggccatgc tgtccaggca ggtagatgac gaccatcagg gacagcttca aggatcgctc       480
gcggctctta ccagcctaac ttcgatcact ggaccgctga tcgtcacggc gatttatgcc       540
gcctcggcga gcacatggaa cggggttggca tggattgtag gcgccgccct ataccttgtc       600
tgcctccccg cgttgcgtcg cggtgcatgg agccgggcca cctcgacctg aatggaagcc       660
ggcggcacct cgctaacgga ttcaccactc caagaattgg agccaatcaa ttcttgcgga       720
gaactgtgaa tgcgcaaacc aacccttggc agaacatatc catcgcgtcc gccatctcca       780
gcagccgcac gcggcgcatc tcgggcagcg ttgggtcctg gccacggggtg cgcatgatcg       840
tgctcctgtc gttgaggacc cggctaggct ggcggggttg ccttactggt tagcagaatg       900
aatcaccgat acgcgagcga acgtgaagcg actgctgctg caaaacgtct gcgacctgag       960
caacaacatg aatggtcttc ggtttccgtg tttcgtaaag tctggaaacg cggaagtcag      1020
cgccctgcac cattatgttc cggatctgca tcgcaggatg ctgctggcta ccctgtggaa      1080
cacctacatc tgtattaacg aagcgctggc attgaccctg agtgatttt ctctggtccc      1140
gccgcatcca taccgccagt tgtttaccct cacaacgttc cagtaaccgg gcatgttcat      1200
catcagtaac ccgtatcgtg agcatcctct ctcgtttcat cggtatcatt accccatga      1260
acagaaattc cccttacac ggaggcatca agtgaccaaa caggaaaaaa ccgcccttaa      1320
catggccgc tttatcagaa gccagacatt aacgcttctg gagaaactca acgagctgga      1380
cgcggatgaa caggcagaca tctgtgaatc gcttcacgac cacgctgatg agctttaccg      1440
cagctgcctc gcgcgtttcg gtgatgacgg tgaaaacctc tgacacatgc agctcccgga      1500
gacggtcaca gcttgtctgt aagcggatgc cgggagcaga caagcccgtc agggcgcgtc      1560
agcgggtgtt ggcgggtgtc ggggcgcagc catgacccag tcacgtagcg atagcggagt      1620
gtatactggc ttaactatgc ggcatcagag cagattgtac tgagagtgca ccatatgcgg      1680
tgtgaaatac cgcacagatg cgtaaggaga aaataccgca tcaggcgctc ttccgcttcc      1740
tcgctcactg actcgctgcg ctcggtcgtt cggctgcggc gagcggtatc agctcactca      1800
aaggcggtaa tacggttatc cacagaatca ggggataacg caggaaagaa catgtgagca      1860
aaaggccagc aaaaggccag gaaccgtaaa aaggccgcgt tgctggcgtt tttccatagg      1920
ctccgccccc ctgacgagca tcacaaaaat cgacgctcaa gtcagaggtg gcgaaacccg      1980
acaggactat aaagatacca ggcgtttccc cctggaagct ccctcgtgcg ctctcctgtt      2040
ccgaccctgc cgcttaccgg atacctgtcc gcctttctcc cttcgggaag cgtggcgctt      2100
tctcaatgct cacgctgtag gtatctcagt tcggtgtagg tcgttcgctc caagctgggc      2160
tgtgtgcacg aacccccgt tcagcccgac cgctgcgcct tatccggtaa ctatcgtctt      2220
gagtccaacc cggtaagaca cgacttatcg ccactggcag cagccactgg taacaggatt      2280
agcagagcga ggtatgtagg cggtgctaca gagttcttga agtggtggcc taactacggc      2340
tacactagaa ggacagtatt tggtatctgc gctctgctga agccagttac cttcggaaaa      2400
agagttggta gctcttgatc cggcaaacaa accaccgctg gtagcggtgg tttttttgtt      2460
tgcaagcagc agattacgcg cagaaaaaaa ggatctcaag aagatccttt gatcttttct      2520
acggggtctg acgctcagtg gaacgaaaac tcacgttaag ggattttggt catgagatta      2580
tcaaaaagga tcttcaccta gatccttta aattaaaaat gaagttttaa atcaatctaa      2640
agtatatatg agtaaacttg gtctgacagt taccaatgct taatcagtga ggcacctatc      2700
tcagcgatct gtctatttcg ttcatccata gttgcctgac tccccgtcgt gtagataact      2760
acgatacggg aggcttacc atctggcccc agtgctgcaa tgataccgcg agacccacgc      2820
tcaccggctc cagatttatc agcaataaac cagccagccg gaagggccga gcgcagaagt      2880
ggtcctgcaa ctttatccgc ctccatccag tctattaatt gttgccggga gctagagta      2940
agtagttcgc cagttaatag tttgcgcaac gttgttgnna aaaaggatct tcacctagat      3000
ccttttcacg tagaaagcca gtccgcagaa acggtgctga ccccggatga atgtcagcta      3060
ctgggctatc tggacaaggg aaaacgcaag cgcaaagaga aagcaggtag cttgcagtgg      3120
gcttacatgg cgatagctag actgggcggt tttatggaca gcaagcgaac cggaattgcc      3180
agctggggcg ccctctggta aggttgggaa gccctgcaaa gtaaactgga tggctttctc      3240
gccgcaagg atctgatggc gcaggggatc aagctctgat caagacacag gatgaggatc      3300
gtttcgcatg attgaacaag atggattgca cgcaggttct ccggccgctt gggtggagag      3360
gctattcggc tatgactggg cacaacagac aatcggctgc tctgatgccg ccgtgttccg      3420
gctgtcagcg caggggcgcc cggttctttt tgtcaagacc gacctgtccg gtgccctgaa      3480
tgaactgcaa gacgaggcag cgcggctatc gtggctggcc acgacgggcg ttccttgcgc      3540
agctgtgctc gacgttgtca ctgaagcggg aagggactgg ctgctattgg gcgaagtgcc      3600
ggggcaggat ctcctgtcat ctcaccttgc tcctgccgag aaagtatcca tcatggctga      3660
tgcaatgcgg cggctgcata cgcttgatcc ggctacctgc ccattcgacc accaagcgaa      3720
acatcgcatc gagcgagcac gtactcggat ggaagccggt cttgtcgatc aggatgatct      3780
ggacgaagag catcaggggc tcgcgccagc cgaactgttc gccaggctca aggcgagcat      3840
gcccgacggc gaggatctcg tcgtgaccca tggcgatgat gctctgcatg gttcgtccga      3900
ggaaaatggc cgcttttctg gattcatcga ctgtggccgg ctgggtgtgg cggaccgcta      3960
tcaggacata gcgttggcta cccgtgatat tgctgaagag cttggcggcg aatgggctga      4020
ccgcttcctc gtgctttacg gtatcgccgc tcccgattcg cagcgcatcg ccttctatcg      4080
ccttcttgac gagttcttct gaattttgtt aaaatttttt ttaaatcagc tcattttta      4140
accaataggc cgaaatcggc aacatccctt ataaatcaaa agaatagacc gcgatagggt      4200
```

-continued

```
tgagtgttgt tccagtttgg aacaagagtc cactattaaa gaacgtggac tccaacgtca  4260
aagggcgaaa aaccgtctat cagggcgatg gcccactacg tgaaccatca cccaaatcaa  4320
gtttttttgcg gtcgaggtgc cgtaaagctc taaatcggaa ccctaaaggg agccccccgat  4380
ttagagcttg acgggggaaag ccggcgaacg tggcgagaaa ggaagggaag aaagcgaaag  4440
gagcgggcgc tagggcgctg gcaagtgtag cggtcacgct gcgcgtaacc accacacccg  4500
cgcgcttaat gcgccgnntt aattaannnn tcccttccag ctctctgccc cttttggatt  4560
gaagccaata tgataatgag ggggtggagt ttgtgacgtg gcgcggggcg tgggaacggg  4620
gcgggtgacg tagtagtgtg gcggaagtgt gatgttgcaa gtgtggcgga acacatgtaa  4680
gcgacggatg tggcaaaagt gacgtttttg gtgtgcgccg gtgtacacag gaagtgacaa  4740
ttttcgcgcg gtttttaggcg gatgttgtag taaatttggg cgtaaccgag taagatttgg  4800
ccattttcgc gggaaaactg aataagagga agtgaaatct gaataatttt gtgttactca  4860
tagcgcgtaa nnncgcgtta agatacattg atgagtttgg acaaaccaca actagaatgc  4920
agtgaaaaaa atgctttatt tgtgaaattt gtgatgctat tgctttattt gtaaccatta  4980
taagctgcaa taaacaagtt aacaacaaca attgcattca ttttatgttt caggttcagg  5040
gggaggtgtg ggaggttttt taaagcaagt aaaacctcta caaatgtggt atggctgatt  5100
atgatcagtt atctagatcc ggtggatctg agtccggact tgtacagctc gtccatgccg  5160
agagtgatcc cggcggcggt cacgaactcc agcaggacca tgtgatcgcg cttctcgttg  5220
gggtcttttgc tcagggcgga ctgggtgctc aggtagtggt tgtcgggcag cagcacgggg  5280
ccgtcgccga tggggggtgtt ctgctggtag tggtcggcga gctgcacgct gccgtcctcg  5340
atgttgtggc ggatcttgaa gttcaccttg atgccgttct tctgcttgtc ggccatgata  5400
tagacgttgt ggctgttgta gttgtactcc agcttgtgcc ccaggatgtt gccgtcctcc  5460
ttgaagtcga tgcccttcag ctcgatgcgg ttcaccaggg tgtcgccctc gaacttcacc  5520
tcggcgcggg tcttgtagtt gccgtcgtcc ttgaagaaga tggtgcgctc ctggacgtag  5580
ccttcgggca tggcggactt gaagaagtcg tgctgcttca tgtggtcggg gtagcggctg  5640
aagcactgca cgccgtaggt cagggtggtc acgaggggtgg gccagggcac gggcagcttg  5700
ccggtcgtgc agatgaactt cagggtcagc ttgccgtagg tggcatcgcc ctcgccctcg  5760
ccggacacgc tgaacttgtg gccgtttacg tcgccgtcca gctcgaccag gatgggcacc  5820
accccggtga acagctcctc gcccttgctc accatggtgg cgaccggtag cgctagcgga  5880
tctgacggtt cactaaacca gctctgctta tatagacctc ccaccgtaca cgcctaccgc  5940
ccatttgcgt caatggggcg gagttgttac gacattttgg aaagtcccgt tgatttttggt  6000
gccaaaacaa actcccattg acgtcaatgg ggtggagact tggaaatccc cgtgagtcaa  6060
accgctatcc acgcccattg atgtactgcc aaaaccgcat caccatggta atagcgatga  6120
ctaatacgta gatgtactgc caagtaggaa agtcccataa ggtcatgtac tgggcataat  6180
gccaggcggg ccatttaccg tcattgacgt caatagggggg cgtacttggc atatgataca  6240
cttgatgtac tgccaagtgg gcagtttacc gtaaatactc cacccattga cgtcaatgga  6300
aagtccctat tggcgttact atgggaacat acgtcattat tgacgtcaat gggcggggggt  6360
cgttgggcgg tcagccaggc gggccattta ccgtaagtta tgtaacgcgg aactccatat  6420
atgggctatg aactaatgac cccgtaattg attactatta nnnctagcag atcctggttc  6480
tttccgcctc agaagccata gagcccaccg catccccagc atgcctgcta ttgtcttccc  6540
aatcctcccc cttgctgtcc tgccccaccc cacccccccag aatagaatga cacctactca  6600
gacaatgcga tgcaatttcc tcattttatt aggaaaggac agtgggagtg gcaccttcca  6660
gggtcaagga aggcacgggg gaggggcaaa caacagatgg ctggcaacta gaaggcacag  6720
tcgaggctga tcagcggggtt tagcgccga tatcatttaa attgattttt gcggtataag  6780
aatatatact gatatgtata cccgaagtat gtcaaaaaga ggtatgctat gaagcagcgt  6840
attacagtga cagttgacag cgacagctat cagttgctca aggcatatat gatgtcaata  6900
tctccggtct ggtaagcaca accatgcaga atgaagcccg tcgtctgcgt gccgaacgct  6960
ggaaagcgaa aaatcaggaa gggatggctg aggtcgccca gtttattgaa atgaacggct  7020
cttttgctga cgagaacagg ggctggtgaa atgcagttta aggtttacac ctataaaaga  7080
gagagccgtt atcgtctgtt tgtggatgta cagagtgata ttattgacac gcccgggcga  7140
cggatggtga tcccccctggc cagtgcacgt ctgctgtcag ataaagtctc ccgtgaactt  7200
tacccggtgg tgcatatcgg ggatgaaagc tggcgcatga tgaccaccga tatggccagt  7260
gtgccggtct ccgttatcgg ggaagaagtg gctgatctca gccaccgcga aaatgacatc  7320
aaaaacgcca ttaacctgat gttctgggga atataaatgt caggctccct tatacacagc  7380
cagtctgcag ctcgctcttc atttaaatcc tgaattcggt gtcttctatg gaggtcaaaa  7440
cagcgtggat ggcgtctcca ggcgatctga cggttcacta aacagctgcg tctctatcac  7500
tgatagggag atctctatca ctgatagggga gatctctatc actgataggg agatctctat  7560
cactgatagg gagagctctg cttatataga cctcccaccg tacacgccta ccgcccattt  7620
gcgtcaatgg ggcggagttg ttacgacatt ttggaaagtc ccgttgattt tggttccaaa  7680
acaaactccc attgacgtca atgggggtgga gacttggaaa ctttgtgagg tcaaaccgct  7740
atccacgccc attgatgtac tgccaaaacc gcatcaccat ggtaatagcg atgactaata  7800
cgtagatgta ctgccaagta ggaaagtccc ataaggtcat gtactgggca taatgccagg  7860
cgggccattt accgtcattg acgtcaatag ggggcgtact ggcatatga tacacttgat  7920
gtactgccaa gtgggcagtt taccgtaaat actccaccca ttgacgtcaa tggaaagtcc  7980
ctattggcgt tactatggga acatacgtca ttattgacgt caatgggcgg  8040
gcggtcagcc aggcgggcca tttaccgtaa gttatgtaac gcggaactcc atatatgggc  8100
tatgaactaa tgaccccgta attgattact attaataact agagnnnnta agggtgggaa  8160
agaatatata aggtggggggt cttatgtagt tttgtatctg ttttgcagca gccgcgccg  8220
ccatgagcgc caactcgttt gatggaagca ttgtgagctc atatttgaca acgcgcatgc  8280
ccccatgggt cgggggtgcgt cagaatgtga tgggctcccag cattgatggt cgccccgtcc  8340
tgcccgcaaa ctctactacc ttgacctacg agaccgtgtc tggaacgccg ttggagactg  8400
cagcctccgc cgccgcttca gccgctgcag ccaccgcccg cgggattgtg actgactttg  8460
ctttcctgag cccgcttgca agcagtgcag cttcccgttc atccgcccgc gatgacaagt  8520
tgacggctct tttggcacaa ttggattctt gacccgggga acttaatgtc gtttctcagc  8580
agctgttgga tctgcgccag caggttctg ccctgaaggc ttcctcccct cccaatgcgg  8640
tttaaaacat aaataaaaaa ccagactctg tttggatttg gatcaagcaa gtgtcttgct  8700
gtctttattt aggggttttg cgcgcgcggt aggcccggga ccagcggtct cggtcgttga  8760
gggtcctgtg tattttttcc aggacgtggt aaaggtgact ctggatgttc agatacatgg  8820
gcataagccc gtctctgggg tggaggtagc accactgcag agcttcatgc tgcggggtgg  8880
tgttgtagat gatccagtcg tagcaggagc gctgggcgtg gtgcctaaaa atgtctttca  8940
```

-continued

```
gtagcaagct gattgccagg ggcaggccct tggtgtaagt gtttacaaag cggttaagct   9000
gggatgggtg catacgtggg gatatgagat gcatcttgga ctgtattttt aggttggcta   9060
tgttcccagc catatccctc cggggattca tgttgtgcag aaccaccagc acagtgtatc   9120
cggtgcactt gggaaatttg tcatgtagct tagaaggaaa tgcgtggaag aacttggaga   9180
cgcccttgtg acctccaaga tttttccatgc attcgtccat aatgatggca atgggcccac   9240
gggcggcggc ctgggcgaag atatttctgg gatcactaac gtcatagttg tgttccagga   9300
tgagatcgtc ataggccatt tttacaaagc gcgggcggag ggtgccagac tgcggtataa   9360
tggttccatc cggcccaggg gcgtagttac cctcacagat ttgcatttcc cacgctttga   9420
gttcagatgg ggggatcatg tctacctgcg gggcgatgaa gaaaacggtt tccggggtag   9480
gggagatcag ctgggaagaa agcaggttcc tgagcagctg cgacttaccg cagccggtgg   9540
gcccgtaaat cacacctatt accgggtgca actggtagtt aagagagctg cagctgccgt   9600
catccctgag caggggggcc acttcgttaa gcatgtccct gactcgcatg ttttccctga   9660
ccaaatccgc cagaaggcgc tcgccgccca gcgatagcac ttcttgcaag gaagcaaagt   9720
ttttcaacgg tttgagaccg tccgccgtag gcatgctttt gagcgtttga ccaagcagtt   9780
ccaggcggtc ccacagctcg gtcacctgct ctacggcatc tcgatccagc atatctcctc   9840
gtttcgcggg ttgggggcggc tttcgctgta cggcagtagt cggtgctcgt ccagacgggc   9900
cagggtcatg tctttccacg ggcgcagggt cctcgtcagc gtagtctggg tcacggtgaa   9960
ggggtgcgct ccgggctgcg cgctggccag ggtgcgcttg aggctggtcc tgctggtgct  10020
gaagcgctgc cggtcttcgc cctgcgcgtc ggccaggtag catttgacca tggtgtcata  10080
gtccagcccc tccgcggcgt ggcccttggc gcgcagcttg cccttggagg aggcgccgca  10140
cgaggggcag tgcagacttt tgagggcgta gagcttgggc gcgagaaata ccgattccgg  10200
ggagtaggca tccgcgccga aggccccgca gacggtctcg cattccacga gccaggtgag  10260
ctctggccgt tcgggggtcaa aaaccaggtt tcccccatgc tttttgatgc gtttcttacc  10320
tctggtttcc atgagccggt gtccacgctc ggtgacgaaa aggctgtccg tgtccccgta  10380
tacagacttg agaggcctgt cctcgagcgg tgttccgcgg tcctcctcgt atagaaactc  10440
ggaccactct gagacaaagg ctcgcgtcca ggccagcacg aaggaggcta agtgggaggg  10500
gtagcggtcg ttgtccacta gggggtccac tcgctccagg gtgtgaagac acatgtcgcc  10560
ctcttcggca tcaaggaagg tgattggttt gtaggtgtag gccacgtgac cgggtgttcc  10620
tgaaggggggg ctataaaagg gggtgggggc gcgttcgtcc tcactctctt ccgcatcgct  10680
gtctgcgagg gccagctgtt ggggtgagta ctccctctga aaagcgggca tgacttctgg  10740
gctaagattg tcagtttcca aaaacgagga ggatttgata ttcacctggc ccgcggtgat  10800
gcctttgagg gtggccgcat ccatctggtc agaaaagaca atcttttgt tgtcaagctt  10860
ggtggcaaac gacccgtaga gggcgttgga cagcaacttg gcgatggagc gcagggtttg  10920
gttttgtcg cgatcggcgc gctccttggc cgcgatgttt agctgcacgt attcgcgcgc  10980
aacgcaccgc cattcgggaa agacggtggt gcgctcgtcg ggcaccaggt gcacgcgcca  11040
accgcggttg tgcagggtga caaggtcaac gctggtggct acctctccgc gtaggcgctc  11100
gttggtccag cagaggcggc cgcccttgcg cgagcagaat ggcggtaggg ggtctagctg  11160
cgtctcgtcc gggggggtctg cgtccacggt aaagaccccg ggcagcaggc gcgcgtcgaa  11220
gtagtctatc ttgcatcctt gcaagtctag cgcctgctgc catgcgcggg cggcaagcgc  11280
gcgctcgtat gggttgagtg ggggacccca tggcatgggg tgggtgagcg cggaggcgta  11340
catgccgcaa atgtcgtaaa cgtagagggg ctctctgagt attccaagat atgtaggggta  11400
gcatcttcca ccgcggatgc tggcgcgcac gtaatcgtat agttcgtgcg agggagcgag  11460
gaggtcgagg ccgaggttgc tacgggcggg ctgctctgct cggaagacta tctgcctgaa  11520
gatggcatgt gagttggatg atatggttgg acgctggaag acgttgaagc tggcgtctgt  11580
gagacctacc gcgtcacgca cgaaggaggc gtaggagtcg cgcagcttgt tgaccagctc  11640
ggcggtgacc tgcacgtcta gggcgcagta gtccaggggt tccttgatga tgtcatactt  11700
atcctgtccc ttttttttcc acagctcgcg gttgaggaca aactcttcgc ggtcttttcca  11760
gtactcttgg atcggaaacc cgtcggcctc cgaacggtaa gagcctagca tgtagaactg  11820
gttgacggcc tggtaggcgc agcatccctt ttctacgggt agcgcgtatg cctgcgcggc  11880
cttccggagc gaggtgtggg tgagcgcaaa ggtgtccctg accatgactt tgaggtactg  11940
gtatttgaag tcagtgtcgt cgcatccgcc ctgctcccag agcaaaaagt ccgtgcgctt  12000
tttggaacgc ggatttggca gggcgaaggt gacatcgttg aagagtatct ttcccgcgcg  12060
aggcataaag ttgcgtgtga tgcggaaggg tcccggcacc tcggaacggt tgttaattac  12120
ctgggcggcg agcacgatct cgtcaaagcc gttgatgttg tggcccacaa tgtaaagttc  12180
caagaagcgc gggatgccct tgatggaagg caattttta agttcctcgt aggtgagctc  12240
ttcaggggga ctgagcccgt gctctgaaag ggcccagtct gcaagatgag ggttggaagc  12300
gacgaatgag ctccacaggt cacgggccat tagcatttgc aggtggtcgc gaaaggtcct  12360
aaactggcga cctatggcca ttttttctgg ggtgatgcag tagaaggtaa gcgggtcttg  12420
ttcccagcgg tcccatccaa ggttcgcggc taggtctcgc gcggcagtca ctagaggctc  12480
atctccgccg aacttcatga ccagcatgaa gggcacgagc tgcttcccaa aggccccat  12540
ccaagtatag gtctctacat cgtaggtgac aaagagacgc tcggtgcgag gatgcgagcc  12600
gatcgggaag aactggatct cccgccacca attggaggag tggctattga tgtggtgaaa  12660
gtagaagtcc ctgcgacggg ccgaacactc gtgctggctt ttgtaaaaac gtgcgcagta  12720
ctggcagcgg tgcacgggct gtacatcctg cacgagggtg acctgacgac cgcgcacaag  12780
gaagcagagt gggaatttga gcccctcgcc tggcgggttt ggctggtggt cttctacttc  12840
ggctgcttgt ccttgaccgt ctggctgctc gagggggagtt acggtggatc ggaccaccac  12900
gccgcgcgag cccaaagtcc agatgtccgc gcgcggcggt cggagcttga tgacaacatc  12960
gcgcagatgg gagctgtcca tggtctggag ctcccgcggc gtcaggtcag gcgggagctc  13020
ctgcaggttt acctcgcata gacgggtcag ggcgcgggct agatccaggt gatacctaat  13080
ttccaggggc tggttggtgg cggcgtcgat ggcttgcaag aggccgcatc cccgcggcgc  13140
gactacggta ccgcgcggcg ggcggtgggc gcgggggtg tccttggatg atgcatctaa  13200
aagcggtgac gcgggcgagc ccccggaggt aggggggggct ccggaccccgc cgggagaggg  13260
ggcaggggca cgtcggcgcc gcgcgcgggc aggagctggt gctgcgcgcg taggttgctg  13320
gcgaacggcg cgacgcggcg gttgatctcc tgaatctggc gcctctgcgt gaagacgacg  13380
ggcccggtga gcttgagcct gaaagagagt tcgacagaat caatttcggt gtcgttgacg  13440
gcggcctggc gcaaaatctc ctgcacgtct cctgagttgt cttgataggc gatctcggcc  13500
atgaactgct cgatctcttc ctcctggaga tctccgcgtc cggctcgctc cacggtggcg  13560
gcgaggtcgt tggaaatgcg ggccatgagc tgcgagaagg cgttgaggcc tccctcgttc  13620
cagacgcggc tgtagaccac gcccccttcg gcatcgcggg cgcgcatgac cacctgcgcg  13680
```

```
agattgagct ccacgtgccg ggcgaagacg gcgtagtttc gcaggcgctg aaagagggtag  13740
ttgagggtgg tggcggtgtg ttctgccacg aagaagtaca taacccagcg tcgcaacgtg  13800
gattcgttga tatcccccaa ggcctcaagg cgctccatgg cctcgtagaa gtccacggcg  13860
aagttgaaaa actgggagtt gcgcgccgac acggttaact cctcctccag aagacggatg  13920
agctcggcga cagtgtcgcg cacctcgcgc tcaaaggcta caggggcctc ttcttcttct  13980
tcaatctcct cttccataag ggcctcccct tcttcttctt ctggcggcgg tggggaggg   14040
gggacacggc ggcgacgacg gcgcaccggg aggcggtcga caaagcgctc gatcatctcc  14100
ccgcggcgac ggcgcatggt ctcggtacgg gcgcggccgt tctcgcgggg gcgcagttgg  14160
aagacgccgc ccgtcatgtc ccggttatgg gttggcgggg ggctgccatg cggcagggat  14220
acggcgctaa cgatgcatct caacaattgt tgtgtaggta ctccgccgcc gagggacctg  14280
agcgagtccg catcgaccgg atcggaaaac ctctcgagaa aggcgtctaa ccagtcacag  14340
tcgcaaggta ggctgagcac cgtggcgggc ggcagcgggc ggcggtcggg gttgtttctg  14400
gcggaggtgc tgctgatgat gtaattaaag taggcggtct tgagacggcg gatggtcgac  14460
agaagcacca tgtccttggg tccggcctgc tgaatgcgca ggcggtcgtc ctgcccccag  14520
gcttcgtttt gacatcggcg caggtctttg tagtagtcct gcatgagcct ttctaccggc  14580
acttcttctt ctccttcctc ttgtcctgca tctcttgcat ctatcgctgc ggcggcggcg  14640
gagtttggcc gtaggtggcg ccctcttcct cccatgcgtg tgaccccgaa gcccctcatc  14700
ggctgaagca gggctaggtc ggcgacaacg cgctcggcta atatggcctg ctgcacctgc  14760
gtgagggtag actggaagtc atccatgtcc acaaagcggt ggtatgcgcc cgtgttgatg  14820
gtgtaagtgc agttggccat aacgggacag ttaacggtct ggtgaccggg ctgcgagagc  14880
tcggtgtacc tgagacgcga gtaagccctc gagtcaaata cgtagtcgtt gcaagtccgc  14940
accaggtact ggtatcccac caaaaagtgc ggcggcggat ggcggtagag ggcgcagcgt  15000
agggtggccg gggctccggg ggcgagatct tccaacataa ggcgatgata tccgtagatg  15060
tacctggaca tccaggtgat gccggcggcg gtggtggagg cgcgcggaaa gtcgcggacg  15120
cggttccaga tgttgcgcag cggcaaaaag tgctccatgg tcgggacgct ctggccggtc  15180
aggcgcgcgac aatcgttgac gctctaccgt gcaaaaggag agcctgtaag cggcgcactct  15240
tccgtggtct ggtggataaa ttcgcaaggg tatcatggcg gacgaccggg gttcgagccc  15300
cgtatccggc cgtccgccgt gatccatgcg gttaccgccc gcgtgtcgaa cccaggtgtg  15360
cgacgtcaga caacgggggga gtgctccttt tggcttcctt ccaggcgcgg cggctgctgc  15420
gctagctttt ttggccactg gccgcgcgca gcgtaagcgg ttaggctgga aagcgaaagc  15480
attaagtggc tcgctccctg tagccggagg gttattttcc aagggttgag tcgcgggacc  15540
cccggttcga gtctcggacc ggccggactg cggcgaacgg gggtttgcct ccccgtcatg  15600
caagaccccg cttgcaaatt cctccggaaa cagggacgag cccctttttt gcttttccca  15660
gatgcatccg gtgctgcggc agatgcgccc ccctcctcag cagcggcaag agcaagacga  15720
gcggcagaca tgcagggcac cctccccctcc tcctaccgcg tcaggagggg cgacatccgc  15780
ggttgacgcg gcagcagatg gtgattacga accccgcggg cgccgggccc ggcactacct  15840
ggacttggag gagggcgagg gcctggcgcg gctaggagcg ccctctcctg agcggtaccc  15900
aagggtgcag ctgaagcgtg atacgcgtga ggcgtacgtg ccgcggcaga acctgtttcg  15960
cgaccgcgag ggagaggagc ccgaggagat gcgggatcga aagttccacg cagggcgcga  16020
gctgcggcat ggcctgaatc gcgagcggtt gctgcgcgag gaggactttg agcccgacgc  16080
gcgaaccggg attagtcccg cgcgcgcaca cgtggcgggcc gccgacctgg taaccgcata  16140
cgagcagacg gtgaaccagg agattaactt tcaaaaaagc tttaacaacc acgtgcgtac  16200
gcttgtggcg cgcgaggagg tggctatagg actgatgcat ctgtgggact ttgtaagcgc  16260
gctggagcaa aacccaaata gcaagccgct catggcgcag ctgttcctta tagtgcagca  16320
cagcagggac aacgaggcat tcagggatgc gctgctaaac atagtagagc ccgagggccg  16380
ctggctgctc gatttgataa acatcctgca gagcatagtg tgtgcaggagc gcagcttgag  16440
cctggctgac aaggtggccg ccatcaacta ttccatgctt agcctgggca agtttttacgc  16500
ccgcaagata taccataccc cttacgttcc catagacaag gaggtaaaga tcgaggggtt  16560
ctacatcgc atggcgctga aggtgcttac cttgagcgac gacctgggcg tttatcgcaa  16620
cgagcgcatc cacaaggccg tgagcgtgag ccggcggcgc gagctcagcg accgcgagct  16680
gatgcacgac ctgcaaaggg ccctggctgg cacgggcgac ggcgatagag aggccgagtc  16740
ctactttgac gcgggcgctg acctgcgctg ggccccaagc cgacgcgccc tggaggcagc  16800
tggggccgga cctgggctgg cggtggcacc cgcgcgcgct ggcaacgtcg gcggcgtgga  16860
ggaatatgac gaggacgatg agtacgagcc agaggacggc gagtactaag cggtgatgtt  16920
tctgatcaga tgatgcaaga cgcaacggac ccggcggtgc gggaggccgt gcagagccag  16980
ccgtccggcc ttaactccac ggacgactgg cgccaggtca tggaccgcat catgtcgctg  17040
actgcgcgca atcctgacgc gttccggcag cagccgcagg ccaaccggct ctccgcaatt  17100
ctggaagcgg tggtcccggc gcgcgcaaac cccacgcacg agaaggtgct ggcgatcgta  17160
aacgcgctgg ccgaaaacag ggccatccgg cccgacgagg ccggcctggt ctacgacggt  17220
ctgcttcagc gcgtggctcg ttacaacagc ggcaacgtgc agaccaacct ggaccggctg  17280
gtgggggatg tgcgcgaggc cgtggcgcag cgtgagcgcg cgcagcagca gggcaacctg  17340
ggctccatgg ttgcactaaa cgccttcctg agtacacagc ccgccaacgt gccgcggga   17400
caggaggact acaccaactt tgtgagcgca ctgcggctaa tggtgactga gacaccgcaa  17460
agtgaggtgt accagtctgg gccagactat tttttccaga ccagtagaca aggcctgcag  17520
accgtaaacc tgagccaggc tttcaaaaac ttgcaggggc tgtggggggt gcgggctccc  17580
acaggcgacc gcgcgaccgt gtctagcttg ctgacgccca actcgcgcct gttgctgctg  17640
ctaatagcgc ccttcacgga cagtggcagc gtgtcccggg acacatacct aggtcacttg  17700
ctgacactgt accgcgaggc cataggtcag gcgcatgtgg acgagcatac tttccaggag  17760
attacaagtg tcagccgcgc gctggggcag gaggacacgc gcagcctgga ggcaaccctta  17820
aactacctgc tgaccaaccg gcggcagaag atccccctcgt tgcacagttt aaacagcgag  17880
gaggagcgca ttttgcgcta cgtgcagcag agcgtgagcc ttaacctgat gcgcgacggg  17940
gtaacgccca gcgtggcgct ggacatgacc gcgcgcaaca tggaaccggg catgtatgcc  18000
tcaaaccggc cgtttatcaa ccgcctaatg gactacttgc atcgcgcggc cgccgtgaac  18060
cccgagtatt tcaccaatgc catcttgaac ccgcactgcc taccccccc tggtttctac  18120
accggggggat tcgaggtgcc cgagggtaac gatggattcc tctgggacga catagacgac  18180
agcgtgtttt ccccgcaacc gcagaccctg ctagagttgc aacagcgcga gcaggacgag  18240
gcggcgctgc gaaaggaaag cttccgcagg ccaagcagct tgtccgatct aggcgctgcg  18300
gccccgcggt cagatgctag tagccccattt ccaagcttga tagggtctct taccagcact  18360
cgcaccaccc gcccgcgcct gctgggcgag gaggagtacc taaacaactc gctgctgcag  18420
```

-continued

```
ccgcagcgcg aaaaaaacct gcctccggca tttcccaaca acgggatada gagcctagtg    18480
gacaagatga gtagatggaa gacgtacgcg caggagcaca gggacgtgcc aggcccgcgc    18540
ccgcccaccc gtcgtcaaag gcacgaccgt cagcggggtc tggtgtggga ggacgatgac    18600
tcggcagacg acagcagcgt cctggatttg ggagggagtg gcaacccgtt tgcgcacctt    18660
cgccccaggc tggggagaat gttttaaaaa aaaaaaagca tgatgcaaaa taaaaaactc    18720
accaaggcca tggcaccgag cgttggtttt cttgtattcc ccttagtatg cggcgcgcgg    18780
cgatgtatga ggaaggtcct cctccctcct acgagagtgt ggtgagcgcg gcgccagtgg    18840
cggcggcgct gggttctccc ttcgatgctc ccctggaccc gccgtttgtg cctccgcggt    18900
acctgcggcc taccgggggg agaaacagca tccgttactc tgagttggca cccctattcg    18960
acaccacccg tgtgtacctg gtggacaaca agtcaacgga tgtggcatcc ctgaactacc    19020
agaacgacca cagcaacttt ctgaccacgg tcattcaaaa caatgactac agcccggggg    19080
aggcaagcac acagaccatc aatcttgacg accggtcgca ctgggcggc gacctgaaaa     19140
ccatcctgca taccaacatg ccaaatgtga acgagttcat gtttaccaat aagtttaagg    19200
cgcgggtgat ggtgtcgcgc ttgcctacta aggacaatca ggtggagctg aaatacgagt    19260
gggtggagtt cacgctgccc gagggcaact actccgagac catgaccata gaccttatga    19320
acaacgcgat cgtggagcac tacttgaaag tgggcagaca gaacgggggtt ctggaaagcg    19380
acatcggggt aaagtttgac acccgcaact tcagactggg gtttgacccc gtcactggtc    19440
ttgtcatgcc tggggtatat acaaacgaag ccttccatcc agacatcatt ttgctgccag    19500
gatgcgcggggt ggacttcacc cacagccgcc tgagcaactt gttggtgcatc cgcaagcggc  19560
aacccttcca ggagggctttt aggatcacct acgatgatct ggagggtggt aacattcccg    19620
cactgttgga tgtggacgcc taccaggcga gcttgaaaga tgacaccgaa cagggcgggg    19680
gtggcgcagg cggcagcaac agcagtggca gcggcgcgga agagaactcc aacgcggcag    19740
ccgcggcaat gcagccggtg gaggacatga acgatcatgc cattcgcggc gacaccttttg    19800
ccacacgggc tgaggagaag cgcgctgagg ccgaagcagc ggccgaagct gccgcccccg    19860
ctgcgcaacc cgaggtcgag aagcctcaga agaaaccggt gatcaaaccc ctgacagagg    19920
acagcaagaa acgcagttac aacctaataa gcaatgacag caccttcacc cagtaccgca    19980
gctggtacct tgcatacaac tacgcgacc ctcagaccgg aatccgctca tggaccctgc     20040
tttgcactcc tgacgtaacc tgcggctcgg agcaggtcta ctggtcgttg ccagacatga    20100
tgcaagaccc cgtgaccttc cgctccacgc gccagatcag caactttccg gtggtgggcg    20160
ccgagctgtt gcccgtgcac tccaagagct tctacaacg ccaggccgtc tactcccaac     20220
tcatccgcca gtttacctct ctgacccacg tgttcaatcg cttttcccgag aaccagattt    20280
tggcgcgccc gccagcccccc accatcacca ccgtcagtga aaacgttcct gctctcacag    20340
atcacgggac gctaccgctg cgcaacagca tcggaggagt ccagcgagtg accattactg    20400
acgccagacg ccgcacctgc ccctacgttt acaaggccgt gggcatagtc tcgccgcggg    20460
tcctatcgag ccgcactttt tgagcaagca tgtccatcct tatatcgccc agcaataaca    20520
caggctgggg cctgcgcttc ccaagcaaga tgtttggcgg ggccaagaag cgctccgacc    20580
aacacccagt gcgcgtgcgc gggcactacc gcgcgccctg gggcgcgcac aaacgcggcc    20640
gcactgggcg caccaccgtc gatgacgcca tcgacgcggt ggtggaggag gcgcgcaact    20700
acacgcccac gccgccacca gtgtccacag tggacgcggc cattcagacc gtggtgcgcg    20760
gagcccggcg ctatgctaaa atgaagagac ggcggaggcg cgtagcacgt cgccaccgcc    20820
gccgacccgg cactgccgcc caacgcgcgg cggcggccct gcttaaccgc gcacgtcgca    20880
ccggccgacg ggcggccatg cgggccgctc gaaggctggc cgcgggtatt gtcactgtgc    20940
ccccaggtc caggcgacga gcggccgccg cagcagccgc ggccattagt gctatgactc     21000
agggtcgcag gggcaacgtg tattgggtgc gcgactcggt tagcggcctg cgcgtgcccg    21060
tgcgcacccg ccccccgcgc aactagattg caagaaaaaa ctacttagac tcgtactgtt    21120
gtatgtatcc agcggcggcg gcgcgcaacg aagctatgtc caagcgcaaa atcaaagaag    21180
agatgctcca ggtcatcgcg ccggagatct atggcccccc gaagaaggaa gagcaggatt    21240
acaagccccg aaagctaaag cgggtcaaaa agaaaaagaa agatgatgat gatgaacttg    21300
acgacgaggt ggaactgctg cacgctaccg cgcccaggcg acgggtacag tggaaaggtc    21360
gacgcgtaaa acgtgttttg cgaccccggca ccaccgtagt ctttacgccc ggtgagcgct    21420
ccacccgcac ctacaagcgc gtgtatgatg aggtgtacgg cgaggacctg cttttgagc    21480
aggccaacga gcgcctcggg gagtttgcct acggaaagcg gcataaggac atgctggcgt    21540
tgccgctgga cgagggcaac ccaacaccta gcctaaagcc cgtaacactg cagcaggtgc    21600
tgcccgcgct tgcaccgtcc gaagaaaagc gcggcctaaa gcgcgagtct ggtgacttgg    21660
cacccaccgt gcagctgatg gtacccaagc gccagcgact ggaagatgtc ttggaaaaaa    21720
tgaccgtgga acctgggctg gagcccgagg tccgcgtgcg gccaatcaag caggtggcgc    21780
cgggactggg cgtgcagacc gtggacgttc agatacccac taccagtagc accagtattg    21840
ccaccgccac agagggcatg gagacacaaa cgtccccgt tgcctcagcg gtggcggatg     21900
ccgcggtgca ggcggtcgct gcggccgcgt ccaagacctc tacggaggtg caaacggacc    21960
cgtggatgtt tcgcgtttca gcccccccggc gcccgcgcgg ttcgaggaag tacggcgccg    22020
ccagcgcgct actgcccgaa tatgccctac atccttccat tgcgcctacc cccggctatc    22080
gtggctacac ctaccgcccc agaagacgag caactacccg acgccgaacc accactggaa    22140
cccgccgccg ccgtcgccgt cgccagcccg tgctggcccc gatttccgtg cgcagggtgg    22200
ctcgcgaagg aggcaggacc ctggtgctgc caacagcgcg ctacaccccc agcatcgttt    22260
aaaagccggt ctttgtggtt cttgcagata tggccctcac ctgccgcctc cgtttcccgg    22320
tgccgggatt ccgaggaaga atgcaccgta ggaggggcat ggccggccac ggcctgacgg    22380
gcggcatgcg tcgtgcgcac caccggcggc ggcgcgcgtc gcaccgtcgc atgcgcggcg    22440
gtatcctgcc cctccttatt ccactgatcg ccgcggcgat tggcgccgtg cccggaattg    22500
catccgtcgtgc cttgcaggcg cagagacact gattaaaaac aagttgcatg tggaaaaatc    22560
aaaataaaaa gtctggactc tcacgctcgc ttggtcctgt aactattttg tagaatggaa    22620
gacatcaact ttgcgtctct ggccccgcga cacggctcgc gcccgttcat gggaaactgg    22680
caagatatcg gcaccagcaa tatgagcggt ggcgccttca gctggggctc gctgtggagc    22740
ggcattaaaa atttcggttc caccgttaag aactatggca gcaaggcctg gaacagcagc    22800
acaggccaga tgctgagggga taagttgaaa gagcaaaatt tccaacaaaa ggtgtagat     22860
ggcctggcct ctggcattag cggggtggtg gacctggcca accaggcagt gcaaaataag    22920
attaacagta agcttgatcc ccgccctccc gtagaggagc ctccaccggc cgtggagaca    22980
gtgtctccag aggggcgtgg cgaaaagcgt ccgcgccccg acaggaaga aactctggtc      23040
acgcaaatag acgagcctcc ctcgtacgag gaggcactaa agcaaggcct gcccaccacc    23100
cgtcccatcg cgcccatggc taccggagtg ctgggccagc acacaccccgt aacgctggac    23160
```

-continued

```
ctgcctcccc ccgccgacac ccagcagaaa cctgtgctgc caggccccgac cgccgttgtt   23220
gtaaccggtc ctagccgcgc gtccctgcgc cgcgccgcca gcggtccgcg atcgttgcgg   23280
cccgtagcca gtggcaactg gcaaagcaca ctgaacagca tcgtgggtct gggggtgcaa   23340
tccctgaagc gccgacgatg cttctgaata gctaacgtgt cgtatgtgtg tcatgtatgc   23400
gtccatgtcg ccgccagagg agctgctgag ccgccgcgcg cccgctttcc aagatggcta   23460
cccctttcgat gatgccgcag tggtcttaca tgcacatctc gggccaggac gcctcggagt   23520
acctgagccc cgggctggtg cagtttgccc gcgccaccga gacgtacttc agcctgaata   23580
acaagtttag aaaccccacg gtggcgccta cgcacgacgt gaccacagac cggtcccagc   23640
gtttgacgct gcggttcatc cctgtggacc gtgaggatac tgcgtactcg tacaaggcga   23700
ggttcacccct agctgtgggt gataaccgtg tgctggacat ggcttccacg tactttgaca   23760
tccgcggcgt gctggacagg ggccctactt ttaagcccta ctctggcact gcctacaacg   23820
ccctggctcc caagggtgcc ccaaatcctt gcgaatggga tgaagctgct actgctcttg   23880
aaataaacct agaagaagag gacgatgaca acgaagacga agtagacgag caagctgagc   23940
agcaaaaaac tcacgtattt gggcaggcgc cttattctgg tataaatatt acaaaggagg   24000
gtattcaaat aggtgtcgaa ggtcaaacac ctaaatatgc cgataaaaca tttcaacctg   24060
aacctcaaat aggagaatct cagtggtacg aaactgaaat taatcatgca gctgggagag   24120
tccttaaaaa gactaccccca atgaaaccat gttacggttc atatgcaaaa cccacaaatg   24180
aaaatggagg gcaaggcatt cttgtaaagc aacaaaatgg aaagctagaa agtcaagtcg   24240
aaatgcaatt tttctcaact actgaggcga ccgcaggcaa tggtgataac ttgactccta   24300
aagtggtatt gtacagtgaa gatgtagata tagaaacccc agacactcat atttcttaca   24360
tgcccactat taaggaaggt aactcacgag aactaatggg ccaacaatct atgcccaaca   24420
ggcctaatta cattgctttt agggacaatt ttattggtct aatgtattac aacagcacgg   24480
gtaatatggg tgttctggcg ggccaagcat cgcagttgaa tgctgttgta gatttgcaag   24540
acagaaacac agagctttca taccagcttt tgcttgattc cattggtgat agaaccaggt   24600
actttttctat gtggaatcag gctgttgaca gctatgatcc agatgttaga attattgaaa   24660
atcatggaac tgaagatgaa cttccaaatt actgctttcc actgggaggt gtgattaata   24720
cagagactct taccaaggta aaacctaaaa caggtcagga aaatggatgg gaaaaagatg   24780
ctacagaatt ttcagataaa aatgaaataa gagttggaaa taattttgcc atggaaatca   24840
atctaaatgc caacctgtgg agaaatttcc tgtactccaa catagcgctg tatttgcccg   24900
acaagctaaa gtacagtcct tccaacgtaa aaatttctga taacccaaac acctacgact   24960
acatgaacaa gcgagtggtg gctcccgggt tagtggactg ctacattaac cttgggagcac   25020
gctggtccct tgactatatg gacaacgtca acccatttaa ccaccaccgc aatgctggcc   25080
tgcgctaccg ctcaatgttg ctgggcaatg gtcgctatgt gcccttccac atccaggtgc   25140
ctcagaagtt ctttgccatt aaaaacctcc ttctcctgcc gggctcatac acctacgagt   25200
ggaacttcag gaaggatgtt aacatggttc tgcagagctc cctaggaaat gacctaaggg   25260
ttgacggagc cagcattaag tttgatagca tttgcctttta cgccaccttc ttccccatgg   25320
cccacaacac cgcctccacg cttgaggcca tgcttagaaa cgacaccaac gaccagtcct   25380
ttaacgacta tctctccgcc gccaacatgc tctaccctat acccgccaac gctaccaacg   25440
tgcccatatc catcccctcc cgcaactggg cggctttccg cggctgggcc ttcacgcgcc   25500
ttaagactaa ggaaaccca tcactgggct cgggctacga cccttattac aacctactctg   25560
gctctatacc ctacctagat ggaaccttt acctcaacca caccttaag aaggtggcca   25620
ttacctttga ctcttctgtc agctggcctg gcaatgaccg cctgcttacc cccaacgagt   25680
ttgaaattaa gcgctcagtt gacggggagg gttacaacgt tgcccagtgt aacatgacca   25740
aagactggtt cctggtacaa atgctagcta actacaacat tggctaccag ggcttctata   25800
tcccagagag ctacaaggac cgcatgtact ccttctttag aaacttccag cccatgagcc   25860
gtcaggtggt ggatgatact aaatacaagg actaccaaca ggtgggcatc ctacaccaac   25920
acaacaactc tggatttgtt ggctaccttg ccccaccat gcgcgaagga caggcctacc   25980
ctgctaactt cccctatccg cttataggca gaccgcagt tgacagcatt cccagaaaa   26040
agttttctttg cgatcgcacc cttttggcgca tcccattctc cagtaacttt atgtccatgg   26100
gcgcactcac agacctgggc caaaaccttc tctacgccaa ctccgcccac gcgctagaca   26160
tgacttttga ggtggatccc atggacgagc ccaccccttc ttatgtttttg tttgaagtct   26220
ttgacgtggt ccgtgtgcac cggccgcacc gcggcgtcat cgaaaccgtg tacctgcgca   26280
cgcccttctc ggccggcaac gccacaacat aaagaagcaa gcaacatcaa caacagctgc   26340
cgccatgggc tccagtgagc aggaactgaa agccattgtc aaagatcttg gttgtgggcc   26400
atatttttttg ggcacctatg acaagcgctt tccaggcttt gtttctccac acaagctcgc   26460
ctgcgccata gtcaatacgg ccggtcgcga gactgggggc gtacactgga tggcctttgc   26520
ctggaacccg cactcaaaaa catgctacct ctttgagccc tttggctttt ctgaccagcg   26580
actcaagcag gtttaccagt ttgagtacga gtcactcctg cgccgtagcg ccattgcttc   26640
ttcccccgac cgctgtataa cgctggaaaa gtccacccaa agcgtacagg ggccccaactc   26700
ggccgcctgt ggactattct gctgcatgtt tctccacgcc tttgccaact ggccccaaac   26760
tcccatggat cacaacccca ccatgaacct tattaccggg gtacccaact ccatgctcaa   26820
cagtccccag gtacagccca ccctgcgtcg caaccaggaa cagctctaca gcttcctgga   26880
gcgccactcg ccctacttcc gcagccacag tgcgcagatt aggagcgcca cttcttttttg   26940
tcacttgaaa aacatgtaaa aataatgtac tagagacact tcaataaagg caaatgcttt   27000
ttatttgtac actctcgggt gattatttac ccccaccctt gccgtctgcg ccgtttaaaa   27060
atcaaagggg ttctgccgcg catcgctatg cgccactggc agggacacgt tgcgatactg   27120
gtgtttagtc ctcacttaaa ctcaggcac aaccatccgc ggcagctcgg tgaagttttc   27180
actccacagg ctgcgcacca tcaccaacgc gtttagcagg tcgggcgccg atatcttgaa   27240
gtcgcagttg gggcctccgc cctgcgcgcg cgagttgcga tacacagggt tgcagcactg   27300
gaacactatc agcgccgggt ggtgcacgct ggccagcacg ctcttgtcgg agatcagatc   27360
cgcgtccagg tcctccgcgt tgctcagggc gaacggagtc aactttggta gctgccttcc   27420
caaaaagggc gcgtgcccag gctttgagtt gcactcgcac cgtagtggca tcaaaaggtg   27480
accgtgcccg gtctgggcgt taggatacag cgcctgcata aaagccttga tctgcttaaa   27540
agccacctga gcctttgcgc cttcagagaa gaacatgccg caagacttgc cggaaaactg   27600
attggccgga caggccgcgt cgtgcacgca gcaccttgcg tcggtgttgg agatctgcac   27660
cacatttcgg ccccaccggt tcttcacgat cttggccttg ctagactgct ccttcagcgc   27720
gcgctgcccg ttttcgctcg tcacatccat ttcaatcacg tgctcttat ttatcataat   27780
gcttccgtgt agacacttaa gctcgccttc gatctcagcg cagcggtgca gccacaacgc   27840
gcagcccgtg ggctcgtgat gcttgtaggt cacctctgca aacgactgca ggtacgcctg   27900
```

-continued

```
caggaatcgc cccatcatcg tcacaaaggt cttgttgctg gtgaaggtca gctgcaaccc   27960
gcggtgctcc tcgttcagcc aggtcttgca tacggccgcc agagcttcca cttggtcagg   28020
cagtagtttg aagttcgcct ttagatcgtt atccacgtgg tacttgtcca tcagcgcgcg   28080
cgcagcctcc atgcccttct cccacgcaga cacgatcggc acactcagcg ggttcatcac   28140
cgtaatttca ctttccgctt cgctgggctc ttcctcttcc tcttgcgtcc gcataccacg   28200
cgccactggg tcgtcttcat tcagccgccg cactgtgcgc ttacctcctt tgccatgctt   28260
gattagcacc ggtgggttgc tgaaacccac catttgtagc gccacatctt ctctttcttc   28320
ctcgctgtcc acgattacct ctggtgatgg cgggcgctcg ggcttgggag aagggcgctt   28380
ctttttcttc ttgggcgcaa tggccaaatc cgccgccgag gtcgatggcc gcgggctggg   28440
tgtgcgcggc accagcgcgt cttgtgatga gtcttcctcg tcctcggact cgatacgccg   28500
cctcatccgc tttttggggg gcgcccgggg aggcggcggc gacggggacg gggacgacac   28560
gtcctccatg gttgggggac gtcgcgccgc accgcgtccg cgctcggggg tggtttcgcg   28620
ctgctcctct tcccgactgg ccatttcctt ctcctatagg cagaaaaaga tcatggagtc   28680
agtcgagaag aaggacagcc taaccgcccc ctctgagttc gccaccaccg cctccaccga   28740
tgccgccaac gcgcctacca ccttccccgt cgaggcaccc ccgcttgagg aggaggaagt   28800
gattatcgag caggacccag gttttgtaag cgaagacgac gaggaccgct cagtaccaac   28860
agaggataaa aagcaagacc aggacaacgc agaggcaaac gaggaacaag tcgggcgggg   28920
ggacgaaagg catggcgact acctagatgt gggagacgac gtgctgttga agcatctgca   28980
gcgccagtgc gccattatct gcgacgcgtt gcaagagcgc agcgatgtgc ccctcgccat   29040
agcggatgtc agccttgcct acgaacgcca cctattctca ccgcgcgtac cccccaaacg   29100
ccaagaaaac ggcacatgcg agcccaaccc gcgcctcaac ttctaccccg tatttgccgt   29160
gccagaggtg cttgccacct atcacatctt tttccaaaac tgcaagatac ccctatcctg   29220
ccgtgccaac cgcagccgag cggacaagca gctggccttg cggcagggcg ctgtcatacc   29280
tgatatcgcc tcgctcaacg aagtgccaaa aatctttgag ggtcttggac gcgacgagaa   29340
gcgcgcggca aacgctctgc aacaggaaaa cagcgaaaat gaaagtcact ctggagtgtt   29400
ggtggaactc gagggtgaca acgcgcgcct agccgtacta aaacgcagca tcgaggtcac   29460
ccactttgcc tacccggcac ttaacctacc ccccaaggtc atgagcacag tcatgagtga   29520
gctgatcgtg cgccgtgcgc agcccctgga gagggatgca aatttgcaag aacaaacaga   29580
ggagggccta cccgcagttg gcgacgagca gctagcgcgc tggcttcaaa cgcgcgagcc   29640
tgccgacttg gaggagcgac gcaaactaat gatggcccga gtgctcgtta ccgtggagct   29700
tgagtgcatg cagcggttct ttgctgaccc ggagatgcag cgcaagctag aggaaacatt   29760
gcactacacc tttcgacagg gctacgtacg ccaggcctgc aagatctcca acgtggagct   29820
ctgcaacctg gtctcctacc ttggaatttt gcacgaaaac cgccttgggc aaaacgtgct   29880
tcattccacg ctcaagggcg aggcgcgccg cgactacgtc cgcgactgcg tttacttatt   29940
tctatgctac acctggcaga cggccatggg cgtttggcag cagtgcttgg aggagtgcaa   30000
cctcaaggag ctgcagaaac tgctaaagca aaacttgaag gacctatgga cggccttcaa   30060
cgagcgctcc gtggccgcgc acctggcgga catcatttc cccgaacgcc tgcttaaaac   30120
cctgcaacag ggtctgccag acttcaccag tcaaagcatg ttgcagaact ttaggaactt   30180
tatcctagag cgctcaggaa tcttgcccgc cacctgctgt gcacttccta gcgactttgt   30240
gcccattaag taccgcgaat gccctccgcc gctttgggg cactgctacc ttctgcagct   30300
agccaactac cttgcctacc actctgacat aatggaagac gtgagcggtg acggtctact   30360
ggagtgtcac tgtcgctgca acctatgcac cccgcaccgc tccctggttt gcaattcgca   30420
gctgcttaac gaaagtcaaa ttatcggtac ctttgagctg cagggtcct cgcctgacga   30480
aaagtccgcg gctccggggt tgaaactcac tccggggctg tggacgtcgg cttaccttcg   30540
caaatttgta cctgaggact accacgccca cgagattagg ttctacgaag accaatcccg   30600
cccgccaaat gcggagctta ccgcctgcgt cattacccag ggccacattc ttggccaatt   30660
gcaagccatc aacaaagccc gccaagagtt tctgctacga aagggacggg gggtttactt   30720
ggaccccccag tccggcgagg agctcaaccc aatccccccg ccgccgcagc cctatcagca   30780
gcagccgcgg gcccttgctt cccaggatgg cacccaaaaa gaagctgcag ctgccgccgc   30840
cacccacgga cgaggaggaa tactgggaca gtcaggcaga ggaggttttg dacgaggagg   30900
aggaggacat gatggaagac tgggagagcc tagacgaagg agcttccgag gtcgaagagg   30960
tgtcagacga aacaccgtca ccctcggtcg cattcccctc gccggcgccc cagaaatcgg   31020
caaccggttc cagcatggct acaacctccg ctcctcaggc gccgccggca ctgcccgttc   31080
gccgacccaa ccgtagatgg dacaccactg gaaccagggc cggtaagtcc aagcagccgc   31140
cgccgttagc ccaagagcaa caacagcgcc aaggctaccg ctcatggcgc gggcacaaga   31200
acgccatagt tgcttgcttg caagactgtg ggggcaacat ctccttcgcc cgccgctttc   31260
ttctctacca tcacgcgtg gccttcccc gtaacatcct gcattactac cgtcatctct   31320
acagcccata ctgcaccggc ggcagcggca gcggcagcaa cagcagcggc cacacagaag   31380
caaaggcgac cggatagcaa gactctgaca aagcccaaga aatccacagc ggcggcagca   31440
gcaggaggag gagcgctgcg tctggcgccc aacgaacccg tatcgacccg cgagcttaga   31500
aacaggattt ttcccactct gtatgctata tttcaacaga gcaggggcca agaacaagag   31560
ctgaaaataa aaaacaggtc tctgcgatcc ctcacccgca gctgcctgta tcacaaaagc   31620
gaagatcagc ttcggcgcac gctggaagac gcggaggctc tcttcagtaa atactgcgcg   31680
ctgactctta aggactagtt tcgcgccctt tctcaaattt aagcgcgaaa actacgtcat   31740
ctccagcggc cacacccggc gccagcacct gtcgtcagcg ccattatgag caaggaaatt   31800
cccacgccct acatgtggag ttaccagcca caaatgggac ttgcggctgg agctgcccaa   31860
gactactcaa cccgaataaa ctacatgagc gcggaccccc acatgatatc ccgggtcaac   31920
ggaatccgcg cccaccgaaa ccgaattctc ttggaacagg cggctattac caccacacct   31980
cgtaataacc ttaatccccg tagttggccc gctgccctgg tgtaccagga aagtcccgct   32040
cccaccactg tggtacttcc cagagacgcc caggccgaag ttcagatgac taactcaggg   32100
gcgcagcttg cgggcggctt tcgtcacagg gtgcggtcgc ccgggcaggg tataactcac   32160
ctgacaatca gagggcgagg tattcagctc aacgacgagt cggtgagctc ctcgcttggt   32220
ctccgtccgg acgggacatt tcagatcggc ggcgccggcc gtccttcatt cacgcctcgt   32280
caggcaatca taactctgca gacctcgtcc tctgagccgc gctctggagg cattggaact   32340
ctgcaattta ttgaggagtt tgtgccatcg gtctacttta acccccttctc gggacctccc   32400
ggccactatc cggatcaatt tattcctaac tttgacgcgg taaaggactc ggcggacggc   32460
tacgactgaa tgttaagtgg agaggcagag caactgcgcc tgaaacacct ggtccactgt   32520
cgccgccaca agtgctttgc ccgcgactcc ggtgagtttt gctactttga attgcccgag   32580
gatcatatcg agggcccggc gcacggcgtc cggcttaccg cccaggggaga gcttgcccgt   32640
```

-continued

```
agcctgattc gggagtttac ccagcgcccc ctgctagttg agcgggacag gggaccctgt    32700
gttctcactg tgatttgcaa ctgtcctaac cttggattac atcaagatcc tctagttata    32760
actagagtac ccggggatct tattcccttt aactaataaa aaaaaataat aaagcatcac    32820
ttacttaaaa tcagttagca aatttctgtc cagtttattc agcagcacct ccttgccctc    32880
ctcccagctc tggtattgca gcttcctcct ggctgcaaac tttctccaca atctaaatgg    32940
aatgtcagtt tcctcctgtt cctgtccatc cgcacccact atcttcatgt tgttgcagat    33000
gaagcgcgca agaccgtctg aagatacctt caaccccgtg tatccatatg acacggaaac    33060
cggtcctcca actgtgcctt ttcttactcc tccctttgta tcccccaatg ggtttcaaga    33120
gagtccccct ggggtactct ctttgcgcct atccgaacct ctagttacct ccaatggcat    33180
gcttgcgctc aaaatgggca acggcctctc tctggacgag gccggcaacc ttacctccca    33240
aaatgtaacc actgtgagcc cacctctcaa aaaaaccaag tcaaacataa acctggaaat    33300
atctgcaccc ctcacagtta cctcagaagc cctaactgtg gctgccgccg cacctctaat    33360
ggtcgcgggc aacacactca ccatgcaatc acaggccccg ctaaccgtgc acgactccaa    33420
acttagcatt gccacccaag gacccctcac agtgtcagaa ggaaagctag ccctgcaaac    33480
atcaggcccc ctcaccacca ccgatagcag taccccttact atcactgcct caccccctct    33540
aactactgcc actggtagct tgggcattga cttgaaagag cccatttata cacaaaatgg    33600
aaaactagga ctaaagtacg gggctccttt gcatgtaaca gacgacctaa acactttgac    33660
cgtagcaact ggtccaggtg tgactattaa taatacttcc ttgcaaacta aagttactgg    33720
agccttgggt tttgattcac aaggcaatat gcaacttaat gtagcaggag gactaaggat    33780
tgattctcaa aacagacgcc ttatacttga tgttagttat ccgtttgatg ctcaaaacca    33840
actaaatcta agactaggac agggccctct tttttataaac tcagcccaca acttggatat    33900
taactacaac aaaggccttt acttgtttac agcttcaaac aattccaaaa agcttgaggt    33960
taacctaagc actgccaagg ggttgatgtt tgacgctaca gccatagcca ttaatgcagg    34020
agatgggctt gaatttggtt cacctaatgc accaaacaca aatcccctca aaacaaaaat    34080
tggccatggc ctagaatttg attcaaacaa ggctatggtt cctaaactag gaactggcct    34140
tagttttgac agcacaggtg ccattacagt aggaaacaaa aataatgata agctaacttt    34200
gtggaccaca ccagctccat tcctaactg tagactaaat gcagagaaag atgctaaact    34260
cactttggtc ttaacaaaat gtggcagtca aatacttgct acagtttcag tttttggctgt    34320
taaaggcagt ttggctccaa tatctggaac agttcaaagt gctcatctta ttataagatt    34380
tgacgaaaat ggagtgctac taaacaattc cttcctggac ccagaatatt ggaactttag    34440
aaatggagat cttactgaag gcacagccta tacaaacgct gttggattta tgcctaacct    34500
atcagcttat ccaaaatctc acggtaaaac tgccaaaagt aacattgtca gtcaagttta    34560
cttaaacgga gacaaaacta aacctgtaac actaaccatt acactaaacg gtacacagga    34620
aacaggagac acaactccaa gtgcatactc tatgtcattt tcatgggact ggtctggcca    34680
caactacatt aatgaaatat ttgccacatc ctcttacact ttttcataca ttgcccaaga    34740
ataaagaatc gtttgtgtta tgtttcaacg tgtttatttt tcaattgcag aaaatttcaa    34800
gtcatttttc attcagtagt atagccccac caccacatag cttatacaga tcaccgtacc    34860
ttaatcaaac tcacagaacc ctagtattca acctgccacc tccctcccaa cacacagagt    34920
acacagtcct ttctcccgg ctggccttaa aaagcatcat atcatgggta acagacatat    34980
tcttaggtgt tatattccac acggtttcct gtcgagccaa acgctcatca gtgatattaa    35040
taaactcccc gggcagctca cttaagttca tgtcgctgtc cagctgctga gccacaggct    35100
gctgtccaac ttgcggttgc ttaacgggcg gcgaaggaga agtccacgcc tacatggggg    35160
tagagtcata atcgtgcatc aggatagggc ggtggtgctg cagcagcgcg cgaataaact    35220
gctgccgccg ccgctccgtc ctgcaggaat acaacatggc agtggtctcc tcagcgatga    35280
ttcgcaccgc ccgcagcata aggcgccttg tcctccgggc acagcagcgc accctgatct    35340
cacttaaatc agcacagtaa ctgcagcaca gcaccacaat attgttcaaa atcccacagt    35400
gcaaggcgct gtatccaaag ctcatggcgg ggaccacaga acccacgtgg ccatcatacc    35460
acaagcgcag gtagattaag tggcgacccc tcataaacac gctggacata aacattacct    35520
cttttggcat gttgtaattc accacctccc ggtaccatat aaacctctga ttaaacatgg    35580
cgccatccac caccatccta aaccagctgg ccaaaacctg cccgccggct atacactgca    35640
gggaaccggg actggaacaa tgacagtgga gagcccagga ctcgtaacca tggatcatca    35700
tgctcgtcat gatatcaatg ttggcacaac acaggcacac gtgcatacac ttcctcagga    35760
ttacaagctc ctcccgcgtt agaaccatat cccaggggaac aacccattcc tgaatcagcg    35820
taaatcccac actgcaggga agacctcgca cgtaactcac gttgtgcatt gtcaaagtgt    35880
tacattcggg gacgagcgga tgatcctcca gtatggtagc gcggttttct gtctcaaaag    35940
gaggtagacg atccctactg tacggagtgc gccgagacaa ccgagatcgt gttggtcgta    36000
gtgtcatgcc aaatggaacg ccggacgtag tcatatttcc tgaagcaaaa ccaggtgcgg    36060
gcgtgacaaa cagatctgcg tctccggtct cgccgcttag atcgctctgt gtagtagttg    36120
tagtatatcc actctctcaa agcatccagg cgccccctg cttcgggttc tatgtaaact    36180
ccttcatgcg ccgctgccct gataacatcc accaccgcag aataagccac acccagccaa    36240
cctacacatt cgttctgcga gtcacacacg ggaggagcgg gaaagagctgg aagaaccatg    36300
ttttttttt tattccaaaa gattatccaa aacctcaaaa tgaagatcta ttaagtgaac    36360
gcgctcccct ccggtggcgt ggtcaaactc tacagccaaa gaacagataa tggcatttgt    36420
aagatgttgc acaatggctt ccaaaaggca aacggccctc acgtccaagt ggacgtaaag    36480
gctaaaccct tcagggtgaa tctcctctat aaacattcca gcaccttcaa ccatgcccaa    36540
ataattctca tctcgccacc ttctcaatat atctctaagc aaatcccgaa tattaagtcc    36600
ggccattgta aaaatctgct ccagagcgcc ctccaccttc agcctcaagc agcgaatcat    36660
gattgcaaaa attcaggttc ctcacagacc tgtataagat tcaaaagcgg aacattaaca    36720
aaaataccgc gatcccgtag gtcccttcgc agggccagct gaacataatc gtgcaggtct    36780
gcacggacca gcgcggccac ttccccgcca ggaaccttga caaaagaacc cacactgatt    36840
atgcacgca tactcggagc tatgctaacc agcgtagccc cgatgtaagc tttgttgcat    36900
gggcggcgat ataaaatgca aggtgctgct caaaaaatca ggcaaagcct cgcgcaaaaa    36960
agaaagcaca tcgtagtcat gctcatgcag ataaaggcag gtaagctccg gaaccaccac    37020
agaaaaagac accattttc tctcaaacat gtctgcgggt ttctgcataa acacaaaata    37080
aaataacaaa aaaacattta aacattagaa gcctgtctta caacaggaaa aacaacctt    37140
ataagcataa gacggactac ggccatgccg gcgtgaccgt aaaaaaactg gtcaccgtga    37200
ttaaaaagca ccaccgacag ctcctcggtc atgtccggag tcataatgta agactcggta    37260
aacacatcag gttgattcat cggtcagtgc taaaaagcga ccgaaatagc ccgggggaat    37320
acatacccgc aggcgtagag acaacattac agcccccata ggaggtataa caaaattaat    37380
```

```
aggagagaaa aacacataaa cacctgaaaa accctcctgc ctaggcaaaa tagcaccctc   37440
ccgctccaga acaacataca gcgcttcaca gcggcagcct aacagtcagc cttaccagta   37500
aaaaagaaaa cctattaaaa aaacaccact cgacacggca ccagctcaat cagtcacagt   37560
gtaaaaaagg gccaagtgca gagcgagtat atataggact aaaaaatgac gtaacggtta   37620
aagtccacaa aaaacaccca gaaaaccgca cgcgaaccta cgcccagaaa cgaaagccaa   37680
aaaacccaca acttcctcaa atcgtcactt ccgttttccc acgttacgta acttcccatt   37740
ttaagaaaac tacaattccc aacacataca agttactccg ccctaaaacc tacgtcaccc   37800
gccccgttcc cacgcccgc gccacgtcac aaactccacc ccctcattat catattggct   37860
tcaatccaaa ataaggtata ttattgatga tnnn                             37894
```

```
SEQ ID NO: 12       moltype = DNA  length = 37892
FEATURE             Location/Qualifiers
source              1..37892
                    mol_type = other DNA
                    organism = synthetic construct
SEQUENCE: 12
nnttaattaa ggatccnnnc ctgtcctcga ccgatgccct tgagagcctt caacccagtc   60
agctccttcc ggtgggcgcg gggcatgact atcgtcgccg cacttatgac tgtcttcttt   120
atcatgcaac tcgtaggaca ggtgccggca gcgctctggg tcattttcgg cgaggaccgc   180
tttcgctgga gcgcgacgat gatcggcctg tcgcttgcgg tattcggaat cttgcacgcc   240
ctcgctcaag ccttcgtcac tggtcccgcc accaaacgtt tcggcgagaa gcaggccatt   300
atcgccggca tggcggccga cgcgctgggc tacgtcttgc tggcgttcgc gacgcgaggc   360
tggatggcct tccccattat gattcttctc gcttccggcg gcatcgggat gcccgcgttg   420
caggccatgc tgtccaggca ggtagatgac gaccatcagg gacagcttca aggatcgctc   480
gcggctctta ccagcctaac ttcgatcact ggaccgctga tcgtcacggc gatttatgcc   540
gcctcggcga gcacatggaa cgggttggca tggattgtag gcgccgccct ataccttgtc   600
tgcctccccg cgttgcgtcg cggtgcatgg agccgggcca cctcgacctg aatggaagcc   660
ggcggcacct cgctaacgga ttcaccactc caagaattgg agccaatcaa ttcttgcgga   720
gaactgtgaa tgcgcaaacc aacccttggc agaacatatc catcgcgtcc gccatctcca   780
gcagccgcac gcggcgcatc tcgggcagcg ttgggtcctg gccacgggtg cgcatgatcg   840
tgctcctgtc gttgaggacc cggctaggct ggcgggggttg ccttactggt tagcagaatg   900
aatcaccgat acgcgagcga acgtgaagcg actgctgctg caaaacgtct gcgacctgag   960
caacaacatg aatggtcttc ggtttccgtg tttcgtaaag tctggaaacg cggaagtcag   1020
cgccctgcac cattatgttc cggatctgca tcgcaggatg ctgctggcta ccctgtggaa   1080
cacctacatc tgtattaacg aagcgctggc attgaccctg agtgattttt ctctggtccc   1140
gccgcatcca taccgccagt tgtttaccct cacaacgttc cagtaaccgg gcatgttcat   1200
catcagtaac ccgtatcgtg agcatcctct ctcgtttcat cggtatcatt accccatga   1260
acagaaattc ccccttacac ggaggcatca agtgaccaaa caggaaaaaa ccgcccttaa   1320
catggccgc tttatcagaa gccagacatt aacgcttctg agaaactca acgagctgga   1380
cgcggatgaa caggcagaca tctgtgaatc gcttcacgac cacgctgatg agctttaccg   1440
cagctgcctc gcgcgtttcg gtgatgacgg tgaaaacctc tgacacatgc agctcccgga   1500
gacggtcaca gcttgtctgt aagcggatgc cgggagcaga caagcccgtc agggcgcgtc   1560
agcgggtgtt ggcgggtgtc ggggcgcagc catgacccag tcacgtagcg atagcggagt   1620
gtatactggc ttaactatgc ggcatcagag cagattgtac tgagagtgca ccatatgcgg   1680
tgtgaaatac cgcacagatg cgtaaggaga aaataccgca tcaggcgctc ttccgcttcc   1740
tcgctcactg actcgctgcg ctcggtcgtt cggctgcggc gagcggtatc agctcactca   1800
aaggcggtaa tacggttatc cacagaatca ggggataacg caggaaagaa catgtgagca   1860
aaaggccagc aaaaggccag gaaccgtaaa aaggccgcgt tgctggcgtt tttccatagg   1920
ctccgccccc ctgacgagca tcacaaaaat cgacgctcaa gtcagaggtg gcgaaacccg   1980
acaggactat aaagatacca ggcgtttccc cctggaagct ccctcgtgcg ctctcctgtt   2040
ccgaccctgc cgcttaccgg atacctgtcc gcctttctcc cttcgggaag cgtggcgctt   2100
tctcaatgct cacgctgtag gtatctcagt tcggtgtagg tcgttcgctc caagctgggc   2160
tgtgtgcacg aaccccccgt tcagcccgac cgctgcgcct tatccggtaa ctatcgtctt   2220
gagtccaacc cggtaagaca cgacttatcg ccactggcag cagccactgg taacaggatt   2280
agcagagcga ggtatgtagg cggtgctaca gagttcttga agtggtggcc taactacggc   2340
tacactagaa ggacagtatt tggtatctgc gctctgctga agccagttac cttcggaaaa   2400
agagttggta gctcttgatc cggcaaacaa accaccgctg gtagcggtgg tttttttgtt   2460
tgcaagcagc agattacgcg cagaaaaaaa ggatctcaag aagatccttt gatcttttct   2520
acggggtctg acgctcagtg gaacgaaaac tcacgttaag ggattttggt catgagatta   2580
tcaaaaagga tcttcaccta gatccttta aattaaaaat gaagttttaa atcaatctaa   2640
agtatatatg agtaaacttg gtctgacagt taccaatgct taatcagtga ggcacctatc   2700
tcagcgatct gtctatttcg ttcatccata gttgcctgac tccccgtcgt gtagataact   2760
acgatacggg agggcttacc atctggcccc agtgctgcaa tgataccgcg agacccacgc   2820
tcaccggctc cagatttatc agcaataaac cagccagccg gaagggccga cggcttgtcc   2880
ggtcctgcaa ctttatccgc ctccatccag tctattaatt gttgccggga agctagagta   2940
agtagttcgc cagttaatag tttgcgcaac gttgttgnna aaaaggatct tcacctagat   3000
cctttttcacg tagaaagcca gtccgcagaa acggtgctga ccccggatga atgtcagcta   3060
ctgggctatc tggacaaggg aaaacgcaag cgcaaagaga aagcaggtag cttgcagtgg   3120
gcttacatgg cgatagctag actgggcggt tttatggaca gcaagcgaac cggaattgcc   3180
agctggggcg ccctctggta aggttgggaa gccctgcaaa gtaaactgga tggctttctc   3240
gccgccaagg atctgatggc gcaggggatc aagctctgat caagacag gatgaggatc   3300
gtttcgcatg attgaacaag atggattgca cgcaggttct ccggccgctt gggtggagag   3360
gctattcggc tatgactggg cacaacagac aatcggctgc tctgatgccg ccgtgttccg   3420
gctgtcagcg caggggcgcc cggttctttt gtcaagaccg acctgtccg gtgccctgaa   3480
tgaactgcaa gacgaggcag cgcggctatc gtggctggcc acgacgggcg ttccttgcgc   3540
agctgtgctc gacgttgtca ctgaagcggg aagggactgg ctgctattgg gcgaagtgcc   3600
ggggcaggat ctcctgtcat ctcaccttgc tcctgccgag aaagtatcca tcatggctga   3660
tgcaatgcgg cggctgcata cgcttgatcc ggctacctgc ccattcgacc accaagcgaa   3720
acatcgcatc gagcgagcac gtactcggat ggaagccggt cttgtcgatc aggatgatct   3780
```

-continued

```
ggacgaagag catcaggggc tcgcgccagc cgaactgttc gccaggctca aggcgagcat     3840
gcccgacggc gaggatctcg tcgtgaccca tggcgatgcc tgcttgccga atatcatggt     3900
ggaaaatggc cgcttttctg gattcatcga ctgtggccgg ctgggtgtgg cggaccgcta     3960
tcaggacata gcgttggcta cccgtgatat tgctgaagag cttggcggcg aatgggctga     4020
ccgcttcctc gtgctttacg gtatcgccgc tcccgattcg cagcgcatcg ccttctatcg     4080
ccttcttgac gagttcttct gaattttgtt aaaatttttg ttaaatcagc tcatttttta     4140
accaataggc cgaaatcggc aacatccctt ataaatcaaa agaatagacc gcgatagggt     4200
tgagtgttgt tccagtttgg aacaagagtc cactattaaa gaacgtggac tccaacgtca     4260
aagggcgaaa aaccgtctat cagggcgatg gcccactacg tgaaccatca cccaaatcaa     4320
gttttttgcg gtcgaggtgc cgtaaagctc taaatcggaa ccctaaaggg agccccgat     4380
ttagagcttg acggggaaag ccggcgaacg tggcgagaaa ggaagggaag aaagcgaaag     4440
gagcgggcgc tagggcgctg gcaagtgtag cggtcacgct gcgcgtaacc accacacccg     4500
cgcgcttaat gcgccgnnnn nnttaattaa nnntcccttc cagctctctg cccctttgg     4560
attgaagcca atatgataat gagggggtgg agtttgtgac gtggcgcggg gcgtgggaac     4620
ggggcgggtg acgtagtagt gtggcggaag tgtgatgttg caagtgtggc ggaacacatg     4680
taagcgacgg atgtggcaaa agtgacgttt ttggtgtgcg ccggtgtaca caggaagtga     4740
caattttcgc gcggttttag gcggatgttg tagtaaattt gggcgtaacc gagtaagatt     4800
tggccatttt cgcgggaaaa ctgaataaga ggaagtgaaa tctgaataat tttgtgttac     4860
tcatagcgcg taannngtag ttattaatag taatcaatta cggggtcatt agttcatagc     4920
ccatatatgg agttccgcgt tacataactt acggtaaatg gcccgcctgg ctgaccgccc     4980
aacgaccccc gcccattgac gtcaataatg acgtatgttc ccatagtaac gccaataggg     5040
actttccatt gacgtcaatg ggtggagtat ttacggtaaa ctgcccactt ggcagtacat     5100
caagtgtatc atatgccaag tacgcccct attgacgtca atgacggtaa atggcccgc     5160
tggcattatg cccagtacat gaccttatgg gactttccta cttggcagta catctacgta     5220
ttagtcatcg ctattaccat ggtgatgcgg ttttggcagt acatcaatgg gcgtggatag     5280
cggtttgact cacggggatt tccaagtctc caccccattg acgtcaatgg gagtttgttt     5340
tggcaccaaa atcaacggga ctttccaaaa tgtcgtaaca actccgcccc attgacgcaa     5400
atgggcggta ggcgtgtacg gtgggaggtc tatataagca gagctggttt agtgaaccgt     5460
cagatccgct agaccatggc ctcctccgag gacgtcatca aggagttcat gcgcttcaag     5520
gtgcgcatgg agggctccgt gaacggccac gagttcgaga tcgagggcga gggcgagggc     5580
cgccctacg agggcaccca gaccgccaag ctgaaggtga ccaagggcgg ccccctgccc     5640
ttcgcctggg acatcctgtc ccctcagttc cagtacggct ccaaggccta cgtgaagcac     5700
cccgccgaca tccccgacta cttgaagctg tccttccccg agggcttcaa gtggggagcgc     5760
gtgatgaact tcgaggacgg cggcgtggtg accgtgaccc aggactcctc cctgcaggac     5820
ggcgagttca tctacaaggt gaagctgcgc ggcaccaact tccctccga cggccccgta     5880
atgcagaaga agaccatggg ctgggaggcc tccaccgagc ggatgtaccc cgaggacggc     5940
gccctgaagg gcgagatcaa gatgaggctg aagctgaagg acggcggcca ctacgacgcc     6000
gaggtcaaga ccacctacat ggccaagaag cccgtgcagc tgcccggcgc ctacaagacc     6060
gacatcaagc tggacatcac ctcccacaac gaggactaca ccatcgtgga acagtacgag     6120
cgcgccgagg gccgccactc caccggcgcc aatccaccgg atctagataa ctgatcataa     6180
tcagccatac cacatttgta gaggttttac ttgctttaaa aaacctccca cacctccccc     6240
tgaacctgaa acataaaatg aatgcaattg ttgttgttaa cttgtttatt gcagcttata     6300
atggttacaa ataaagcaat agcatcacaa atttcacaaa taaagcattt ttttcactgc     6360
attctagttg tggtttgtcc aaactcatca atgtatctta acgcgtctct agttattaat     6420
agtaatcaat tacggggtca ttagttcata gcccatatat ggagttccgc gttacataac     6480
ttacggtaaa tggcccgcct ggctgaccgc ccaacgaccc ccgcccattg acgtcaataa     6540
tgacgtatgt tcccatagta acgccaatag ggactttcca ttgacgtcaa tgggtggagt     6600
atttacggta aactgcccac ttggcagtac atcaagtgta tcatatgcca agtacgcccc     6660
ctattgacgt caatgacggt aaatggcccg cctggcatta tgcccagtac atgaccttat     6720
gggactttcc tacttggcag tacatctacg tattagtcat cgctattacc atggtgatgc     6780
ggttttggca gtacatcaat gggcgtggat agcggtttga ctcacgggga tttccaagtc     6840
tccacccat tgacgtcaat gggagtttgt tttggaacca aaatcaacgg gactttccaa     6900
aatgtcgtaa caactccgcc ccattgacgc ggaaatgggcgg taggcgtgta cggtgggagg     6960
tctatataag cagagctctc cctatcagtg atagagatct ccctatcagt gatagagatc     7020
tccctatcag tgatagagat ctccctatca gtgatagaga tcgagctgtt tagtgaaccg     7080
tcagatcgcc tggagacgcc atccacgctg ttttgacctc catagaagac accgaattca     7140
ggggatccaa tcggaaagcg gacgcggaat ttaaattgat ttttgcggta taagaatata     7200
tactgatatg tataccccgaa gtatgtcaaa aagaggtatg ctatgaagca gcgtattaca     7260
gtgacagttg acagcgacag ctatcagttg ctcaaggcat atatgatgtc aatatctccg     7320
gtctggtaag cacaaccatg cagaatgaag cccgtcgtct gcgtgccgaa cgctggaaag     7380
cggaaaatca ggaagggatg gctgaggtcg cccggtttat tgaaatgaac ggctctttg     7440
ctgacgagaa caggggctgg tgaaatgcag tttaaggttt acacctataa aagagagagc     7500
cgttatcgtc tgtttgtgga tgtacagagt gatattattg acacgcccgg gcgacggatg     7560
gtgatcccc tggccagtgc acgtctgctg tcagataaag tctcccgtga acttttcactg     7620
gtggtgcata tcggggatga agctggcgc atgatgacca ccgatatggc cagtgtgccg     7680
gtctccgtta tcggggaaga agtggctgat ctcagccacc gcgaaaatga catcaaaaac     7740
gccattaacc tgatgttctg gggaatataa atgtcaggct cccttataca cagccagtct     7800
gcagctcgct cttcatttaa atcgagtatc ccgtgagcgc tttctagaga tacggccgc     7860
taaacccgct gatcagcctc gactgtgcct tctagttgcc agccatctgt tgtttgcccct     7920
tccccgtgc cttccttgac cctggaaggt gccactccca ctgtccttc ctaataaaat     7980
gaggaaattg catcgcattg tctgagtagg tgtcattcta ttctgggggg tggggtgggg     8040
caggacagca agggggagga ttgggaagac aatagcaggc atgctgggga tgcggtgggc     8100
tctatggctt ctgaggcgga aagaaccagg atctgctagg atctnntaag ggtgggaaag     8160
aatatataag gtgggggtct tatgtagttt tgtatctgtt ttgcagccag cgccgccgcc     8220
atgagcacca actcgtttga tggaagcatt gtgagctcat atttgacaac gcgcatgccc     8280
ccatgggccg gggtgcgtca gaatgtgatg ggctccagca ttgatggtcg ccccgtcctg     8340
cccgcaaact ctactacctt gacctacgag accgtgctg gaacgccgtt ggagactgca     8400
gcctccgccg ccgcttcagc cgctgcagcc accgcccgcg ggattgtgac tgactttgct     8460
ttcctgagcc cgcttgcaag cagtgcagct tcccgttcat ccgcccgcga tgacaagttg     8520
```

-continued

```
acggctcttt tggcacaatt ggattctttg acccgggaac ttaatgtcgt ttctcagcag   8580
ctgttggatc tgcgccagca ggtttctgcc ctgaaggctt cctcccctcc caatgcggtt   8640
taaaacataa ataaaaaacc agactctgtt tggatttgga tcaagcaagt gtcttgctgt   8700
ctttatttag gggttttgcg cgcgcggtag gcccgggacc agcggtctcg gtcgttgagg   8760
gtcctgtgta ttttttccag gacgtggtaa aggtgactct ggatgttcag atacatgggc   8820
ataagcccgt ctctggggtg gaggtagcac cactgcagag cttcatgctg cggggtggtg   8880
ttgtagatga tccagtcgta gcaggagcgc tgggcgtggt gcctaaaaat gtctttcagt   8940
agcaagctga ttgccagggg caggcccttg gtgtaagtgt ttacaaagcg gttaagctgg   9000
gatgggtgca tacgtgggga tatgagatgc atcttggact gtattttag gttggctatg    9060
ttcccagcca tatccctccg gggattcatg ttgtgcagaa ccaccagcac agtgtatccg   9120
gtgcacttgg gaaatttgtc atgtagctta gaaggaaatg cgtggaagaa cttgagacg    9180
cccttgtgac ctccaagatt ttccatgcat tcgtccataa tgatggcaat gggcccacgg    9240
gcggcggcct gggcgaagat atttctggga tcactaacgt catagttgtg ttccaggatg   9300
agatcgtcat aggccatttt tacaaagcgc gggcggaggg tgccagactg cggtataatg   9360
gttccatccg gcccaggggc gtagttaccc tcacagattt gcatttccca cgctttgagt   9420
tcagatgggg ggatcatgtc tacctgcggg gcgatgaaga aaacggtttc cggggtaggg   9480
gagatcagct gggaagaaag caggttcctg agcagctgcg acttaccgca gccggtgggc   9540
ccgtaaatca cacctattac cgggtgcaac tggtagttaa gagagctgca gctgccgtca   9600
tccctgagca gggggggccac ttcgttaagc atgtccctga ctcgcatgtt ttccctgacc   9660
aaatccgcca gaaggcgctc gccgcccagc gatagcagtt cttgcaagga agcaaagttt   9720
ttcaacggtt tgagaccgtc cgccgtaggc atgctttga gcgtttgacc aagcagttcc    9780
aggcggtccc acagctcggt cacctgctct acggcatctc gatccagcat atctcctcgt   9840
ttcgcgggtt ggggcggctt tcgctgtacg gcagtagtcg gtgctcgtcc agacgggcca   9900
gggtcatgtc tttccacggg cgcagggtcc tcgtcagcgt agtctgggtc acggtgaagg   9960
ggtgcgctcc gggctgcgcg ctggccaggg tgcgcttgag gctggtcctg ctggtgctga   10020
agcgctgccg gtcttcgccc tgcgcgtcgg ccaggtagca tttgaccatg gtgtcatagt   10080
ccagcccctc cgcggcgtgg cccttggcgc gcagcttgcc cttggaggag gcgccgcacg   10140
aggggcagtg cagactttg agggcgtaga gcttgggcgc gagaaatacc gattccgggg   10200
agtaggcatc cgcgccgcag gccccgcaga cggtctcgca ttccacgagc caggtgagct   10260
ctggccgttc ggggtcaaaa accaggtttc ccccatgctt tttgatgcgt ttcttacctc   10320
tggtttccat gagccggtgt ccacgctcgg tgacgaaaag gctgtccgtg tccccgtata   10380
cagacttgag aggcctgtcc tcgagcggtg ttccgcggtc ctcctcgtat agaaactcgg   10440
accactctga dacaaaggct cgcgtccagg ccagcacgaa ggaggctaag tgggaggggt   10500
agcggtcgtt gtccactagg gggtccactc gctccagggt gtgaagacac atgtcgccct   10560
cttcggcatc aaggaaggtg attggtttgt aggtgtaggc cacgtgaccg ggtgttcctg   10620
aaggggggct ataaaagggg gtggggggcgc gttcgtcctc actctcttcc gcatcgctgt   10680
ctgcgagggc cagctgttgg ggtgagtact ccctctgaaa agcgggcatg acttctgcgc   10740
taagattgtc agtttccaaa aacgaggagg atttgatatt cacctggccc gcggtgatgc   10800
ctttgagggt ggccgcatcc atctggtcag aaaagacaat ctttttgttg tcaagcttgg   10860
tggcaaacga cccgtagagg gcgttggaca gcaacttggc gatggagcgc agggtttggt   10920
ttttgtcgcg atcggcgcgc tccttggccg cgatgtttag ctgcacgtat tcgcgcgcaa   10980
cgcaccgcca ttcgggaaag acggtggtgc gctcgtcggg caccaggtgc acgcgccaac   11040
cgcggttgtg cagggtgaca aggtcaacgc tggtggctac ctctccgcgt aggcgctcgt   11100
tggtccagca gaggcggccg cccttgcgcg agcagaatgg cggtaggggg tctagctgcg   11160
tctcgtccgg ggggtctgcg tccacggtaa agacccccggg cagcaggcgc gcgtcgaagt   11220
agtctatctt gcatccttgc aagtctagcg cctgctgcca tgcgcgggcg gcaagcgcgc   11280
gctcgtatgg gttgagtggg ggaccccatg gcatggggtg ggtgagcgcg gaggcgtaca   11340
tgccgcaaat gtcgtaaacg tagagggggc ctctgagtat tccaagatat gtagggtagc   11400
atcttccacc gcggatgctg gcgcgcacgt aatcgtatag ttcgtgcgag ggagcgagga   11460
ggtcgggacc gaggttgcta cgggcgggct gctctgctcg gaagactatc tgcctgaaga   11520
tggcatgtga gttggatgat atggttggac gctggaagac gttgaagctg ggtctgtga    11580
gacctaccgc gtcacgcacg aaggaggcgt aggagtcgcg cagcttgttg accagctcgg   11640
cggtgacctg cacgtctagg gcgcagtagt ccagggtttc cttgatgatg tcatacttat   11700
cctgtccctt ttttttccac agctcgcggt tgaggacaaa ctcttcgcgg tctttccagt   11760
actcttggat cggaaacccg tcggcctccg aacggtaaga gcctagcatg tagaactggt   11820
tgacggcctg gtaggcgcag catcccttt ctacgggtag cgcgtatgcc tgcgcggcct    11880
tccggagcga ggtgtgggtg agcgcaaagg tgtccctgac catgactttg aggtactggt   11940
atttgaagtc agtgtcgtcg catccgccct gctcccagag caaaaagtcc gtgcgctttt   12000
tggaacgcgg atttggcagg gcgaaggtga catcgttgaa gagtatcttt cccgcgcgag   12060
gcataaagtt gcgtgtgatg cggaagggtc ccggcacctc ggaacggttg ttaattacct   12120
gggcggcgag cacgatctcg tcaaagccgt tgatgttgtg gcccacaatg taaagttcca   12180
agaagcgcgg gatgcccttg atggaaggca attttttaag ttcctcgtag gtgagctctt   12240
cagggggagct gagcccgtgc tctgaaaggg cccagtctgc aagatgaggg ttggaagcga   12300
cgaatgagct ccacaggtca cgggccatta gcatttgcag gtggtcgcga aaggtcctaa   12360
actggcgacc tatggccatt ttttctgggg tgatgcagta gaaggtaagc gggtcttgtt   12420
cccagccgtc ccatccaagg ttcgcggcta ggtctcgcgc ggcagtcact agaggctcat   12480
ctccgccgaa cttcatgacc agcatgaagg gcacgagctg cttcccaaag gcccccatcc   12540
aagtataggt ctctacatcg taggtgacaa agagacgctc ggtgcgagga tgcgagccga   12600
tcgggaagaa ctggatctcc cgccaccaat tggaggagtg gctattgatg tggtgaaagt   12660
agaagtccct gcgacgggcc gaacactcgt gctggctttt gtaaaaacgt gcgcagtact   12720
ggcagcggtg cacgggctgt acatcctgca cgaggttgac ctgacgaccg cgcacaagga   12780
agcagagtgg gaatttgagc ccctcgcctg gcgggtttgg ctggtggtct tctacttcgg   12840
ctgcttgtcc ttgaccgtct ggctgctcga ggggagttac ggtggatcgg accaccacgc   12900
cgcgcgagcc caaagtccag atgtccgcgc gcggcggtcg gagcttgatg acaacatcgc   12960
gcagatggga gctgtccatg gtctggagct cccgcggcgt caggtcaggc gggagctcct   13020
gcaggtttac ctcgcataga cgggtcaggg cgcgggctag atccaggtga tacctaattt   13080
ccaggggctg gttggtggcg gcgtcgatgg cttgcaagag gccgcatccc cgcggcgcga   13140
ctacggtacc gcgcggcggg cggtgggccg cggggggtgtc cttggatgat gcatctaaaa   13200
gcggtgacgc gggcgagccc ccggaggtag gggggggctcc ggaccgccg ggagagggggg   13260
```

-continued

```
caggggcacg tcggcgccgc gcgcgggcag gagctggtgc tgcgcgcgta ggttgctggc   13320
gaacgcgacg acgcggcggt tgatctcctg aatctggcgc ctctgcgtga agacgacggg   13380
cccggtgagc ttgagcctga aagagagttc gacagaatca atttcggtgt cgttgacggc   13440
ggcctggcgc aaaatctcct gcacgtctcc tgagttgtct tgataggcga tctcggccat   13500
gaactgctcg atctcttcct cctggagatc tccgcgtccg gctcgctcca cggtggcggc   13560
gaggtcgttg gaaatgcggg ccatgagctg cgagaaggcg ttgaggcctc cctcgttcca   13620
gacgcggctg tagaccacgc cccttcggc atcgcgggcg cgcatgacca cctgcgcgag   13680
attgagctcc acgtgccggg cgaagacggc gtagtttcgc aggcgctgaa agaggtagtt   13740
gagggtggtg gcggtgtgtt ctgccacgaa gaagtacata acccagcgtc gcaacgtgga   13800
ttcgttgata tcccccaagg cctcaaggcg ctccatggcc tcgtagaagt ccacggcgaa   13860
gttgaaaaac tgggagttgc gcgccgacac ggttaactcc tcctccagaa gacggatgag   13920
ctcggcgaca gtgtcgcgca cctcgcgctc aaaggctaca ggggcctctt cttcttcttc   13980
aatctcctct tccataaggg cctcccttc ttcttcttct ggcggcggtg gggaggggg   14040
gacacggcgg cgacgacggc gcaccgggag gcggtcgaca aagcgctcga tcatctcccc   14100
gcggcgacgg cgcatggtct cggtgacggc gcggccgttc tcgcggggc gcagttggaa   14160
gacgccgccc gtcatgtccc ggttatgggt tggcggggg ctgccatgcg gcagggatac   14220
ggcgctaacg atgcatctca acaattgttg tgtaggtact ccgccgccga gggacctgag   14280
cgagtccgca tcgaccggat cggaaaacct ctcgagaaag gcgtctaacc agtcacagtc   14340
gcaaggtagg ctgagcaccg tggcgggcgg cagcgggcgg cggtcggggt tgtttctggc   14400
ggaggtgctg ctgatgatgt aattaaagta ggcggtcttg agacggcgga tggtcgacag   14460
aagcaccatg tccttgggtc cggcctgctg aatgcgcagg cggtcggcca tgccccaggc   14520
ttcgttttga catcggcgca ggtctttgta gtagtcttgc atgagccttt ctaccggcaa   14580
ttcttcttct ccttcctctt gtcctgcatc tcttgcatct atcgctgcgg cggcggcgga   14640
gtttggccgt aggtggcgcc ctcttcctcc catgcgtgtg accccgaagc ccctcatcgg   14700
ctgaagcagg gctaggtcgg cgacaacgcg ctcggctaat atggcctgct gcacctgcgt   14760
gagggtagac tggaagtcat ccatgtccac aaagcggtag tatcgcccg tgttgatggt   14820
gtaagtgcag ttggccataa cggaccagtt aacggtctgg tgaccccggct gcgagagctc   14880
ggtgtacctg agacgcgagt aagccctcga gtcaaatacg tagtcgttgc aagtccgcac   14940
caggtactgg tatcccacca aaaagtgcgg cggcggctgg cggtagaggg gccagcgtag   15000
ggtggccggg gctccggggg cgagatcttc caacataagg cgatgatatc cgtagatgta   15060
cctggacatc caggtgatgc cggcggcggt ggtggaggcg cgcggaaagt cgcggacgcg   15120
gttccagatg ttgcgcagcg gcaaaaagtg ctccatggtc gggacgctct ggccggtcag   15180
gcgcgcgcaa tcgttgacgc tctaccgtgc aaaaggagag cctgtaagcg ggcactcttc   15240
cgtggtctgg tggatataatt cgcaagggta tcatggcgga cgaccggggt tcgagcccg   15300
tatccggccg tccgccgtga tccatgcggt taccgcccgc gtgtcgaacc caggtgtgcg   15360
acgtcagaca acggggagt gctccttttg gcttccttcc aggcgcggcg gctgctgcgc   15420
tagcttttt ggccactggc cgcgcgcagc gtaagcggtt aggctggaaa gcgaaagcat   15480
taagtggctc gctccctgta gccggagggt tattttccaa gggttgagtc gcgggacccc   15540
cggttcgagt ctcggaccgg ccggactgcg gcgaacgggg gtttgcctcc ccgtcatgca   15600
agaccccgct tgcaaattcc tccggaaaca gggacgagcc cctttttgc ttttcccaga   15660
tgcatccggt gctgcggcag atgcgccccc ctcctcagca gcggcaagag caagagcagc   15720
ggcagacatg cagggcaccc tccctcctc ctaccgcgtc aggaggggcg acatccgcgg   15780
ttgacgcggc agcagatggt gattacgaac ccccgcggcg ccgggcccgg cactacctgg   15840
acttggagga gggcgagggc ctggcgcggc taggagcgcc ctctcctgag cggtacccaa   15900
gggtgcagct gaagcgtgat acgcgtgagg cgtacgtgcc gcggcagaac ctgtttcgcg   15960
accgcgaggg agaggagccc gaggagatgc gggatcgaaa gttccacgca gggcgcgagc   16020
tgcggcatgg cctgaatcgc gagcggttgc tgcgcgagga ggactttgag cccgacgcgc   16080
gaaccgggat tagtcccgcg cgcgcacacg tggcggccgc cgacctggta accgcatacg   16140
agcagacggt gaaccaggag attaactttc aaaaaagctt taacaaccac gtgcgtacgc   16200
ttgtggcgcg cgaggaggtg gctataggac tgatgcatct gtgggacttt gtaagcgcgc   16260
tggacaaaa cccaaatagc aagccgctca tggcgcagct gttccttata gtgcagcaca   16320
gcagggacaa cgaggcattc agggatgcgc tgctaaacat agtagagccc gagggccgct   16380
ggctgctcga tttgataaac atcctgcaga gcatagtggt gcaggagcgc agcttgagcc   16440
tggctgacaa ggtggccgcc atcaactatt ccatgcttag cctgggcaag ttttacgccc   16500
gcaagatata ccatacccct tacgttccca tagacaagga ggtaaagatc gagggttct   16560
acatgcgcat ggcgctgaag gtgcttacct tgagcgacga cctgggcgtt tatcgcaacg   16620
agcgcatcca caaggccgtg agcgtgagcc ggcggcgcga gctcagcgac cgcgagctga   16680
tgcacagcct gcaaagggcc ctggctggca cgggcagcgg cgatagagag gccgagtcct   16740
actttgacgc gggcgctgac ctgcgctggg ccccaagccg acgcgccctg gaggcagctg   16800
gggccggacc tgggctggcg gtggcacccg cgcgcgtgga caacgtcggc gcgtggagg   16860
aatatgacga ggacgatgag tacgagccag aggacggcga gtactaagcg gtgatgtttc   16920
tgatcagatg atgcaagacg caacggaccc ggcggtgcgg gcggcgctgc agagccagcc   16980
gtccggcctt aactccacgg acgactggcg ccaggtcatg gaccgcatca tgtcgctgac   17040
tgcgcgcaat cctgacgcgt tccggcagca gccgcagcgc aacggcctct ccgcaattct   17100
ggaagcggtg gtcccggcgc gcgcaaaccc cacgcacgag aaggtgctgg cgatcgtaaa   17160
cgcgctggcc gaaaacaggg ccatccggcc cgacgaggcc ggcctggtct acgacgcgct   17220
gcttcagcgc gtggctcgtt acaacagcgg caacgtgcag accaacctgg accggctggt   17280
gggggatgtg cgcgaggccg tggcgcagcg tgagcgcgcg cagcagcagg gcaacctggg   17340
ctccatggtt gcactaaacg ccttcctgag tacacagccc ggccacgtgc gcgggggaca   17400
ggaggactac accaactttg tgagcgcact gcggctaatg gtgactgaga caccgcaaag   17460
tgaggtgtac cagtctgggc cagactattt tttccagacc agtagacaag gcctgcagac   17520
cgtaaacctg agccaggctt tcaaaaactt gcaggggctg tgggggtgc gggctcccac   17580
aggcgaccgc gcgaccgtgt ctagcttgct gacgcccaac tcgcgcctgt tgctgctgct   17640
aatagccgct ttcacggaca gtggcagcgt gtcggcagcgt acatacctag gtcacttgct   17700
gacactgtac cgcgcaggcca taggtcaggc gcatgtggac gagcatactt tccaggagat   17760
tacaagtgtc agccgcgcgc tggggcagga ggacacgggc agcctggagg caaccctaaa   17820
ctacctgctg accaaccggc ggcagaagat ccccctcgttg cacagtttaa acagcgagga   17880
ggagcgcatt ttgcgctacg tgcagcagag cgtgagcctt aacctgatgc gcgacggggt   17940
aacgcccagc gtggcgctgg acatgaccgc gcgcaacatg gaaccgggca tgtatgcctc   18000
```

-continued

```
aaaccggccg  tttatcaacc  gcctaatgga  ctacttgcat  cgcgcggccg  ccgtgaaccc  18060
cgagtatttc  accaatgcca  tcttgaaccc  gcactggcta  ccgcccctg   gtttctacac  18120
cggggggattc gaggtgcccg  agggtaacga  tggattcctc  tgggacgaca  tagacgacag  18180
cgtgtttttcc ccgcaaccgc  agaccctgct  agagttgcaa  cagcgcgagc  aggcagaggc  18240
ggcgctgcga  aaggaaagct  tccgcaggcc  aagcagcttg  tccgatctag  gcgctgcggc  18300
cccgcggtca  gatgctagta  gcccatttcc  aagcttgata  gggtctctta  ccagcactcg  18360
caccacccgc  ccgcgcctgc  tgggcgagga  ggagtaccta  aacaactcgc  tgctgcagcc  18420
gcagcgcgaa  aaaaacctgc  ctccggcatt  tcccaacaac  gggatagaga  gcctagtgga  18480
caagatgagt  agatggaaga  cgtacgcgca  ggagcacagg  gacgtgccag  gcccgcgccc  18540
gcccacccgt  cgtcaaaggc  acgaccgtca  gcggggtctg  gtgtgggagg  acgatgactc  18600
ggcagacgac  agcagcgtcc  tggatttggg  agggagtggc  aacccgtttg  cgcaccttcg  18660
ccccaggctg  gggagaatgt  tttaaaaaaa  aaaaagcatg  atgcaaaata  aaaaactcac  18720
caaggccatg  gcaccgagcg  ttggtttttct  tgtattcccc  ttagtatgcg  gcgcgcggcg  18780
atgtatgagg  aaggtcctcc  tccctcctac  gagagtgtgg  tgagcgcggc  gccagtggcg  18840
gcggcgctgg  gttctcccctt cgatgctccc  ctggacccgc  cgtttgtgcc  tccgcggtac  18900
ctgcggccta  ccgggggggag aaacagcatc  cgttactctg  agttggcacc  cctattcgac  18960
accacccgtg  tgtacctggt  ggacaacaag  tcaacggatg  tggcatccct  gaactaccag  19020
aacgaccaca  gcaactttct  gaccacggtc  attcaaaaca  atgactacag  cccggggggag 19080
gcaagcacac  agaccatcaa  tcttgacgac  cggtcgcact  ggggcggcga  cctgaaaacc  19140
atcctgcata  ccaacatgcc  aaatgtgaac  gagttcatgt  ttaccaataa  gtttaaggcg  19200
cgggtgatgg  tgtcgcgctt  gcctactaag  gacaatcagg  tggagctgaa  atacgagtgg  19260
gtggagttca  cgctgcccga  gggcaactac  tccgagacca  tgaccataga  ccttatgaac  19320
aacgcgatcg  tggagcacta  cttgaaagtg  ggcagacaga  acgggggttct  ggaaagcgac  19380
atcggggtaa  agtttgacac  ccgcaacttc  agactggggg  ttgaccccgt  cactggtctt  19440
gtcatgcctg  gggtatatac  aaacgaagcc  ttccatccag  acatcatttt  gctgccagga  19500
tgcgggggtgg  acttcaccca  cagccgcctg  agcaacttgt  tgggcatccg  caagcggcaa  19560
cccttccagg  agggcttttag gatcacctac  gatgatctgg  agggtggtaa  cattcccgca  19620
ctgttggatg  tggacgccta  ccaggcgagc  ttgaaagatg  acaccgaaca  gggcggggggt 19680
ggcgcaggcg  gcagcaacag  cagtggcagc  ggcgcgcgaag agaactccaa  cgcggcagcc  19740
gcggcaatgc  agccggtgga  ggacatgaac  gatcatgcca  ttcgcggcga  cacctttgcc  19800
acacgggctg  aggagaagcg  cgctgaggcc  gaagcagcgg  ccgaagctgc  cgcccccgct  19860
gcgcaacccg  aggtcgagaa  gcctcagaag  aaaccggtga  tcaaacccct  gacagaggac  19920
agcaagaaac  gcagttacaa  cctaataagc  aatgacagca  ccttcacccca gtaccgcagc  19980
tggtaccttg  catacaacta  cggcgaccct  cagaccggaa  tccgctcatg  gacctgctt   20040
tgcactcctg  acgtaacctg  cggctcggag  caggtctact  ggtcgttgcc  agacatgatg  20100
caagaccccg  tgaccttccg  ctccacgcgc  cagatcagca  acttttccggt ggtgggcgcc  20160
gagctgttgc  ccgtgcactc  caagagcttc  tacaacgacc  aggccgtcta  ctcccaactc  20220
atccgccagt  ttacctctct  gacccacgtg  ttcaatcgct  ttcccgagaa  ccagattttg  20280
gcgcgccccgc cagcccccac  catcaccacc  gtcagtgaaa  acgttcctgc  tctcacagat  20340
cacgggacgc  taccgctgcg  caacagcatc  ggaggagtcc  agcgagtgac  cattactgac  20400
gccagacgcc  gcacctgccc  ctacgtttac  aaggccctgg  gcatagtctc  gccgcgcgtc  20460
ctatcgagcc  gcactttttg  agcaagcatg  tccatcctta  tatcgcccag  caataacaca  20520
ggctgggggc  tgcgcttccc  aagcaagatg  tttggcgggg  ccaagaagcg  ctccgaccaa  20580
cacccagtgc  gcgtgcgcgg  gcactaccgc  gcgcccctggg  gcgcgcacaa  acgcggccgc  20640
actgggcgca  ccaccgtcga  tgacgccatc  gacgcggtgg  tggaggaggc  gcgcaactac  20700
acgcccacgc  cgccaccagt  gtccacagtg  gacgcggcca  ttcagaccgt  ggtgcgcgga  20760
gcccggcgct  atgctaaaat  gaagagacgg  cggaggcgcg  tagcacgtcg  ccaccgccgc  20820
cgacccggca  ctgccgccca  acgcgcggcg  gcggccctgc  ttaaccgcgc  acgtcgcacc  20880
ggccgacggg  cggccatgcg  ggccgctcga  aggctggccg  cgggtattgt  cactgtgccc  20940
cccaggtcca  ggcgacgagc  ggccgccgca  gcagccgcgg  ccattagtgc  tatgactcag  21000
ggtcgcaggg  gcaacgtgta  ttggggtgcgc gactcggtta  gcggcctgcg  cgtgcccgtg  21060
cgcacccgcc  ccccgcgcaa  ctagattgca  agaaaaaaact acttagactc  gtactgttgt  21120
atgtatccag  cggcggcggc  gcgcaacgaa  gctatgtcca  agcgcaaaat  caaagaagag  21180
atgctccagg  tcatcgcgcc  ggagatctat  ggccccccga  agaaggaaga  gcaggattac  21240
aagcccgaa   agctaaagcg  ggtcaaaaag aaaaagaaag atgatgatga  tgaacttgac  21300
gacgaggtgg  aactgctgca  cgctcaccgcg cccaggcgac  gggtacagtg  gaaaggtcga  21360
cgcgtaaaac  gtgtttttgcg acccggcacc  accgtagtct  ttacgcccgg  tgagcgctcc  21420
acccgcacct  acaagcgcgt  gtatgatgag  gtgtacggcg  acgaggacct  gcttgagcag  21480
gccaacgagc  gcctcgggga  gtttgcctac  ggaaagcggc  ataaggacat  gctggcgttg  21540
ccgctggacg  agggcaaccc  aacacctagc  ctaaagcccg  taacactgca  gcaggtgctg  21600
cccgcgcttg  caccgtccga  agaaaagcgc  ggcctaaagc  gcgagtctgg  tgacttggca  21660
cccaccgtgc  agctgatggt  acccaagcgc  cagcgactgg  aagatgtctt  ggaaaaaatg  21720
accgtggaac  ctgggctgga  gcccgaggtc  cgcgtgcggc  caatcaagca  ggtggcgccg  21780
ggactgggcg  tgcagaccgt  ggacgttcag  atacccacta  ccagtagcac  cagtattgcc  21840
accgccacag  agggcatgga  gacacaaacg  tccccggttg  cctcagcggt  ggcggatgcc  21900
gcggtgcagg  cggtcgctgc  ggccgcgtcc  aagacctcta  cggaggtgca  aacgacccg   21960
tggatgtttc  gcgtttcagc  cccccggcgc  ccgcgcggtt  cgaggaagta  cggcgccgcc  22020
agcgcgctac  tgcccgaata  tgccctacat  ccttccattg  cgcctaccccc cggctatcgt  22080
ggctacacct  accgccccag  aagacgagca  actacccgac  gccgaaccac  cactggaacc  22140
cgccgccgcc  gtcgccgtcg  ccagcccgtg  ctggccccga  tttccgtgcg  cagggtggct  22200
cgcgaaggag  gcaggaccct  ggtgctgcca  acagcgcgct  accaccccag  catcgtttaa  22260
aagccggtcc  ttgtggttct  tgcagatatg  gccctcacct  gccgcctccg  tttcccggtg  22320
ccgggattcc  gaggaagaat  gcaccgtagg  aggggcatgg  ccggccacgg  cctgacgggc  22380
ggcatgcgtc  gtgcgcacca  ccggcgcgcg  cgcgcgtgac  accgtcgcat  gcgcgggcgt  22440
atcctgcccc  tccttattcc  actgatcgcc  gcggcgattg  gcgccgtgcc  cggaattgca  22500
tccgtggcct  tgcaggcgca  gagacactga  ttaaaaacaa  gttgcatgtg  gaaaaatcaa  22560
aataaaaagt  ctggactctc  acgctcgctt  ggtcctgtaa  ctattttgta  gaatggaaga  22620
catcaacttt  gcgtctctgg  ccccgcgaca  cggctcgcgc  ccgttcatgg  gaaactggca  22680
agatatcggc  accagcaata  tgagcggtgg  cgccttcagc  tggggctcgc  tgtggagcgg  22740
```

-continued

```
cattaaaaat ttcggttcca ccgttaagaa ctatggcagc aaggcctgga acagcagcac   22800
aggccagatg ctgagggata agttgaaaga gcaaaatttc caacaaaagg tggtagatgg   22860
cctggcctct ggcattagcg gggtggtgga cctggccaac caggcagtgc aaaataagat   22920
taacagtaag cttgatcccc gccctcccgt agaggagcct ccaccggccg tggagacagt   22980
gtctccagag gggcgtggcg aaaagcgtcc gcgccccgac agggaagaaa ctctggtgac   23040
gcaaatagac gagcctccct cgtacgagga ggcactaaag caaggcctgc ccaccacccg   23100
tcccatcgcg cccatggcta ccggagtgct gggccagcac acaccgtaa cgctggacct   23160
gcctcccccc gccgacaccc agcagaaacc tgtgctgcca ggcccgaccg ccgttgttgt   23220
aacccgtcct agccgcgcgt ccctgcgccg cgccgccagc ggtccgcgat cgttgcggcc   23280
cgtagccagt ggcaactggc aaagcacact gaacagcatc gtgggtctgg gggtgcaatc   23340
cctgaagcgc cgacgatgct tctgaatagc taacgtgtcg tatgtgtgtc atgtatgcgt   23400
ccatgtcgcc gccagaggag ctgctgagcc gccgcgcgcc cgctttccaa gatggctacc   23460
ccttcgatga tgccgcagtg gtcttacatg cacatctcgg gccaggacgc ctcggagtac   23520
ctgagccccg ggctggtgca gtttgcccgc gccaccgaga cgtacttcag cctgaataac   23580
aagtttagaa accccacggt ggcgcctacg cacgacgtga ccacagaccg gtcccagcgt   23640
ttgacgctgc ggttcatccc tgtggaccgt gaggatactg cgtactcgta caaggcgcgg   23700
ttcaccctag ctgtgggtga taaccgtgtg ctggacatgg cttccacgta ctttgacatc   23760
cgcggcgtgc tggacagggg ccctactttt aagccctact ctggcactgc ctacaacgcc   23820
ctggctccca agggtgcccc aaatccttgc gaatgggatg aagctgctac tgctcttgaa   23880
ataaacctag aagaagagga cgatgacaac gaagacgaag tagacgagca agctgagcag   23940
caaaaaactc acgtatttgg gcaggcgcct tattctggta taaatattac aaaggagggt   24000
attcaaatag gtgtcgaagg tcaaacacct aaatatgccg ataaaacatt tcaacctgaa   24060
cctcaaatag gagaatctca gtggtacgaa actgaaatta atcatgcagc tgggagagtc   24120
cttaaaaaga ctaccccaat gaaaccatgt tacggttcat atgcaaaacc cacaaatgaa   24180
aatggagggc aaggcattct tgtaaagcaa caaaatggaa agctagaaag tcaagtggaa   24240
atgcaatttt tctcaactac tgaggcgacc gcaggcaatg gtgataactt gactcctaaa   24300
gtggtattgt acagtgaaga tgtagatata gaaaccccag acactcatat ttcttacatg   24360
cccactatta aggaaggtaa ctcacgagaa ctaatgggcc aacaatctat gcccaacagg   24420
cctaattaca ttgcttttag ggacaatttt attggtctaa tgtattacaa cagcacgggt   24480
aatatgggtg ttctggcggg ccaagcatcg cagttgaatg ctgttgtaga tttgcaagac   24540
agaaacacag agcttttcata ccagcttttg cttgattcca ttggtgatag aaccaggtac   24600
ttttctatgt ggaatcaggc tgttgacagc tatgatccag atgttagaat tattgaaaat   24660
catgaactg aagatgaact tccaaattac tgctttccac tggggaggtgt gattaataca   24720
gagactctta ccaaggtaaa acctaaaaca ggtcaggaaa atggatggga aaaagatgct   24780
acagaatttt cagataaaaa tgaaataaga gttggaaata attttgccat ggaaatcaat   24840
ctaaatgcca acctgtggag aaatttcctg tactccaaca tagcgctgta tttgcccgac   24900
aagctaaagt acagtccttc caacgtaaaa atttctgata acccaaacac ctacgactac   24960
atgaacaagc gagtggtggc tcccgggtta gtggactgct acattaacct tggagcacgc   25020
tggtcccttg actatatgga caacgtcaac ccatttaacc accacgcaa tgctggcctg   25080
cgctaccgct caatgttgct gggcaatggt cgctatgtgc ccttccacat ccaggtgcct   25140
cagaagttct ttgccattaa aaacctcctt ctcctgccgg gctcatacac ctacgagtgg   25200
aacttcagga aggatgttaa catggttctg cagagctccc taggaaatga cctaaggggtt   25260
gacggagcca gcattaagtt tgatagcatt tgccttacg ccaccttctt ccccatggcc   25320
cacaacaccg cctccacgct tgaggccatg cttagaaacg acaccaacga ccagtccttt   25380
aacgactatc tctccgccgc caacatgctc taccctatac ccgccaacgc taccaacgtg   25440
cccatatcca tccctcccg caactgggcg gctttccgcg gctgggcctt cacgcgcctt   25500
aagactaagg aaaccccatc actggggctcg ggctacgacc cttattacac ctactctggc   25560
tctatacct acctagatgg aaccttttac ctcaaccaca cctttaagaa ggtggccatt   25620
accttttgact cttctgtcag ctggcctggc aatgaccgcc tgcttacccc caacgagttt   25680
gaaattaagc gctcagttga cggggaggt tacaacgttg cccagtgtaa catgaccaaa   25740
gactggttcc tggtacaaat gctagctaac tacaacattg gctaccaggg cttctatatc   25800
ccagagagct acaaggaccg catgtactcc ttctttagaa acttccagcc catgagccgt   25860
caggtggtgg atgatactaa atacaaggac taccaacagg tgggcatcct acaccaacac   25920
aacaactctg gatttgttgg ctaccttgcc cccaccatgc gcgaaggaca ggcctaccct   25980
gctaacttcc cctatccgct tataggcaag accgcagttg acagcattac ccagaaaaag   26040
tttctttgcg atcgcaccct ttggcgcatc ccattctcca gtaactttat gtccatgggc   26100
gcactcacag acctgggcca aaaccttctc tacgccaact ccgccacgc gctagacatg   26160
acttttgagg tggatcccat ggacgagccc accttcttt atgtttttgtt tgaagtcttt   26220
gacgtggtcc gtgtgcaccg gccgcaccgc ggcgtcatcg aaaccgtgta cctgcgcacg   26280
cccttctcgg ccggcaacgc cacaacataa agaagcaagc aacatcaaca acagctgccg   26340
ccatgggctc cagtgagcag gaactgaaag ccattgtcaa agatcttggt tgtgggccat   26400
attttttggg cacctatgac aagcgctttc caggctttgt ttctccacac aagctcgcct   26460
gcgccatagt caatacggcc ggtcgcgaga ctgggggcgt acactggatg gcctttgcct   26520
ggaacccgca ctcaaaaaca tgctacctct ttgagccctt ggctttttct gaccagcgac   26580
tcaagcaggt ttaccagttt gagtacgagt cactcctgcg ccgtagcgcc attgcttctt   26640
cccccgaccg ctgtataacg ctggaaaagt ccacccaaag cgtacagggg cccaactcgg   26700
ccgcctgtga actattctgc tgcatgtttc tccacgcctt tgccaactgg ccccaaactc   26760
ccatggatca caaccccacc atgaaccta ttaccgggggt acccaactcc atgctcaaca   26820
gtccccaggt acagcccacc ctgcgtcgca accaggaaca gctctacagc ttcctggagc   26880
gccactcgcc ctacttccgc agccacagtg cgcagattag gagcgccact tctttttgtc   26940
acttgaaaaa catgtaaaaa taatgtacta gagacacttt caataaaggc aaatgctttt   27000
atttgtacac tctcgggtga ttatttaccc caccctgc cgtctgcgcc gtttaaaaat   27060
caaagggggt ctgccgcgca tcgctatgcg ccactggcag ggacacgttg cgatactggt   27120
gtttagtgct ccacttaaac tcaggcacaa ccatccgcgg aagtcggtg aagtttcac   27180
tccacaggtc gcgcaccatc accaacgcgt ttagcaggtc gggcgccgat atcttgaagt   27240
cgcagttggg gcctccgccc tgcgcgcgcg agttgcgata cacagggttg cagcactgga   27300
acactatcag cgccgggtgg tgcacgctgg ccagcacgct cttgtcggag atcagatccg   27360
cgtccaggtc ctccgcgttg ctcagggcga acggagtcaa ctttggtagc tgccttccca   27420
aaaagggcgc gtgcccaggc tttgagttgc actcgcaccg tagtggcatc aaaaggtgac   27480
```

-continued

```
cgtgcccggt ctgggcgtta ggatacagcg cctgcataaa agccttgatc tgcttaaaag   27540
ccacctgagc ctttgcgcct tcagagaaga acatgccgca agacttgccg gaaaactgat   27600
tggccggaca ggccgcgtcg tgcacgcagc accttgcgtc ggtgttggag atctgcacca   27660
catttcggcc ccaccggttc ttcacgatct tggccttgct agactgctcc ttcagcgcgc   27720
gctgcccgtt ttcgctcgtc acatccattt caatcacgtg ctccttattt atcataatgc   27780
ttccgtgtag acacttaagc tcgccttcga tctcagcgca gcggtgcagc cacaacgcgc   27840
agcccgtggg ctcgtgatgc ttgtaggtca cctctgcaaa cgactgcagg tacgcctgca   27900
ggaatcgccc catcatcgtc acaaaggtct tgttgctggt gaaggtcagc tgcaacccgc   27960
ggtgctcctc gttcagccag gtcttgcata cggccgccaa agcttccact tggtcaggca   28020
gtagtttgaa gttcgccttt agatcgttat ccacgtggta cttgtccatc agcgcgcgcg   28080
cagcctccat gcccttctcc cacgcagaca cgatcggcac actcagcggg ttcatcaccg   28140
taatttcact ttccgcttcg ctgggctctt cctcttcctc ttgcgtccgc ataccacgcg   28200
ccactgggtc gtcttcattc agccgccgca ctgtgcgctt acctcctttg ccatgcttga   28260
ttagcaccgg tgggttgctg aaacccacca tttgtagcgc cacatcttct ctttcttcct   28320
cgctgtccac gattacctct ggtgatggcg ggcgctcggg cttgggagaa gggcgcttct   28380
tttttcttctt gggcgcaatg gccaaatccg ccgccgaggt cgatggccgc gggctgggtg   28440
tgcgcggcac cagcgcgtct tgtgatgagt cttcctcgtc ctcggactcg atacgccgcc   28500
tcatccgctt ttttgggggc gcccggggag gcggcggcga cgggacggg gacgacacgt   28560
cctccatggt tggggacgt cgcgcgcgcac cgcgtccgcg ctcgggggtg gtttcgcgct   28620
gctcctcttc ccgactggcc atttccttct cctataggca gaaaaagatc atggagtcag   28680
tcgagaagaa ggacagccta accgcccct ctgagttcgc caccaccgcc tccaccgatg   28740
ccgccaacgc gcctaccacc ttccccgtcg aggcacccc gcttggagg gaggaagtga   28800
ttatcgagca ggacccaggt tttgtaagcg aagacgacga ggaccgctca gtaccaacag   28860
aggataaaaa gcaagaccag gacaacgcag aggcaaacga ggaacaagtc gggcggggggg   28920
acgaaaggca tggcgactac ctagatgtgg gagacgacgt gctgttgaag catctgcagc   28980
gccagtgcgc cattatctgc gacgcgttgc aagagcgcag cgatgtgccc ctcgccatag   29040
cggatgtcag ccttgcctac gaacgccacc tattctcacc gcgcgtaccc cccaaacgcc   29100
aagaaaacgg cacatgcgag cccaacccgc gcctcaactt ctaccccgta tttgccgtgc   29160
cagaggtgct tgccacctat cacatctttt tccaaaactg caagataccc ctatcctgcc   29220
gtgccaaccg cagccgagcg gacaagcagc tggccttgcg gcagggcgct gtcatacctg   29280
atatcgcctc gctcaacgaa gtgccaaaaa tctttgaggg tcttggacgc gacgagaagc   29340
gcgcggcaaa cgctctgcaa caggaaaaca gcgaaaatga aagtcactct ggagtgttgg   29400
tggaactcga gggtgacaac gcgcgcctag ccgtactaaa acgcagcatc gaggtcaccc   29460
actttgccta cccggcactt aacctacccc ccaaggtcat gagcacagtc atgagtgagc   29520
tgatcgtgcg ccgtgcgcag cccctggaga gggatgcaaa tttgcaagaa caaacagagg   29580
agggcctacc cgcagttggc gacgagcagc tagcgcgctg gcttcaaacg cgcgagcctg   29640
ccgacttgga ggagcgacgc aaactaatga tggccgcagt gctcgttacc gtggagcttg   29700
agtgcatgca gcggttcttt gctgacccgg agatgcagcg caagctagag gaaacattgc   29760
actacacctt tcgacagggc tacgtacgcc aggcctgcaa gatctccaac gtggagctct   29820
gcaacctggt ctcctacctt ggaattttgc acgaaaaccg ccttgggcaa aacgtgcttc   29880
attccacgct caagggcgag gcgcgccgcg actacgtccg cgactgcgtt tacttatttc   29940
tatgctcac ctggcagacg gccatgggcg tttggcagca gtgcttggag gagtgcaacc   30000
tcaaggagct gcagaaactg ctaaagcaaa acttgaagga cctatgacg gccttcaacg   30060
agcgctccgt ggccgcgcac ctggcggaca tcattttccc cgaacgcctg cttaaaaccc   30120
tgcaacaggg tctgccagac ttcaccagtc aaagcatgtt gcagaacttt aggaactttta  30180
tcctagacgc ctcaggaatc ttgcccgcca cctgctgtgc acttcctagc gactttgtgc   30240
ccattaagta ccgcgaatgc cctccgccgc tttggggcca ctgctacctt ctgcagctag   30300
ccaactacct tgcctaccac tctgacataa tggaagacgt gagcggtgac ggtctactgg   30360
agtgtcactg tcgctgcaac ctatgcaccc cgcaccgctc cctggtttgc aattcgcagc   30420
tgcttaacga aagtcaaatt atcggtacct ttgagctgca gggtccctcg cctgacgaaa   30480
agtccggcgc tccgggggttg aaactcactc cggggctggt gacgtcggct taccttcgca   30540
aatttgtacc tgaggactac cacgcccacg agattaggtt ctacgaagac caatcccgcc   30600
cgccaaatgc ggagcttacc gcctgcgtca ttacccaggg ccacattctt ggccaattgc   30660
aagccatcaa caaagcccgc caagagtttc tgctacgaaa gggacggggg gtttacttgg   30720
acccccagtc cggcgaggag ctcaacccaa tccccccgcc gccgcagccc tatcagcagc   30780
agccgcgggc ccttgcttcc caggatggca cccaaaaaga agctgcagct gccgccgcca   30840
cccacgacg aggaggaata ctgggacagt caggcagagg aggttttgga cgaggaggag   30900
gaggacatga tggaagactg ggagagccta gacgaggaag cttccgaggt cgaagaggtg   30960
tcagacgaaa caccgtcacc ctcggtcgca ttccctcgc cggcgcccca gaaatcgaca   31020
accggttcca gcatggctac aacctccgct cctcaggccgc cggcggcact gcccgttcgc   31080
cgacccaacc gtagatggga caccactgga accaggccg gtaagtccaa gcagccgccg   31140
ccgttagccc aagagcaaca acagcgcaa ggctaccgct catggcgcgg gcacaagaac   31200
gccatagttg cttgcttgca agactgtggg ggcaacatct ccttcgcccg ccgctttctt   31260
ctctaccatc acggcgtggc cttccccgt aacatcctac attactaccg tcatctctac   31320
agcccatact gcaccggcgg cagcggcagc ggcagcaaca gcagcggcca cacagaagca   31380
aaggcgaccg gatagcaaga ctctgacaaa gcccaagaaa tccacagcgg cggcagcagc   31440
aggaggagga gcgctgcgtc tggcgcccaa cgaacccgta tcgacccgcg agcttagaaa   31500
caggattttt cccactctgt atgctatatt tcaacgagac aggggccaag aacaagagct   31560
gaaaataaaa aacaggtctc tgcgatccct caccccgacg tgcctgtatc acaaaagcga   31620
agatcagctt cggcgcacgc tggaagacgc ggaggctctc ttcagtaaat actgcgcgct   31680
gactcttaag gactagtttc gcgcccttt tcaaatttaa gcgcgaaaac tacgtcatct   31740
ccagcggcca cacccggcgc cagcacctgt cgtcagcgcc attatgagca aggaaattcc   31800
cacgccctac atgtggagtt accagccaca aatgggactt gcggctggag ctgcccaaga   31860
ctactcaacc cgaataaaact acatgagcgc gggaccccac atgatatccc gggtcaacgg   31920
aatccgcgcc caccgaaacc gaattctctt ggaacaggcg gctattacca ccacacctcg   31980
taataacctt aatcccgta gttgcccgc tgccctggtg taccaggaaa gtcccgctcc   32040
caccactgtg gtacttccca gagacgccca ggccgaagtt cagatgacta actcaggggc   32100
gcagcttgcg ggcggctttc gtcacagggt gcggtcgccc gggcagggta taactcacct   32160
gacaatcaga gggcgaggta ttcagctcaa cgacgagtcg gtgagctcct cgcttggtct   32220
```

-continued

```
ccgtccggac gggacatttc agatcggcgg cgccggccgt ccttcattca cgcctcgtca   32280
ggcaatccta actctgcaga cctcgtcctc tgagccgcgc tctggaggca ttggaactct   32340
gcaatttatt gaggagtttg tgccatcggt ctactttaac cccttctcgg gacctcccgg   32400
ccactatccg gatcaattta ttcctaactt tgacgcggta aaggactcgg cggacggcta   32460
cgactgaatg ttaagtggag aggcagagca actgcgcctg aaacacctgg tccactgtcg   32520
ccgccacaag tgctttgccc gcgactccgg tgagtttgc tactttgaat tgcccgagga   32580
tcatatcgag ggcccggcgc acggcgtccg gcttaccgcc cagggagagc ttgcccgtag   32640
cctgattcgg gagtttaccc agcgcccct gctagttgag cgggacaggg gaccctgtgt   32700
tctcactgtg atttgcaact gtcctaacct tggattacat caagatcctc tagttataac   32760
tagagtaccc ggggatctta ttccctttaa ctaataaaaa aaaataataa agcatcactt   32820
acttaaaatc agttagcaaa tttctgtcca gtttattcag cagcacctcc ttgccctcct   32880
cccagctctg gtattgcagc ttcctcctgg ctgcaaactt tctccacaat ctaaatggaa   32940
tgtcagtttc ctcctgttcc tgtccatccg cacccactat cttcatgttg ttgcagatga   33000
agcgcgcaag accgtctgaa gataccttca accccgtgta tccatatgac acggaaaccg   33060
gtcctccaac tgtgcctttt cttactcctc cctttgtatc ccccaatggg tttcaagaga   33120
gtcccccctgg ggtactctct ttgcgcctat ccgaacctct agttacctcc aatggcatgc   33180
ttgcgctcaa aatgggcaac ggcctctctc tggacgaggc cggcaacctt acctcccaaa   33240
atgtaaccac tgtgagccca cctctcaaaa aaaccaagtc aaacataaac ctggaaatat   33300
ctgcaccccct cacagttacc tcagaagccc taactgtggc tgccgccgca cctctaatgg   33360
tcgcgggcaa cacactcacc atgcaatcac aggccccgct aaccgtgcac gactccaaac   33420
ttagcattgc cacccaagga cccctcacag tgtcagaagg aaagctagcc ctgcaaacat   33480
caggcccccct caccaccacc gatagcagta cccttactat cactgcctca ccccctctaa   33540
ctactgccac tggtagcttg ggcattgact tgaaagagcc catttataca caaaatggaa   33600
aactaggact aaagtacggg gctcctttgc atgtaacaga cgacctaaac acttgaccg    33660
tagcaactgc tccaggtgtg actattaata atacttcctt gcaaactaaa gttactggag   33720
ccttgggttt tgattcacaa ggcaaatatgc aacttaatgt agcaggagga ctaaggattg   33780
attctcaaaa cagacgcctt atacttgatg ttagttatcc gtttgatgct caaaaccaac   33840
taaatctaag actaggacag ggccctcttt ttataaactc agcccacaac ttggatatta   33900
actacaacaa aggcctttac ttgtttacag cttcaaacaa ttccaaaaag cttgaggtta   33960
acctaagcac tgccaagggg ttgatgtttg acgctacagc catagccatt aatgcaggag   34020
atgggcttga atttggttca cctaatgcac caaacacaaa tcccctcaaa acaaaaattg   34080
gccatggcct agaatttgat tcaaacaagg ctatggttcc taaactagga actggcctta   34140
gttttgacag cacaggtgcc attacagtag gaaacaaaaa taatgataag ctaactttgt   34200
ggaccacacc agctccatct cctaactgta gactaaatgc agagaaagat gctaaactca   34260
ctttggtctt aacaaaatgt ggcagtcaaa tacttgctac agtttcagtt ttggctgtta   34320
aaggcagttt ggctccaata tctggaacag ttcaaagtgc tcatcttatt ataagatttg   34380
acgaaaatgg agtgctacta aacaattcct tcctggaccc agaatattgg aactttagaa   34440
atggagatct tactgaaggc acagcctata caaacgctgt tggatttatg cctaacctat   34500
cagcttatcc aaaatctcac ggtaaaactg ccaaaagtaa cattgtcagt caagtttact   34560
taaacggaga caaaactaaa cctgtaacac taaccattac actaaacggt acacaggaaa   34620
caggagacac aactccaagt gcatactcta tgtcattttc atgggactgg tctggccaca   34680
actacattaa tgaaatattt gccacatcct cttacctttt ttcatacatt gcccaagaat   34740
aaagaatcgt ttgtgttatg tttcaacgtg tttattttc aattgcagaa aatttcaagt   34800
cattttttcat tcagtagtat agccccacca ccacatagct tatacagatc accgtacctt   34860
aatcaaactc acagaaccct agtattcaac ctgccacctc cctcccaaca cacagagtac   34920
acagtccttt ctccccggct ggccttaaaa agcatcatat catgggtaac agacatattc   34980
ttaggtgtta tattccacac ggtttcctgt cgagccaaac gctcatcagt gatattaata   35040
aactccccgg gcagctcact taagttcatg tcgctgtcca gctgctgagc cacaggctgc   35100
tgtccaactt gcggttgctt aacgggcggc gaaggagaag tccacgccta catgggggta   35160
gagtcataat cgtgcatcag gatagggcgg tggtgctgca gcagcgcgcg aataaactgc   35220
tgccgccgcc gctccgtcct gcaggaatac aacatggcag tggtctcctc agcgatgatt   35280
cgcaccgccc gcagcataag cgcgcttgtc ctccgggcac agcagcgcac cctgatctca   35340
cttaaatcag cacagtaact gcagcacagc accacaatat tgttcaaaat cccacagtgc   35400
aaggcgctgt atccaaagct catggcgggg accacagaac ccacgtggcc atcataccac   35460
aagcgcaggt agattaagtg gcgacccctc ataaacagc tggacataaa cattacctct   35520
tttggcatgt tgtaattcac cacctcccgg taccatataa acctctgatt aaacatggcg   35580
ccatccacca ccatcctaaa ccagctggcc aaaacctgcc cgccggctat acactgcagg   35640
gaaccgggac tggaacaatg acagtggaga gcccaggact cgtaaccatg gatcatcatg   35700
ctcgtcatga tatcaatgtt ggcacaacac aggcacacgt gcatacactt cctcaggatt   35760
acaagctcct cccgcgttag aaccatatcc cagggaacaa cccattcctg aatcagcgta   35820
aatcccacac tgcagggaag acctcgcacg taactcacgt tgtgcattgt caaagtgtta   35880
cattcgggca gcagcggatg atcctccagt atggtagcgc gggtttctgt ctcaaaagga   35940
ggtagacgat ccctactgta cggagtgcgc cgagacaacc gagatcgtgt tggtcgtagt   36000
gtcatgccaa atggaacgcc ggacgtagtc atatttcctg aagcaaaacc aggtgcgggc   36060
gtgacaaaca gatctgcgtc tccggtctcg ccgcttagat cgctctgtgt agtagttgta   36120
gtatatccac tctctcaaag catccaggcg cccccctggct tcgggttcta tgtaaactcc   36180
ttcatgcgc gctgccctga taacatccac caccgcagaa taagccacac ccagccaacc   36240
tacacattcg ttctgcgagt cacacacggg aggagcggga agagctggaa gaaccatgt   36300
ttttttttta ttccaaaaga ttatccaaaa cctcaaaatg aagatctatt aagtgaacgc   36360
gctcccctcc ggtggcgtgg tcaaactcta cagccaaaga acagataatg gcatttgtaa   36420
gatgttgcac aatggcttcc aaaaggcaaa cggccctcac gtccaagtgg acgtaaaggc   36480
taaacccttc agggtgaatc tcctctataa acattccagc accttcaacc atgcccaaat   36540
aattctcatc tcgccacctt ctcaatatat ctctaagcaa atcccgaata ttaagtccgg   36600
ccattgtaaa aatcttgtcc gagagcgccct ccaccttcag cctcaagcag cgaatcatga   36660
ttgcaaaaat tcaggttcct cacagacctg tataagattc aaaagcggaa cattaacaaa   36720
aataccgcga tcccgtaggt ccccttcgcag ggccagctga acataatcgt gcaggtctgc   36780
acggaccagc gcggccactt ccccgccagg aaccttgaca aaagaaccca cactgattat   36840
gacacgcata ctcggagcta tgctaaccag cgtagcccg atgtaagctt tgttgcatgg   36900
gcggcgatat aaaatgcaag gtgctgctca aaaaatcagg caaagcctcg cgcaaaaaag   36960
```

-continued

```
aaagcacatc gtagtcatgc tcatgcagat aaaggcaggt aagctccgga accaccacag  37020
aaaaagacac cattttttctc tcaaacatgt ctgcgggttt ctgcataaac acaaaataaa  37080
ataacaaaaa aacatttaaa cattagaagc ctgtcttaca acaggaaaaa caacccttat  37140
aagcataaga cggactacgg ccatgccggc gtgaccgtaa aaaaactggt caccgtgatt  37200
aaaaagcacc accgacagct cctcggtcat gtccggagtc ataatgtaag actcggtaaa  37260
cacatcaggt tgattcatcg gtcagtgcta aaaagcgacc gaaatagccc gggggaatac  37320
atacccgcag gcgtagagac aacattacag cccccatagg aggtataaca aaattaatag  37380
gagagaaaaa cacataaaca cctgaaaaac cctcctgcct aggcaaaata gcaccctccc  37440
gctccagaac aacatacagc gcttcacagc ggcagcctaa cagtcagcct taccagtaaa  37500
aaagaaaacc tattaaaaaa acaccactcg acacggcacc agctcaatca gtcacagtgt  37560
aaaaaagggc caagtgcaga gcgagtatat ataggactaa aaaatgacgt aacggttaaa  37620
gtccacaaaa aacacccaga aaaccgcacg cgaacctacg cccagaaacg aaagccaaaa  37680
aacccacaac ttcctcaaat cgtcacttcc gttttcccac gttacgtaac ttcccatttt  37740
aagaaaacta caattcccaa cacatacaag ttactccgcc ctaaaaccta cgtcacccgc  37800
cccgttccca cgccccgcgc cacgtcacaa actccacccc ctcattatca tattggcttc  37860
aatccaaaat aaggtatatt attgatgatn nn                                37892
```